US009409983B2

(12) United States Patent
Garcia

(10) Patent No.: US 9,409,983 B2
(45) Date of Patent: Aug. 9, 2016

(54) METHODS AND COMPOSITIONS INVOLVING PBEF INHIBITORS FOR LUNG INFLAMMATION CONDITIONS AND DISEASES

(75) Inventor: Joe G. N. Garcia, Chicago, IL (US)

(73) Assignee: The Board of Trustess of the University of Illinois, Urbana, IL (US)

( * ) Notice: Subject to any disclaimer, the term of this patent is extended or adjusted under 35 U.S.C. 154(b) by 401 days.

(21) Appl. No.: 12/842,773

(22) Filed: Jul. 23, 2010

(65) Prior Publication Data

US 2011/0020364 A1  Jan. 27, 2011

Related U.S. Application Data

(60) Provisional application No. 61/227,878, filed on Jul. 23, 2009.

(51) Int. Cl.
*A61K 39/00* (2006.01)
*A61K 38/00* (2006.01)
*C07K 14/00* (2006.01)
*C07K 16/24* (2006.01)
*C12N 15/113* (2010.01)

(52) U.S. Cl.
CPC .......... *C07K 16/243* (2013.01); *C12N 15/1136* (2013.01); *A61K 2039/505* (2013.01); *C07K 2317/76* (2013.01); *C12N 2310/14* (2013.01)

(58) Field of Classification Search
CPC . A61K 39/00; A61K 39/395; A61K 39/3955; A61K 39/39541; A61K 38/00
USPC .......................................... 424/158.1; 514/1.1
See application file for complete search history.

(56) References Cited

U.S. PATENT DOCUMENTS

| | | | |
|---|---|---|---|
| 4,415,723 A | 11/1983 | Hedges et al. | |
| 4,458,066 A | 7/1984 | Caruthers et al. | |
| 4,554,101 A | 11/1985 | Hopp et al. | |
| 4,683,195 A | 7/1987 | Mullis et al. | |
| 4,683,202 A | 7/1987 | Mullis et al. | |
| 4,797,368 A | 1/1989 | Carter et al. | |
| 4,800,159 A | 1/1989 | Mullis et al. | |
| 4,816,567 A | 3/1989 | Cabilly et al. | |
| 4,883,750 A | 11/1989 | Whiteley et al. | |
| 5,139,941 A | 8/1992 | Muzyczka et al. | |
| 5,187,260 A | 2/1993 | Karali et al. | |
| 5,194,596 A * | 3/1993 | Tischer et al. | 530/399 |
| 5,279,721 A | 1/1994 | Schmid | |
| 5,350,836 A * | 9/1994 | Kopchick et al. | 530/399 |
| 5,795,715 A | 8/1998 | Livache et al. | |
| 5,840,873 A | 11/1998 | Nelson et al. | |
| 5,843,640 A | 12/1998 | Patterson et al. | |
| 5,843,650 A | 12/1998 | Segev | |
| 5,843,651 A | 12/1998 | Stimpson et al. | |
| 5,843,663 A | 12/1998 | Stanley et al. | |
| 5,846,708 A | 12/1998 | Hollis et al. | |
| 5,846,709 A | 12/1998 | Segev | |
| 5,846,717 A | 12/1998 | Brow et al. | |
| 5,846,726 A | 12/1998 | Nadeau et al. | |
| 5,846,729 A | 12/1998 | Wu et al. | |
| 5,846,783 A | 12/1998 | Wu et al. | |
| 5,849,481 A | 12/1998 | Urdea et al. | |
| 5,849,486 A | 12/1998 | Heller et al. | |
| 5,849,487 A | 12/1998 | Hase et al. | |
| 5,849,497 A | 12/1998 | Steinman | |
| 5,849,546 A | 12/1998 | Sousa et al. | |
| 5,849,547 A | 12/1998 | Cleuziat et al. | |
| 5,851,772 A | 12/1998 | Mirzabekov et al. | |
| 5,853,990 A | 12/1998 | Winger et al. | |
| 5,853,992 A | 12/1998 | Glazer et al. | |
| 5,853,993 A | 12/1998 | Dellinger et al. | |
| 5,856,092 A | 1/1999 | Dale et al. | |
| 5,858,652 A | 1/1999 | Laffler et al. | |
| 5,861,244 A | 1/1999 | Wang et al. | |
| 5,863,732 A | 1/1999 | Richards | |
| 5,863,753 A | 1/1999 | Haugland et al. | |
| 5,866,331 A | 2/1999 | Singer et al. | |
| 5,866,366 A | 2/1999 | Kallender | |
| 5,882,864 A | 3/1999 | An et al. | |
| 5,889,136 A | 3/1999 | Scaringe et al. | |
| 5,900,481 A | 5/1999 | Lough et al. | |
| 5,905,024 A | 5/1999 | Mirzabekov et al. | |
| 5,910,407 A | 6/1999 | Vogelstein et al. | |
| 5,912,124 A | 6/1999 | Kumar | |
| 5,912,145 A | 6/1999 | Stanley | |

(Continued)

FOREIGN PATENT DOCUMENTS

| | | |
|---|---|---|
| EP | 320 308 | 6/1989 |
| EP | 329 822 | 8/1989 |
| GB | 2 202 328 | 9/1988 |
| WO | 8403564 | 9/1984 |
| WO | 8706270 | 10/1987 |
| WO | 8810315 | 12/1988 |

(Continued)

OTHER PUBLICATIONS

Hong et al., (Am J Respir Crit Care Med. Sep. 15, 2008;178(6):605-17. Epub Jul. 24, 2008).*
Ye et al., (Microvascular Res. Sep. 26, 2005. 70:142-151).*
Benjamin et al., 1998, Development 125:1591-1598.*
Vukicevic et al. 1996, PNAS USA 93:9021-9026.*
Massague, 1987, Cell 49:437-8.*
Pilbeam et al., 1993, Bone 14:717-720.*
Skolnick et al. 2000, Trends in Biotech. 18:34-39.*
Bork, 2000, Genome Research 10:398-400.*
Doerks et al., 1998, Trends in Genetics 14:248-250.*

(Continued)

*Primary Examiner* — Cherie M Stanfield
(74) *Attorney, Agent, or Firm* — McDonnell Boehnen Hulbert & Berghoff LLP

(57) ABSTRACT

The present invention concerns methods and compositions involving inhibitors of Pre-B Cell Colony Enhancing Factor (PBEF) for inflammatory conditions and diseases, including acute lung injury (ALI), ventilator-induced lung injury (VILI), and acute respiratory distress syndrome (ARDS). The present invention also concerns biomarkers for inflammation as well as methods for screening for PBEF inhibitors.

11 Claims, 19 Drawing Sheets

(56) References Cited

U.S. PATENT DOCUMENTS

| | | | |
|---|---|---|---|
| 5,912,148 | A | 6/1999 | Eggerding |
| 5,916,776 | A | 6/1999 | Kumar |
| 5,916,779 | A | 6/1999 | Pearson et al. |
| 5,919,626 | A | 7/1999 | Shi et al. |
| 5,919,630 | A | 7/1999 | Nadeau et al. |
| 5,922,574 | A | 7/1999 | Minter |
| 5,925,517 | A | 7/1999 | Tyagi et al. |
| 5,928,862 | A | 7/1999 | Morrison |
| 5,928,869 | A | 7/1999 | Nadeau et al. |
| 5,928,905 | A | 7/1999 | Stemmer et al. |
| 5,928,906 | A | 7/1999 | Koster et al. |
| 5,929,227 | A | 7/1999 | Glazer |
| 5,932,413 | A | 8/1999 | Celebuski et al. |
| 5,932,451 | A | 8/1999 | Wang et al. |
| 5,935,791 | A | 8/1999 | Nadeau et al. |
| 5,935,825 | A | 8/1999 | Nishimura et al. |
| 5,939,291 | A | 8/1999 | Loewy et al. |
| 5,942,391 | A | 8/1999 | Zhang et al. |
| 2003/0147966 | A1 | 8/2003 | Franzen et al. |
| 2003/0223938 | A1 | 12/2003 | Nagy et al. |
| 2005/0143336 | A1 | 6/2005 | Ramesh et al. |
| 2009/0197922 | A1 | 8/2009 | Maitland et al. ............ 514/183 |

FOREIGN PATENT DOCUMENTS

| | | |
|---|---|---|
| WO | 8906700 | 7/1989 |
| WO | 89 09284 | 10/1989 |
| WO | 9807408 | 2/1998 |
| WO | 9932619 | 7/1999 |
| WO | 0044914 | 8/2000 |
| WO | 0168836 | 9/2001 |
| WO | WO 2009/033047 | 3/2009 |

OTHER PUBLICATIONS

Smith et al.,1997, Nature Biotechnology 15:1222-1223.*
Brenner, 1999, Trends in Genetics 15:132-133.*
Bork et al., 1996, Trends in Genetics 12:425-427.*
Busso et al., (PLOS ONE 3. May 21, 2008;3(5):e2267. doi: 10.1371/journal.pone.0002267. pp. 1-10).*
McGlothlin et al., (Biochem Genetics. Apr. 2005;43(3-4);127-41; Abstract Only).*
Ye et al., (Am J Respir Crit Care Med. Feb. 15, 2005;171(4):361-70. Epub Dec. 3, 2004).*
Dreyfuss et al., "High inflation pressure pulmonary edema. Respective effects of high airway pressure, high tidal volume, and positive end-expiratory pressure," *Am. Rev. Respir. Dis.*, 137:1159-1164, 1988.
Dudek et al., "H(2)O(2)-mediated oxidative stress activates NF-kappa B in lens epithelial cells," *Free Radic. Biol. Med.*, 31:651-658, 2001.
Garcia et al., "Constitutive activation of Stat3 by the SRC and JAK tyrosine kinases participates in growth regulation of human breast carcinoma cells," *Oncogene*, 20:2499-2513, 2001.
GenBank Accession No. NM_000576, "*Homo sapiens* interleukin 1, beta (IL 1B), mRNA," 1991.
GenBank Accession No. NM_000594, "*Homo sapiens* tumor necrosis factor (TNF), mRNA,"1990.
GenBank Accession No. NM_000600, "*Homo sapiens* interleukin 6 (interferon, beta 2) (IL6), mRNA," 1990.
GenBank Accession No. NM_001511, *Homo sapiens* chemokine (C-X-C motif) ligand I (melanoma growth stimulating activity, alpha) (CXCL1), mrna, 1990.
GenBank Accession No. NM_002089, "*Homo sapiens* chemokine (C-X-C motif) ligand 2 (CXCL2), mRNA," 1990.
GenBank Accession No. NM_005746, "*Homo sapiens* nicotinamide phosphoribosyltransferase (NAMPT), mRNA," 1990.
Gene Ontology Consortium, "The Gene Ontology (GO) project in 2006," *Nucleic Acids Res.*, 34:D322-326, 2006.
Holen et al., "The pharmacokinetics, toxicities, and biologi effects of FK866, a nicotinamide adenine dinucleotide biosynthesis inhibitor," *Invest. New Drugs*, 26:45-51, 2008.
Hong et al., "Essential role of Pre-B cell colony enhancing factor in ventialtor-induced lung injury," *Am. J. Respir. Crit. Care Med.*, 178:605-617, 2008.
Jia et al., "Pre-B cell colony-enhancing factor inhibits neutrophil apoptosis in experimental inflammation and clinical sepsis," *J. Clin. Invest.*, 113:1318-1327, 2004.
Li and Wong, "Model-based analysis of oligonucleotide arrays: expression index computation and outlier detection," *Proc. Natl. Acad. Sci. USA*, 98:31-36, 2001.
Luscher et al., "The internist and the vessel wall, "*Neth. J. Med.*, 50(5):204-210, 1997.
Ma et al., "Bioinformatic identification of novel early stress response genes in rodent models of lung injury," *Am. J. Physiol. Lung Cell Mol. Physiol.*, 289:L468-477, 2005.
Moitra et al., "Re-evaluation of Evans Blue dye as a marker of albumin clearance in murine models of acute lung injury," *Transl. Res.*, 150:253-265, 2007.
Nichols et al., "Establishment of germ-line-competent embryonic stem (ES) cells using differentiation inhibiting activity," *Development*, 110:1341-1348, 1990.
Nonas et al., "Use of consomic rats for genomic insights into ventilator-associated lung injury," *Am. J. Physiol. Lung Cell Mol. Physiol.*, 293:L292-302, 2007.
Parsons et al., "Lower tidal volume ventilation and plasma cytokine markers of inflammation in patients with acute lung injury ," *Crit. Care Med.*, 33:1-6; discussion 230-232, 2005.
Pearson, "Endothelial cell biology," *Radiology*, 179(1):9-14, 1991.
Peng et al., "Protective effects of sphingosine 1-phosphate in murine endotoxin-induced inflammatory lung injury," *Am. J. Respir. Crit. Care Med*, 169:1245-1251, 2004.
Ranieri et al., "Effect of Mechanical Ventilation on Inflammatory Mediators in Patients With Acute Respiratory Distress Syndrome: A Randomized Controlled Trial," *JAMA*, 282:54-61, 1999.
Revollo et al., "NAMPT/PBEF/Visfatin regulates insulin secretion in beta cells as a systemic NAD biosynthetic enzyme," *Cell Metab.*, 6(5):363-375, 2007.
Revollo et al., "The NAD biosynthesis pathway mediated by nicotinamide phosphoribosyltransferase regulates Sir2 activity in mammalian cells, "*J Biol Chem.*, 279(49):50754-50763, 2004.
Rubenfeld et al., "Incidence and outcomes of acute lung injury," *N. Engl. J. Med.*, 353:1685-1693, 2005.
Samal et al., "Cloning and characterization of the cDNA encoding a novel human pre-B-cell colony-enhancing factor," *Mol. Cell Biol.*, 14(2):1431-1417, 1994.
Slutsky and Tremblay, "Multiple system organ failure. Is mechanical ventilation a contributing factor?," *Am. J. Respir. Crit. Care Med.*, 157:1721-1725, 1998.
The Acute Respiratory Distress Syndrome Network "Ventilation with lower tidal volumes as compared with traditional tidal volumes for acute lung injury and the acute respiratory distress syndrome. The Acute Respiratory Distress Syndrome Network," , *N. Engl. J. Med*, 342:1301-1308, 2000.
The R Development Core Team, "R: A language and environment for statistical computing," available online at http://cran.r-project.org/doc/manuals/refman.pdf, ISBN 3-900051-07-0, 2005.
Toole, "Hyaluronan: from extracellular glue to pericellular cue," *Nat. Rev. Cancer*, 4(7):528-539, 2004.
Tremblay et al., "Injurious ventilation induces widespread pulmonary epithelial expression of tumor necrosis factor-alpha and interleukin-6 messenger RNA," *Crit. Care Med.*, 30:1693-1700, 2002.
Tremblay et al., "Injurious ventilatory strategies increase cytokines and c-fos m-RNA expression in an isolated rat lung model," *J. Clin. Invest.*, 99:944-952, 1997.
Turley et al., "Signaling properties of hyaluronan receptors," *J. Biol. Chem.*, 277(7):4589-4592, 2002.
U.S. Appl. No. 60/970,857, entitled "Methods and Compositions for Treating Diseases and Conditions Involving Higher Molecular Weight Hyaluronan ," filed Sep. 7, 2007.
Ware and Matthay, "The acute respiratory distress syndrome," *N. Engl. I Med.*, 342 :1334-1349, 2000.

(56) References Cited

OTHER PUBLICATIONS

Wu et al., *J. Am.* "Engineering of a dermal equivalent: seeding and culturing fibroblasts in PEGT/PBT copolymer scaffolds," *Tissue Engineering*, 9(5):909-917, 2003.
Ye et al., "Pre-B-cell colony-enhancing factor as a potential novel biomarker in acute lung injury," *Am. J. Respir. Crit. Care Med.*, 171:361-370, 2005.
Aksentijevich, et al., Hum. Gene Ther., 7(9):1111-1122, 1996.
Bellus, J. Macromol. Sci. Pure Appl. Chem., A31(1): 1355-1376, 1994.
Bosher and Labouesse, Nat. Cell. Biol., 2(2):E31-E36, 2000.
Caplen, et al., Gene 252(1-2):95-105, 2000.
Chada, et al., Mol. Ther., 7:S446, 2003.
Clackson, et al., Nature, 352:624-628, 1991.
Consortium, Nucleic Acids res., 34:D322-D326, 2006.
Elbashir, et al., Nature, 411(6836):494-498, 2001.
Feigner, et al., Proc. Natl. Acad. Sci. USA, 84(21):7413-7417, 1987.
Fire, et al., Nature, 391(6669):806-811, 1998.
Fodor et al., Science, 251:767-777, 1991.
Fraley et al., Proc. Natl. Acad. Sci. USA, 76:3348-3352, 1979.
Gabizon et al., Cancer Res., 50(19):6371-6378, 1990.
Ghosh and Bachhawat, In: Liver Diseases, Targeted Diagnosis and Therapy Using Specific Receptors and Ligands, Wu et al. (Eds.), Marcel Dekker, NY, 87-104, 1991.
Grishok et al., Science, 287:2494-2497, 2000.
Hacia et al., Nature Genet., 14:441-447, 1996.
Innis et al., Proc. Natl. Acad. Sci. USA, 85(24):9436-9440, 1988.
Inouye and Inouye, Nucleic Acids Res., 13:3101-3109, 1985.
Kaneda et al., Science, 243:375-378, 1989.
Karlsson et al., EMBO J., 5:2377-2385, 1986.
Kato et al, J. Biol. Chem., 266:3361-3364, 1991.
Ketting et al, Cell, 99(2):133-141, 1999.
Kohler and Milstein, Nature, 256:495-497, 1975.
Kwoh et al., Proc. Natl. Acad. Sci. USA, 86:1173-1177, 1989.
Lin and Avery, Nature, 402:128-129, 1999.
Liu et al., Cancer Res., 55(14):3117-3122, 1995.
Macejak and Sarnow, Nature, 353:90-94, 1991.
Mann et al, Cell, 33:153-159, 1983.
Marks et al., J. Mol. Biol., 222:581-597, 1991.
Montgomery et al., Proc. Natl. Acad. Sci. USA, 95:15502-15507, 1998.
Nicolas and Rubinstein, In: Vectors: A survey of molecular cloning vectors and their uses, Rodriguez and Denhardt, eds., Stoneham: Butterworth, pp. 494-513, 1988.
Nicolau and Sene, Biochim. Biophys. Acta, 721:185-190, 1982.
Nicolau et al., Methods Enzymol, 149:157-176, 1987.
Ohara et al., Proc. Natl. Acad. Sci. USA, 86:5673-5677, 1989.
Paskind et al., Virology, 67:242-248, 1975.
Pease et al., Proc. Natl. Acad. Sci. USA, 91:5022-5026, 1994.
Pelletier and Sonenberg, Nature, 334(6180):320-325, 1988.
Sharp and Zamore, Science, 287:2431-2433, 2000.
Sharp, Genes Dev., 13:139-141, 1999.
Shoemaker et al., Nature Genetics, 14:450-456, 1996.
Smyth-Templeton et al., DNA Cell Biol., 21(12):857-867, 2002.
Solodin et al., Biochemistry, 34(41):13537-13544, 1995.
Tabara et al., Cell, 99(2):123-132, 1999.
Temin, In: Gene Transfer, Kucherlapati (Ed.), NY, Plenum Press, 149-188, 1986.
Templeton et al., Nat. Biotechnol., 15(7):647-652, 1997.
Thierry et al., Proc. Natl. Acad. Sci. USA, 92(21):9742-9746, 1995.
Tsukamoto et al., Nat. Genet., 9(3):243-248, 1995.
Walker et al., Nucleic Acids Res. 20(7):1691-1696, 1992.
Wincott et al., Nucleic Acids Res., 23(14):2677-2684, 1995.
Wong et al., Gene, 10:87-94, 1980.
Yang and Huang, Gene Therapy, 4 (9):950-960, 1997.
Zhu et al., Science, 261(5118):209-211, 1993.
Binnie, et al., "Biomarkers in acute respiratory distress syndrome", Curr Opin Crit Care. Feb. 2014;20(1):47-55.
Cross, et al., "Biomarkers in acute lung injury: insights into the pathogenesis of acute lung injury", Crit Care Clin., Apr. 2011; 27(2):355-77.

\* cited by examiner

A.

B

Fig. 1 Intratracheal siPBEF administration inhibits PBEF expression in mouse lung

METHODS AND COMPOSITIONS INVOLVING PBEF INHIBITORS FOR LUNG INFLAMMATION CONDITIONS AND DISEASES

This application claims priority to U.S. Provisional Patent application 61/227,878 filed Jul. 23, 2009, which is incorporated herein by reference in its entirety.

This invention was made with government support under HL 58064 awarded by the National Institutes of Health. The government has certain rights in the invention.

BACKGROUND OF THE INVENTION

I. Field of the Invention

The present invention relates generally to the fields of medicine, molecular biology, and biochemistry. More particularly, methods and compositions involving PBEF and PBEF inhibitors, including preventative, therapeutic, and diagnostic applications for inflammatory lung diseases and conditions.

II. Background

Mechanical ventilation is a life-saving intervention in critically ill patients with respiratory failure due to acute lung injury (ALI), a devastating syndrome characterized by profound lung inflammation, vascular permeability, and protein-rich alveolar edema (Rubenfeld et al., 2005; Ware and Matthay, 2000). Unfortunately, mechanical ventilation also potentially contributes directly to lung injury, a process known as ventilator-induced lung injury (VILI) with augmented capillary leakage, acute inflammation, and increases in inflammatory cytokine expression (Ranieri et al., 1999; Dreyfuss et al., 1988; Tremblay et al., 2002; Slutsky and Tremblay, 1998; Tremblay et al., 1997). The clinical relevance of VILI was highlighted by the landmark ARDSnet trial which reported decreased mortality in ARDS patients placed on low tidal volume ventilation, accompanied by decreases in BAL leukocytes and inflammatory cytokines (The acute respiratory distress syndrome network, 2000; Parsons et al., 2005).

Despite improved understanding of ALI pathophysiology, the underlying mechanisms of the injurious effects of mechanical ventilation in the setting of ALI remain unclear and effective pharmacotherapy has not yet emerged.

SUMMARY OF THE INVENTION

The present invention is based on data set that demonstrates a role for Pre-B Cell Colony-Enhancing Factor (PBEF) in inflammatory conditions and diseases, including such conditions and diseases that affect the lungs. Moreover, there are examples showing that inhibition of PBEF activity under conditions that reflect an inflammatory lung disease results in positive benefits. Therefore, the present invention concerns methods and compositions involving PBEF inhibitors for preventative and therapeutic applications for inflammatory lung conditions and diseases. The present invention further concerns methods of screening additional PBEF inhibitors.

The present invention is also based on data concerning genes whose expression is altered in acute lung injury (ALI), an inflammatory lung disease. Consequently, the present invention includes methods of diagnosing ALI using one or more biomarkers.

Therefore, in some embodiments, the present invention concerns methods for treating or preventing an inflammatory condition or disease in a patient comprising administering to a patient with an inflammatory condition or disease or at risk for an inflammatory condition or disease a Pre-B Cell Colony-Enhancing Factor (PBEF) inhibitor.

In some embodiments, the present invention concerns methods for treating or preventing an inflammatory condition or disease of the lungs in a patient comprising administering to a patient an effective amount of a Pre-B Cell Colony-Enhancing Factor (PBEF) inhibitor, wherein the patient has an inflammatory condition or disease of the lungs or is at risk for an inflammatory condition or disease of the lungs. A "PBEF inhibitor" refers to a substance that directly inhibits the activity or expression of PBEF, which means the inhibitor acts directly on a PBEF nucleic acid (DNA- or RNA-encoding sequence) or PBEF polypeptide. In specific embodiments, a PBEF inhibitor is a PBEF activity inhibitor meaning the inhibitor directly inhibits PBEF by acting on the PBEF polypeptide and inhibiting the activity of the polypeptide. In other embodiments a PBEF inhibitor is a PBEF expression inhibitor meaning the inhibitor directly inhibits PBEF by acting on a PBEF nucleic acid to inhibit the expression of the PBEF polypeptide. It is also contemplated with some embodiments that a PBEF inhibitor acts by preventing a compound that typically interacts with PBEF from interacting with PBEF, including by preventing binding of the compound to or with PBEF. The inhibitor may bind to PBEF and induce a conformation change that affects the ability of the compound and PBEF to bind each other or it could sterically block or mask all or part of PBEF that is involved in binding to or with the compound. In certain embodiments, the compound is a PBEF receptor.

An "effective amount" refers to the amount of a therapeutic or prophylactic composition that achieves the intended goal. In some embodiments, the intended goal is to prevent or treat an inflammatory condition or disease, which means an effective amount is that amount expected to achieve some prevention or treatment of the inflammatory condition or disease. In some embodiments it refers to preventing or alleviating symptoms and/or cellular processes associated with a particular disease or condition, including but not limited to VILI, ALI or ARDS; such symptoms may be vascular permeability or elevated BAL protein secretion). An inflammatory disease or condition refers to a disease or condition that is characterized by inflammation. The inflammation may affect any of the following tissue or organs: heart, lung, kidney, liver, bone marrow, pancreas, brain, skin, bone, vein, artery, cornea, ear, eye, nasopharyngeal tissue, stomach, joints, cartilage, vascular tissue or cells, blood, small intestine, large intestine, larynx, brain, spinal cord, smooth muscle, nerves, skeletal muscle, breast, ovary, testis, uterus, and umbilical cord. Moreover, the tissue can contain one or more of the following cell types: platelet, myelocyte, erythrocyte, lymphocyte, adipocyte, fibroblast, epithelial cell, endothelial cell, smooth muscle cell, skeletal muscle cell, endocrine cell, glial cell, neuron, secretory cell, barrier function cell, contractile cell, absorptive cell, mucosal cell, limbus cell (from cornea), stem cell (totipotent, pluripotent or multipotent), unfertilized or fertilized oocyte, or sperm.

The present invention also concerns methods comprising administering to a patient a PBEF inhibitor because the patient has symptoms of an inflammatory lung condition or disease or is at risk for an inflammatory lung condition or disease.

In certain embodiments of the invention, methods include identifying a patient in need of a therapeutic or preventative agent for the treatment of a particular disease or condition. In specific embodiments, the disease or condition is an inflammatory disease or condition. In even further embodiments, the inflammatory disease or condition does not include cancer or at least cancer treatment with a small molecule.

In other embodiments there are methods for treating a patient with or at risk for acute lung injury (ALI), ventilator-induced lung injury (VILI), or acute respiratory distress syndrome (ARDS) comprising administering to the patient an effective amount of a Pre-B Cell Colony-Enhancing Factor (PBEF) inhibitor. At risk patients include, but are not limited to, patients with sepsis or symptoms of sepsis, patients with pneumonia or symptoms of pneumonia, patients with severe bleeding because of an injury to the body, patients who have a severe injury to the chest or head, patients who have breathed harmful fumes or smoke, and patients inhaled vomit, patients who have had multiple or massive blood transfusions, patients who have fractured long bones (such as the femur), patients who have nearly drowned, patients who have had an adverse reaction to cancer drugs or other medications, patients who have had a drug overdose, patients with pancreatitis, patients who smoke heavily, patients who drink heavily, patients with inflammatory bowel disease, patients with rheumatoid arthritis, patients with colorectal cancer, and patients with obesity-related insulin resistance, or any combination thereof.

In particular embodiments, the inhibitor is a polypeptide, nucleic acid, or small molecule. It is contemplated that PBEF inhibitors may bind to or interfere with PBEF protein so as to inhibit PBEF activity. Alternatively, PBEF inhibitors may bind to or interfere with PBEF-encoding nucleic acids so as to inhibit PBEF expression.

In certain applications, the inhibitor is a polypeptide. Polypeptides include, but are not limited to, all or part of antibody that specifically recognizes or binds to PBEF. The antibody may a polyclonal antibody or a monoclonal antibody. In particular embodiments, the antibody comprises a single chain variable fragment. It is contemplated that antibody inhibitors of the invention may be a neutralizing antibody. In additional embodiments of the invention, the antibody is a humanized antibody, chimeric antibody, or single chain antibody. In other embodiments, certain polypeptide inhibitors may instead inhibit PBEF expression, for example, by inhibiting PBEF transcription.

In further embodiments of the invention the inhibitor is a nucleic acid. In certain embodiments, the nucleic acid is an siRNA meaning the inhibitor is fully or partially complementary (has complementarity) to a PBEF-encoding nucleic acid and inhibits PBEF expression. In certain embodiments, the siRNA is a single- or double-stranded nucleic acid with a contiguous sequence of at least 10 contiguous nucleotides of SEQ ID NO:1. Other examples of siRNAs are disclosed herein and may be used in embodiments of the invention.

In other embodiments, the inhibitor is a small molecule. In particular embodiments, the PBEF inhibitor is FK-866.

The present invention concerns inflammatory diseases or conditions of the lungs. In certain embodiments, the inflammatory disease or condition is acute lung injury (ALI), ventilator-induced lung injury (VILI), or acute respiratory distress syndrome (ARDS). Methods of the invention may be used to prevent or treat these lung conditions/diseases.

In some embodiments, an inhibitor is administered to the patient intravenously, intraarterially, intraperitoneally, intrapleurally, intratracheally, topically, intraperitoneally, subcutaneously, mucosally, intrapericardially, orally, topically, locally, by inhalation, by injection, by infusion, by continuous infusion, by localized perfusion bathing target cells directly, via a catheter, via aerosol, via nebulizer, and/or via a lavage. In certain cases, a PBEF inhibitor is administered intratracheally or intravenously. In other embodiments, the PBEF inhibitor is administered directly to a tissue or organ that is inflamed or shows signs of inflammation.

It is contemplated that methods may be applied to any animal capable of developing inflammation in the lungs. In particular embodiments, the subject is a mammal, including but not limited to humans. In certain embodiments, a patient is suspected of having an inflammatory lung condition or disease. This may be based on the patient's symptoms, medical history, or the results of one or more tests. In some cases, a patient has already been diagnosed with an inflammatory condition or disease of the lungs when the patient is administered the PBEF inhibitor. In other cases, the patient has not been diagnosed with an inflammatory condition or disease of the lungs but the patient is at risk for such a disease or condition. Such a patient includes one who has been placed or will be placed on a ventilator, someone with pneumonia, someone who has experienced bodily trauma, someone with severe bleeding, someone who has aspirated vomit, someone who has inhaled chemicals, someone who has smoked heavily or someone who drinks heavily. For instance, the patient may be placed on a ventilator or have been on a ventilator within 1, 2, 3, 4, 5, 6, 7, 8, 9, 10, 11, 12, 13, 14, 15, 16, 17, 18, 19, 20, 21, 22, 23, 24, 30, 36, 42, 48, 54, 60, 66, 72, 78, 84, 90, 96, 102, 108, 114, 120 hours (or any range derivable therein) and/or 1, 2, 3, 4, 5, 6, 7 days (or any range derivable therein).

In certain embodiments the patient is administered the PBEF inhibitor more than one time. Multi-dosages of the PBEF inhibitor may be given to the patient. Moreover, the patient may be given other treatment for the inflammatory lung condition or disease.

An inhibitor may be formulated in a pharmaceutically acceptable composition. In certain embodiments, a preservative and/or stabilizer is included in the composition.

The present invention also concerns methods for identifying a PBEF inhibitor for the treatment of an inflammatory condition or disease comprising: a) incubating a PBEF polypeptide or nucleic acid with a candidate substance; b) assaying for a level of inhibition of PBEF activity or expression; and c) determining whether that assayed level indicates the candidate substance is inhibiting PBEF activity or expression. In some embodiments, the level of inhibition of the candidate substance is compared to a level of inhibition of PBEF activity or expression in the absence of the candidate substance. If the assayed level from the candidate substance is lower than the level of activity or expression in the absence of the candidate substance, the candidate substance is a PBEF inhibitor. In other embodiments, the level of inhibition of the candidate substance is compared to a level of inhibition of PBEF activity or expression from a known PBEF inhibitor. If the level for the candidate substance is similar or lower than the level observed with the known inhibitor, the candidate substance is a PBEF inhibitor. Of course, the skilled artisan knows that comparing between levels of inhibition requires that a level of expression be compared to another level of expression or that a level of activity be compared to another level of activity (as opposed to comparing a level of activity to a level of expression). Methods also include a step d) of testing the candidate inhibitor in an animal model for the inflammatory condition or disease.

In other embodiments, there are methods of identifying a PBEF inhibitor that may be a therapeutic or preventative agent for an inflammatory disease or condition comprising administering to a subject with an inflammatory disease or condition a candidate PBEF inhibitor and assaying whether the candidate PBEF inhibitor reduces or alleviates the symptoms of the inflammatory disease or condition or effects a treatment of the inflammatory disease or condition. In some embodiments, the candidate PBEF inhibitor may be compared to a known PBEF inhibitor or a substance known to reduce or alleviate symptoms of an inflammatory disease or condition. In other embodiments, the candidate PBEF inhibitor may be compared to the absence of the candidate PBEF inhibitor in order to determine whether a reduction in symptoms or treatment of the disease or condition has occurred. A candidate PBEF inhibitor that reduced the severity, extent, or lethality of the condition or disease would identify a therapeutic PBEF inhibitor.

In additional embodiments, the candidate PBEF inhibitor is provided to a subject that is then exposed to conditions or circumstances that promote or cause an inflammatory disease or condition in the subject. The extent of prevention from the candidate PBEF inhibitor may be evaluated based on a comparison of the subject's symptoms or physiological characteristics in the absence of the candidate PBEF inhibitor. A candidate PBEF inhibitor that reduced the severity, extent, or lethality of the condition or disease compared to its absence would identify a preventative PBEF inhibitor.

PBEF activity includes but is not limited to cytokine activity, nicotinamide phosphoribosyltransferase activity, chemotactic factor, NF-κB signaling activity, redox signaling activity, or a role in mitochondrial function and apoptosis.

It is contemplated that the candidate substance may be a small molecule, nucleic acid, or polypeptide in some embodiments of the invention. It is also contemplated that methods may be implemented in high throughput assays or with arrays.

It is contemplated that in some embodiments the inflammatory condition or disease afflicts the lungs, such as ALI, VILI, or ARDS.

The present invention also concerns methods for identifying a patient with an inflammatory condition or disease or at risk for an inflammatory condition or disease comprising determining the level of expression of a nucleic acid that hybridizes to a BC018473 sequence under stringent conditions in a biological sample from the patient, wherein an increase in the level of expression compared to a biological sample from a normal patient indicates the patient has an inflammatory disease or condition or is at risk for such a disease or condition.

In other embodiments, there are methods for identifying a patient with symptoms of or at risk for an inflammatory disease or condition comprising a) obtaining information about the level of expression of BC018473 in a biological sample from the patient; and, b) diagnosing the patient with an inflammatory condition or disease if there is an increase in the level of expression in the biological sample from the patient compared to a biological sample from a normal patient.

The term "BC018473 sequence" refers to a nucleic acid that is complementary or identical to at least 70% of the full length BC018473 sequence shown in SEQ ID NO:3. It is contemplated that a BC018473 sequence may be further qualified as a nucleic acid sequence that is complementary or identical to at least 75%, 80%, 85%, 90% 95%, 96%, 97%, 98%, 99%, or 100%, or any range derivable therein, of the full length BC018473 sequence. The term "stringent conditions" refers to washing conditions of about 0.5× to about 1×SSC at 65° C. In certain embodiments, the BC018473 sequence hybridizes to a nucleic acid in a biological sample under "very stringent conditions," which refers to washing conditions of about 0.1×SSC to about 0.5×SSC at 65° C.

Additional aspects of the invention include methods for identifying a patient having an inflammatory disease or condition comprising: a) obtaining information from a biological sample from the patient about the level of expression of one or more biomarkers that include: PBEF, TNFα, CXCl, CXCl2, IL-1β, IL-6 and/or a nucleic acid that hybridizes to a BC018473 sequence under stringent conditions, and b) comparing the level of expression of the biomarker to determine whether the level is increased compared to a normal sample, wherein elevation of one or more biomarkers is indicative of an inflammatory disease or condition. It is contemplated that any combination of these biomarkers may be employed in methods and compositions of the invention. In certain embodiments, there are 1, 2, 3, 4, 5, 6, or 7, or any combination or range derivable therein, of such biomarkers in any method or kit of the invention.

In certain embodiments, a biological sample is blood, bronchioalveolar lavage, or sputum. In further embodiments method involve retrieving the biological sample from the patient. The patient may be one who has symptoms of an inflammatory disease or condition or one who is at risk for inflammatory disease or condition. In specific embodiments, methods involve determining the level of expression of one or more biomarkers. Such methods are well known to those of skill in the art. In certain cases, the level of expression is determined based on the level of corresponding RNA for the biomarker(s), which means that determining the level of expression involves determining the level of RNA transcript that corresponds to the particular biomarker. In other cases, the level of expression is determined based on the level of corresponding protein for the biomarker(s), which means that determining the level of expression involves determining the level of protein corresponding to (encoded by) the particular biomarker.

Additional aspects of the invention include a kit or diagnostic device comprising a microarray, chip or multiplex analyte diagnostic instrument for measuring one or more biomarkers that include: PBEF, TNFα, CXCl, CXCl2, IL-1β, IL-6 and/or a nucleic acid that hybridizes to a BC018473 sequence under stringent conditions. The embodiments discussed in the context of the methods may be specifically implemented in the context of the recited kits or devices. Consequently, it is contemplated that any combination of these biomarkers may be employed.

The human sequences corresponding to these biomarkers can be found as follows: PBEF (NM_0005746), TNFα NM_000594), CXCl1 (NM_001511), CXCl2 (NM_002089), IL-1β (NM_000576), and IL-6 (NM_000600), all of which are hereby incorporated by reference. It is contemplated that methods and kits may involve primers or probes that are complementary or identical to regions of contiguous sequences in those disclosed sequences. The general structure of such primers and probes are disclosed herein and they apply specifically to any of sequences of these biomarkers.

It is contemplated that an increase in the level of expression is determined based on one or more levels determined from comparable biological samples obtained from patients who have been determined not to have an inflammatory disease or condition or not at risk for such a disease or condition at the time the sample from them was obtained. This may be considered a control level of normal expression or a standardized level of normal expression where "normal" refers to a physiological condition that does not have symptoms of an inflammatory disease or condition.

In methods of the invention it is contemplated that expression may be determined using any number of assays well known to those of skill in the art including, but not limited to, amplification methods, reverse transcription methods, Northern blot analysis, or a combination thereof.

In additional aspects of the invention, methods include retrieving the biological sample from the patient. In other aspects, methods involve preparing a document or reviewing information reporting the level of expression or identifying the sample as from a patient with an inflammatory condition or disease or at risk for such a condition or disease. In certain embodiments, methods also concern diagnosing a patient with an inflammatory disease or condition following a determination of the level of a biomarker in a patient sample. Further embodiments concern treating a patient after identifying the patient as having an inflammatory disease or condition or at risk for such a disease or condition.

In other embodiments, methods include determining or having determined a level of expression of PBEF in a biological sample from a patient, wherein expression of PBEF at a level higher than in a normal sample is indicative of an inflammatory condition or disease or the risk of such a condition or disease. It is contemplated that the use of PBEF as a biomarker may be used in conjunction with BC018473 as a biomarker for inflammatory diseases or conditions. In certain embodiments, the inflammatory disease or condition is such a disease of the lungs, including, but not limited to, ALI, VILI, and ARDS. In particular embodiments, a patient is treated for ALI, VILI, or ARDS following steps of the method.

Embodiments also concern pharmaceutical compositions that include a PBEF inhibitor. The compositions may be formulated in a pharmaceutically acceptable composition. In certain embodiments, a preservative and/or stabilizer is included in the composition. Such compositions may be administered or prescribed to mammals, including humans.

Furthermore, in embodiments of the invention, methods may involve compositions containing about, at least about, or at most about 0.1, 0.2, 0.3, 0.4, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 21, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 ng, µg or mg of a PBEF inhibitor (or any range derivable therein), which may be in about, at least about, or at most about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 10, 11, 12, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µl or ml (or any range derivable therein). Moreover, such amounts may be administered to a subject as that much hyaluronan/kg body weight of the subject. For example, a subject may be administered an amount in the range of about 1 µg/kg and about 1 mg/kg. In certain embodiments, the amount given to a subject is about, at least about, or at most about 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 21, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µg/kg or mg/kg, or any range derivable therein. These amounts may be prescribed on a per administration basis or on a daily basis (for example on a µg/kg body weight/day basis).

Such amounts can be administered daily, though other dosing regimens are contemplated. It is contemplated that compositions of the invention may be administered just a single time or multiple times. In certain embodiments of the invention, a composition is administered 1, 2, 3, 4, 5, 6 or more times, or any range derivable therein. It is contemplated that a preventative or treatment regimen may involve multiple administrations over 1, 2, 3, 4, 5, 6, and/or 7 days or 1, 2, 3, 4, or 5 weeks, and/or 1, 2, 3, 4, 5, 6, 7, 8, 9, 10, 11, and/or 12 months, or any range derivable therein. Moreover, any such regimen may be repeated after a certain amount of time has passed or when symptoms of the disease or condition become noticeable or more severe.

In some embodiments a patient is also given one or more other treatments used for treating the disease or condition. Examples of such treatments include administration of anti-inflammatory drugs, corticosteroids (such as methylprednisolone), NSAIDS, or applying airway pressure release ventilation, or applying other ventilation techniques such as low tidal volume ventilation. A patient may have been treated previously or may be treated concurrently or in the future with such treatments.

Methods may further involve evaluating a candidate modulator that decreases HABP2 expression or activity as a treatment for vascular permeability or to inhibit angiogenesis. For instance, candidate modulators may be evaluated in cells, tissues, or animal to evaluate any relevant properties. Animal models may be employed to evaluate the candidate modulators.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The terms "inhibiting" and "reducing" or any variation of these terms, when used in the claims and/or the specification includes any measurable decrease or complete inhibition to achieve a desired result. The terms "prevention" and "preventing" refer to the expectation that something can be kept from happening to some extent or that the severity, duration, or extent of the condition or disease can be alleviated or reduced. It is contemplated that the terms "treating" or "preventing" in the context of a condition or disease refers to any reduction or inhibition of the disease or condition. In specific embodiments, the disease or condition is an inflammatory disease or condition. In certain other cases, the invention pertains to inflammatory diseases or condition that afflicts a certain cell type, tissue, organ or area of the body. In particular embodiments, the inflammatory condition or disease is a lung inflammatory condition or disease, which refers to a disease or condition characterized by inflammation in or of the lungs. In specific embodiments, the lung inflammatory disease is ALI, VILI, or ARDS.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1A:
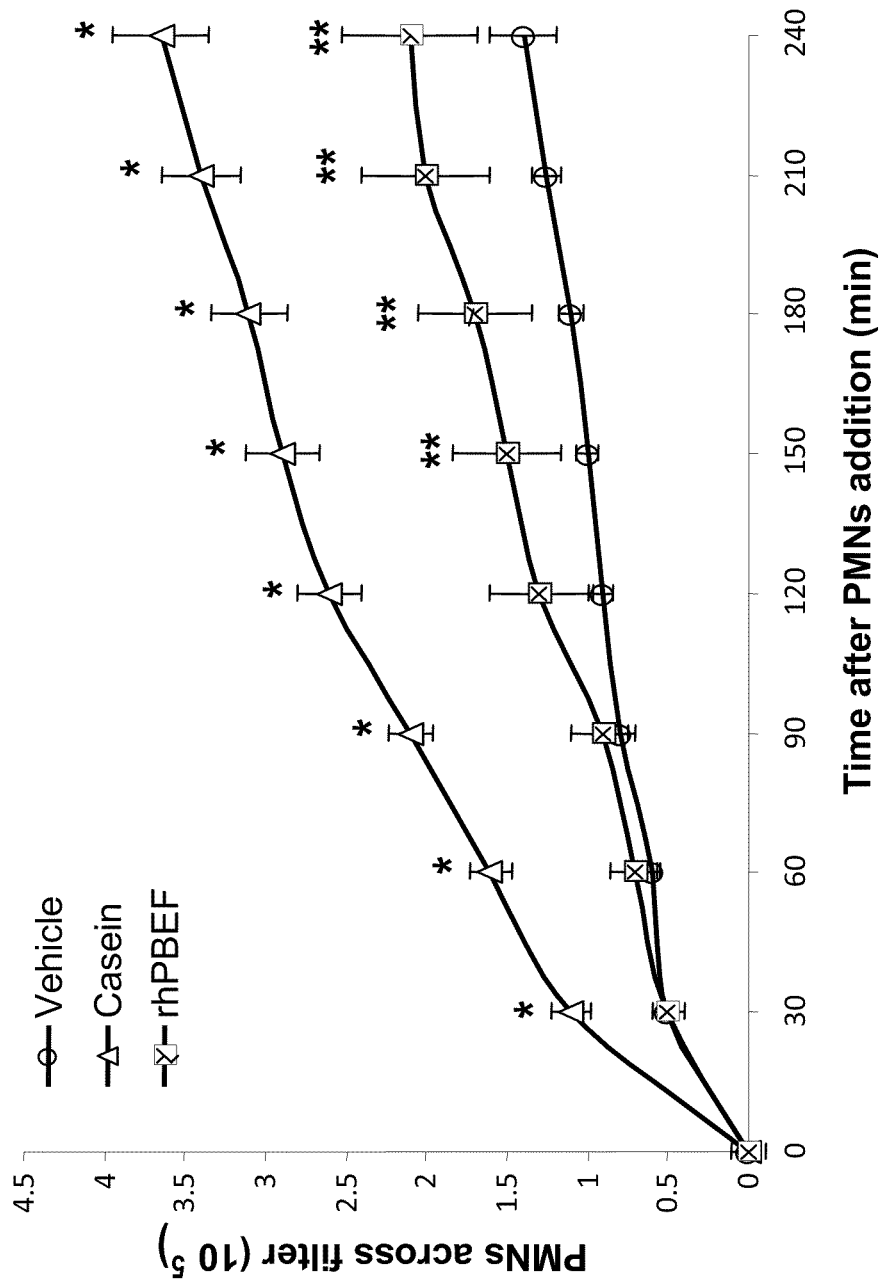
FIG. 1. In vitro and in vivo effects of rhPBEF on neutrophil chemotaxis and lung leukocyte recruitment. Panel A depicts the migration of rat peritoneal neutrophils (90% PMNs purity) across Transwell filters in response to rhPBEF or casein (lower chamber) for up to 4 hours. rhPBEF induced significant PMN migration beginning at 2 hrs (** $p<0.05$), whereas casein-mediated PMN migration was significant at all time points beginning at 30 minutes (* $p<0.05$) and diminishes after 210 minutes. Panel B demonstrates that rhPBEF instillation produces significant increases in number of BAL cells in C57BL/6 mice. (vehicle $22\times10^5\pm4$ vs. rhPBEF $83\times10^5\pm15$, x±SEM, * $p<0.01$) assessed 4 hours after instillation and compared to vehicle controls. BAL cell counts are further increased in mice receiving rhPBEF 30 min prior to mechanical ventilation (VILIa, 30 ml/kg, 4 hrs) when compared to VILIa alone (VILIa $33\times10^5\pm5$ vs. VILIa-rhPBEF $250\times10^5\pm21$, ** reflects $p<0.001$). Panel C depicts the significant increase in number of BAL neutrophils (PMNs) in rhPBEF-challenged mice (vehicle $0.4\times10^5\pm0.2$ vs. rhPBEF $38.8\times10^5\pm11.1$, * $p<0.01$) at 4 hours. BAL neutrophil counts were further increased in the VILIa-rhPBEF group compared to each group including VILIa alone (VILIa $1.4\times10^5\pm0.7$ vs. VILIa-rhPBEF $104.4\times10^5\pm17.8$, ** $p<0.001$). Panel D. Depicted is a representative cytospin result (400×) with the typical predominance of alveolar macrophages in BAL from vehicle-treated mice (left panel). In contrast, there is a dramatic influx of neutrophils into the alveolar space (right panel) after exposure to 20 μg rhPBEF in the VILIa-rhPBEF group. n=4~6 animals in all experimental groups.

The inner lining of all blood vessels is comprised of endothelial cells (EC), which regulate the interface between the blood and the vessel wall including vascular barrier regulation, passive diffusion and active transport of substances from the blood, regulation of vascular smooth muscle tone and blood clotting (Pearson, 1991; Luscher et al., 1997). Disruption of this semi-selective cellular barrier is a significant feature of inflammation, in addition to being a crucial contributing factor to atherosclerosis and tumor angiogenesis (Dudek et al., 2001; Garcia et al., 2001). Several bioactive agonists contribute to EC barrier regulation via direct effects on the integrity of EC junctions, cell-cell and cell-matrix adhesions. While previous reports have implicated one important extracellular matrix component, hyaluronan (HA), and its cell surface receptor, CD44 (Turley et al., 2002; Toole, 2004), the Examples provide evidence that these molecules are involved in normal EC function and angiogenesis.

Pre-B Cell Colony Enhancing Factor (PBEF)

Pre-B cell colony enhancing factor (PBEF) is also known as a nicotinamide phosphoribosyltransferase (Nampt) or visfatin. The human cDNA sequence is provided in GenBank Accession number NM_005746, which is hereby incorporated by reference. This sequence also corresponds to SEQ ID NO:1. The encoded protein sequence is provided as SEQ ID NO:2. PBEF was characterized as a proinflammatory cytokine based on its effect on the maturation of B cells. Samal et al. (1994) which is hereby incorporated by reference. It has also been reported to have nicotinamide phosphoribosyltransferase activity in addition to its cytokine activity (Revollo et al., 2004, which is hereby incorporated by reference). There are reports that it regulates insulin secretion in beta cells as a systemic NAD biosynthetic enzyme (Revollo et al., 2007, which is hereby incorporated by reference).

The present invention concerns compounds that inhibit PBEF and their use for treating or preventing inflammatory conditions and diseases. Inhibitors of PBEF can be evaluated based on their ability to inhibit directly PBEF activity or expression or based on their ability to effect prevention or treatment of an inflammatory disease or condition.

Diseases and Conditions

The present invention concerns methods and compositions that can be employed in the context of diagnosing, preventing or treating certain inflammatory conditions and diseases.

A. Inflammatory Conditions and Diseases

The present invention concerns the diagnosis, prevention, and treatment of inflammatory conditions and diseases. Inflammatory conditions and diseases refer to conditions or diseases of the body that are characterized by acute or chronic inflammation of tissue or organs involving the immune and vascular systems. Acute inflammation typically involves swelling, redness, pain, heat, and loss of function that is caused by infiltration of the tissues by plasma and leukocytes. Chronic inflammation generally involves 1) infiltration of mononuclear immune cells (such as monocytes, macrophages, lymphocytes, and plasma cells), 2) tissue destruction, and 3) healing efforts that involve angiogenesis and fibrosis. Examples of inflammatory conditions or diseases include, but are not limited to, asthma, autoimmune diseases, chronic prostatitis, glomerulonephritis, inflammatory bowel diseases, pelvic inflammatory diseases, reperfusion injury, rheumatoid arthritis, osteoarthritis, psoriasis, atherosclerosis, transplant rejection, ischemic heart disease, and vasculitis, though it is also contemplated that any of these may also be specifically excluded as part of the invention.

In certain embodiments, it is contemplated that methods and compositions of the invention are applied in the context of non-cancerous inflammatory diseases or conditions meaning the inflammatory disease or condition is not cancer, including specifically not colorectal cancer. In certain embodiments the invention concerns inflammatory diseases or conditions that are also immune system disorders, which may include autoimmune disorders. In particular embodiments, the condition or disease is or is not obesity-related insulin resistance.

In certain embodiments, the invention pertains to inflammatory conditions or diseases of the lungs. In even further embodiments, the inflammatory condition or disease of the lungs is ALI, VILI, and.or ARDS. Embodiments related to ALI and ARDS may be found in U.S. Provisional Patent Application 60/970,857 filed on Sep. 7, 2007, which is hereby incorporated by reference.

A more severe form of ALI is considered to be ARDS. Other names for ARDS include: Non-cardiogenic pulmonary edema; Increased-permeability pulmonary edema; Stiff lung; Shock lung; Adult respiratory distress syndrome.

Both ALI and ARDS are generally characterized by: bilateral pulmonary infiltrates based on a chest X-ray and a pulmonary capillary wedge pressure of less than 18 mmHg. ALI is usually characterized as having a $PaO_2/FiO_2$ of less than or equal to 300, while ARDS is characterized as having a $PaO_2/FiO_2$ of less than or equal to 200. Often there is widespread airway collapse (low lung volumes), surfactant deficiency and/or reduced lung compliance. VILI is a form of lung injury that results from ventilator use.

B. Nucleic Acids

The present invention concerns polynucleotides or nucleic acid molecules relating to PBEF sequences or BC018473 sequences in diagnostic, therapeutic, and preventative applications. In certain embodiments, the present invention specifically concerns a nucleic acid that serves as a PBEF inhibitor for the prevention or treatment of inflammatory conditions or diseases. In other embodiments, the present invention concerns a nucleic acid that can be used to diagnose an inflammatory disease or condition based on the detection of overexpression of a PBEF sequence or a sequence that hybridizes to a BC018473 sequence under stringent or highly stringent hybridization conditions. Nucleic acids or polynucleotides of the invention may be DNA or RNA, and they may be oligonucleotides (100 residues or fewer) in certain embodiments. Moreover, they may be recombinantly produced or synthetically produced.

These polynucleotides or nucleic acid molecules may be isolatable and purifiable from cells or they may be synthetically produced. In some embodiments of the invention, a PBEF-encoding nucleic acid is the target of a nucleic acid PBEF inhibitor, such as a ribozyme or siRNA that reduces the level of PBEF expression.

As used in this application, the term "polynucleotide" refers to a nucleic acid molecule, RNA or DNA, that has been isolated free of total genomic nucleic acid. Therefore, a "polynucleotide encoding PBEF" refers to a nucleic acid sequence (RNA or DNA) that contains PBEF coding sequences, yet may be isolated away from, or purified and free of, total genomic DNA and proteins.

The term "cDNA" is intended to refer to DNA prepared using RNA as a template. The advantage of using a cDNA, as opposed to genomic DNA or an RNA transcript is stability and the ability to manipulate the sequence using recombinant DNA technology (See Sambrook, 2001; Ausubel, 1996). There may be times when the full or partial genomic sequence is some. Alternatively, cDNAs may be advantageous because it represents coding regions of a polypeptide and eliminates introns and other regulatory regions. In certain embodiments, nucleic acids are complementary or identical to cDNA encoding sequences, such as a PBEF sequence or a BC018473 sequence.

The term "gene" is used for simplicity to refer to a functional protein, polypeptide, or peptide-encoding nucleic acid unit. As will be understood by those in the art, this functional term includes genomic sequences, cDNA sequences, and smaller engineered gene segments that express, or may be adapted to express, proteins, polypeptides, domains, peptides, fusion proteins, and mutants. The nucleic acid molecule hybridizing to BC018473 may comprise a contiguous nucleic acid sequence of the following lengths or at least the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, 12000 or more (or any range derivable therein) nucleotides, nucleosides, or base pairs of the BC018473 sequence. Such sequences may be identical or complementary to SEQ ID NO:3.

Accordingly, sequences that have or have at least or at most 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, and any range derivable therein, of nucleic acids that are identical or complementary to a nucleic acid sequence of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000 contiguous bases (or any range derivable therein) of SEQ ID NO:1 or SEQ ID NOs:3-9 are contemplated as part of the invention. They may be used as PBEF inhibitors or as detection probes or primers for methods of the invention.

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

1. Antisense Sequences, Including siRNAs

In particular embodiments, the invention concerns isolated nucleic acid segments and recombinant vectors incorporating DNA sequences that encode PBEF inhibitors, such as PBEF siRNAs, ribozymes and PBEF antibodies and other PBEF binding proteins or proteins that inhibit expression of PBEF transcripts.

In some embodiments, a nucleic acid may encode an antisense construct. Antisense methodology takes advantage of the fact that nucleic acids tend to pair with "complementary sequences." By complementary, it is meant that polynucleotides are those which are capable of base-pairing according to the standard Watson-Crick complementarity rules. Inclusion of less common bases such as inosine, 5-methylcytosine, 6-methyladenine, hypoxanthine and others in hybridizing sequences does not interfere with pairing.

Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

In certain embodiments, the nucleic acid encodes an interfering RNA or siRNA. RNA interference (also referred to as "RNA-mediated interference" or RNAi) is a mechanism by which gene expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin and Avery, 1999; Montgomery et al., 1998; Sharp and Zamore, 2000; Tabara et al., 1999). Activation of these mechanisms targets mature, dsRNA-complementary mRNA for destruction. Advantages of RNAi include a very high specificity, ease of movement across cell membranes, and prolonged down-regulation of the targeted gene (Fire et al., 1998; Grishok et al., 2000; Ketting et al., 1999; Lin and Avery et al., 1999; Montgomery et al., 1998; Sharp et al., 1999; Sharp and Zamore, 2000; Tabara et al., 1999). Moreover, dsRNA has been shown to silence genes in a wide range of systems, including plants, protozoans, fungi, *C. elegans*, *Trypanasoma*, *Drosophila*, and mammals (Grishok et al., 2000; Sharp et al., 1999; Sharp and Zamore, 2000; Elbashir et al., 2001). It is generally accepted that RNAi acts post-transcriptionally, targeting RNA transcripts for degradation. It appears that both nuclear and cytoplasmic RNA can be targeted (Bosher and Labouesse, 2000).

siRNAs are designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., 1998).

The making of siRNAs has been mainly through direct chemical synthesis; or through an in vitro system derived from S2 cells. Chemical synthesis proceeds by making two single stranded RNA-oligomers followed by the annealing of the two single stranded oligomers into a double-stranded RNA. Methods of chemical synthesis are diverse. Non-limiting examples are provided in U.S. Pat. Nos. 5,889,136, 4,415,723, and 4,458,066, expressly incorporated herein by reference, and in Wincott et al. (1995).

Several further modifications to siRNA sequences have been suggested in order to alter their stability or improve their effectiveness. It is suggested that synthetic complementary 21-mer RNAs having di-nucleotide overhangs (i.e., 19 complementary nucleotides +3' non-complementary dimers) may provide the greatest level of suppression. These protocols primarily use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

In some embodiments, the invention concerns an siRNA that is capable of triggering RNA interference, a process by which a particular RNA sequence is destroyed. siRNA are dsRNA molecules that are 100 bases or fewer in length (or have 100 basepairs or fewer in its complementarity region). In some cases, it has a 2 nucleotide 3' overhang and a 5' phosphate. The particular RNA sequence is targeted as a result of the complementarity between the dsRNA and the particular RNA sequence. It will be understood that dsRNA or siRNA of the invention can effect at least a 20, 30, 40, 50, 60, 70, 80, 90 percent or more reduction of expression of a targeted RNA in a cell. dsRNA of the invention (the term "dsRNA" will be understood to include "siRNA") is distinct and distinguishable from antisense and ribozyme molecules by virtue of the ability to trigger RNAi. Structurally, dsRNA molecules for RNAi differ from antisense and ribozyme molecules in that dsRNA has at least one region of complementarity within the RNA molecule. The complementary (also referred to as "complementarity") region comprises at least or at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous bases, or any range derivable therein, to sequences (or their complements) disclosed herein. In some embodiments, the sequence is any of SEQ ID NO:1 or SEQ ID NOs:3-9. In some embodiments, long dsRNA are employed in which "long" refers to dsRNA that are 1000 bases or longer (or 1000 basepairs or longer in complementarity region). The term "dsRNA" includes "long dsRNA" and "intermediate dsRNA" unless otherwise indicated. In some embodiments of the invention, dsRNA can exclude the use of siRNA, long dsRNA, and/or "intermediate" dsRNA (lengths of 100 to 1000 bases or basepairs in complementarity region). It is specifically contemplated that a dsRNA may be a molecule comprising two separate RNA strands in which one strand has at least one region complementary to a region on the other strand. Alternatively, a dsRNA includes a molecule that is single stranded yet has at least one complementarity region as described above (see Sui et al., 2002 and Brummelkamp et al., 2002 in which a single strand with a hairpin loop is used as a dsRNA for RNAi). For convenience, lengths of dsRNA may be referred to in terms of bases, which simply refers to the length of a single strand or in terms of basepairs, which refers to the length of the complementarity region. It is specifically contemplated that embodiments discussed herein with respect to a dsRNA comprised of two strands are contemplated for use with respect to a dsRNA comprising a single strand, and vice versa. In a two-stranded dsRNA molecule, the strand that has a sequence that is complementary to the targeted mRNA is referred to as the "antisense strand" and the strand with a sequence identical to the targeted mRNA is referred to as the "sense strand." Similarly, with a dsRNA comprising only a single strand, it is contemplated that the "antisense region" has the sequence complementary to the targeted mRNA, while the "sense region" has the sequence identical to the targeted mRNA. Furthermore, it will be understood that sense and antisense region, like sense and antisense strands, are complementary (i.e., can specifically hybridize) to each other.

The single RNA strand or two complementary double strands of a dsRNA molecule may be of at least or at most the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 31, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 or more (including the full-length of a particular's gene's mRNA without the poly-A tail) bases or basepairs. If the dsRNA is composed of two separate strands, the two strands may be the same length or different lengths. If the dsRNA is a single strand, in addition to the complementarity region, the strand may have 1, 2, 3, 4, 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more bases on either or both ends (5' and/or 3') or as forming a hairpin loop between the complementarity regions.

In some embodiments, the strand or strands of dsRNA are 100 bases (or basepairs) or less, in which case they may also be referred to as "siRNA." In specific embodiments the strand or strands of the dsRNA are less than 70 bases in length. With respect to those embodiments, the dsRNA strand or strands may be from 5-70, 10-65, 20-60, 30-55, 40-50 bases or basepairs in length. A dsRNA that has a complementarity region equal to or less than 30 basepairs (such as a single stranded hairpin RNA in which the stem or complementary portion is less than or equal to 30 basepairs) or one in which the strands are 30 bases or fewer in length is specifically contemplated, as such molecules evade a mammalian's cell antiviral response. Thus, a hairpin dsRNA (one strand) may be 70 or fewer bases in length with a complementary region of 30 basepairs or fewer. In some cases, a dsRNA may be processed in the cell into siRNA.

Chemically synthesized siRNAs are found to work optimally when they are in cell culture at concentrations of 25-100 nM, but concentrations of about 100 nM have achieved effective suppression of expression in mammalian cells. siRNAs have been most effective in mammalian cell culture at about 100 nM. In several instances, however, lower concentrations of chemically synthesized siRNA have been used (Caplen et al., 2000; Elbashir et al., 2001).

PCT publications WO 99/32619 and WO 01/68836 suggest that RNA for use in siRNA may be chemically or enzymatically synthesized. Both of these texts are incorporated herein in their entirety by reference. The contemplated constructs provide templates that produce RNAs that contain nucleotide sequences identical to a portion of the target gene. Typically the length of identical sequences provided is at least 25 bases, and may be as many as 400 or more bases in length. Longer dsRNAs may be digested to 21-25mer lengths with endogenous nuclease complex that converts long dsRNAs to siRNAs in vivo. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. U.S. Pat. No. 5,795,715 reports the simultaneous transcription of two complementary DNA sequence strands in a single reaction mixture, wherein the two transcripts are immediately hybridized.

2. Vectors

Vectors of the present invention are designed, primarily, to transform cells with a therapeutic or preventative PBEF inhibitor encoding a PBEF inhibitor nucleic acid sequence under the control of a eukaryotic promoter (i.e., constitutive, inducible, repressable, tissue specific). Also, the vectors may contain a selectable marker if, for no other reason, to facilitate their manipulation in vitro. However, selectable markers may play an important role in producing recombinant cells.

The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation.

The term "promoter" will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

In some embodiments, the promoter for use in the present invention is the cytomegalovirus (CMV) immediate early (IE) promoter. This promoter is commercially available from Invitrogen in the vector pcDNAIII, which is some for use in the present invention. Other viral promoters, cellular promoters/enhancers and inducible promoters/enhancers may be used in combination with the present invention. Additionally any promoter/enhancer combination (as per the Eukaryotic Promoter Data Base EPDB) could also be used to drive expression of a nucleic acid of interest.

Another signal that may prove useful is a polyadenylation signal. Such signals may be obtained from the human growth hormone (hGH) gene, the bovine growth hormone (BGH) gene, or SV40.

The use of internal ribosome binding sites (IRES) elements are used to create multigene, or polycistronic, messages. IRES elements are able to bypass the ribosome scanning model of 5-methylated cap-dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

In any event, it will be understood that promoters are DNA elements which when positioned functionally upstream of a gene leads to the expression of that gene. Most transgene constructs of the present invention are functionally positioned downstream of a promoter element.

Compositions and methods of the invention are provided for administering the compositions of the invention to a patient.

Any nucleic acid molecule of the invention may be comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., (2001) and Ausubel et al., 1996, both incorporated herein by reference. In addition to encoding a modified polypeptide such as modified gelonin, a vector may encode non-modified polypeptide sequences such as a tag or targeting molecule. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage. A targeting molecule is one that directs the modified polypeptide to a particular organ, tissue, cell, or other location in a subject's body.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

One method for delivery of the recombinant DNA involves the use of an adenovirus expression vector. "Adenovirus expression vector" is meant to include those constructs containing adenovirus sequences sufficient to (a) support packaging of the construct and (b) to ultimately express a recombinant gene construct that has been cloned therein. The adenovirus vector may be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the some starting material in order to obtain the conditional replication-defective adenovirus vector for use in the present invention. As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

The retroviruses are a group of single-stranded RNA viruses characterized by an ability to convert their RNA to double-stranded DNA in infected cells by a process of reverse-transcription (Coffin, 1990). In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Other viral vectors include adeno-associated virus (AAV) (described in U.S. Pat. No. 5,139,941 and U.S. Pat. No. 4,797,368, each incorporated herein by reference), vaccinia virus, other poxviruses, lentivirus, Epstein Barr viruses, and picornaviruses.

3. Protamine Delivery of Nucleic Acids

Protamine may also be used to form a complex with an expression construct. Such complexes may then be formulated with the lipid compositions described above for administration to a cell. Protamines are small highly basic nucleoproteins associated with DNA. Their use in the delivery of nucleic acids is described in U.S. Pat. No. 5,187,260, which is incorporated by reference.

4. Lipid Formulations for Nucleic Acid Delivery

In a further embodiment of the invention, a nucleic acid may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL).

Advances in lipid formulations have improved the efficiency of gene transfer in vivo (Smyth-Templeton et al., 1997; WO 98/07408). A novel lipid formulation composed of an equimolar ratio of 1,2-bis(oleoyloxy)-3-(trimethyl ammonio) propane (DOTAP) and cholesterol significantly enhances systemic in vivo gene transfer, approximately 150-fold. The DOTAP:cholesterol lipid formulation is said to form a unique structure termed a "sandwich liposome". This formulation is reported to "sandwich" DNA between an invaginated bi-layer or 'vase' structure. Beneficial characteristics of these lipid structures include a positive colloidal stabilization by cholesterol, two dimensional DNA packing and increased serum stability.

In further embodiments, the liposome is further defined as a nanoparticle. A "nanoparticle" is defined herein to refer to a submicron particle. The submicron particle can be of any size. For example, the nanoparticle may have a diameter of from about 0.1, 1, 10, 100, 300, 500, 700, 1000 nanometers or greater. The nanoparticles that are administered to a subject may be of more than one size.

Any method known to those of ordinary skill in the art can be used to produce nanoparticles. In some embodiments, the nanoparticles are extruded during the production process. Information pertaining to the production of nanoparticles can be found in U.S. Patent App. Pub. No. 20050143336, U.S. Patent App. Pub. No. 20030223938, U.S. Patent App. Pub. No. 20030147966, each of which is herein specifically incorporated by reference into this section.

In certain embodiments, an anti-inflammatory agent is administered with the lipid to prevent or reduce inflammation secondary to administration of a lipid:nucleic acid complex. For example, the anti-inflammatory agent may be a non-steroidal anti-inflammatory agent, a salicylate, an anti-rheumatic agent, a steroid, or an immunosuppressive agent.

Synthesis of DOTAP:Chol nanoparticles is by any method known to those of ordinary skill in the art. For example, the method can be in accordance with that set forth in Chada et al., 2003, or Templeton et al., 1997, both of which are herein specifically incorporated by reference. DOTAP:Chol-DNA complexes were prepared fresh two to three hours prior to injection in mice.

One of ordinary skill in the art would be familiar with use of liposomes or lipid formulation to entrap nucleic acid sequences. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL).

Lipid-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of lipid-mediated delivery and expression of foreign DNA in cultured chick embryo, HeLa and hepatoma cells.

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use subcutaneous, intradermal, intratumoral, or intracranial injection to avoid the toxicity and stability problems associated with cationic lipids in the circulation. The interaction of liposomes and plasma proteins is responsible for the disparity between the efficiency of in vitro (Feigner et al., 1987) and in vivo gene transfer (Zhu et al., 1993; Solodin et al., 1995; Liu et al., 1995; Thierry et al., 1995; Tsukamoto et al., 1995; Aksentijevich et al., 1996).

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Liposomal encapsulation has resulted in a lower toxicity and a longer serum half-life for such compounds (Gabizon et al., 1990). Numerous disease treatments are using lipid based gene transfer strategies to enhance conventional or establish novel therapies, in particular therapies for treating hyperproliferative diseases.

The liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1.

A nucleic acid for nonviral delivery may be purified on polyacrylamide gels, cesium chloride centrifugation gradients, column chromatography or by any other means known to one of ordinary skill in the art (see for example, Sambrook et al., 2001, incorporated herein by reference). In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, bulk of cellular components or in vitro reaction components, and/or the bulk of the total genomic and transcribed nucleic acids of one or more cells. Methods for isolating nucleic acids (e.g., equilibrium density centrifugation, electrophoretic separation, column chromatography) are well known to those of skill in the art.

C. Proteins and Polypeptides

The present invention is directed to methods and compositions involving a PBEF inhibitor that is a polypeptide. In certain embodiments, the PBEF polypeptide inhibitors are used in the treatment or prevention of inflammatory conditions or diseases, such as ALI, ARDS, or VILI. The terms "protein" and "polypeptide" are used interchangeably herein and they both cover what is understood as a "peptide" (a polypeptide molecule having 100 or fewer amino acid residues). In certain embodiments of the present invention, the PBEF inhibitor is a protein, polypeptide, or peptide; in particular embodiments, the PBEF inhibitor is protein or polypeptide that is an antibody.

As will be understood by those of skill in the art, modification and changes may be made in the structure of a PBEF inhibitor polypeptide or peptide, and still produce a molecule having like or otherwise desirable characteristics. For example, certain amino acids may be substituted for other amino acids or include deletions, additions, or truncations in the protein sequence without appreciable loss of interactive binding capacity with structures. Since it is the interactive capacity and nature of a protein that defines that protein's biological functional activity, certain amino acid sequence substitutions can be made in a protein sequence (or, of course, its underlying DNA coding sequence) and nevertheless obtain a protein with similar inhibitory properties. It is thus contemplated by the inventors that various changes may be made in the sequence of PBEF inhibitor polypeptides or peptides (or underlying DNA) without appreciable loss of their biological utility or activity.

It is also well understood that where certain residues are shown to be particularly important to the biological or structural properties of a protein or peptide, e.g., residues in the binding site of an antibody, such residues may not generally be exchanged.

Amino acid substitutions are generally based on the relative similarity of the amino acid side-chain substituents, for example, their hydrophobicity, hydrophilicity, charge, size, and the like. An analysis of the size, shape, and type of the amino acid side-chain substituents reveals that arginine, lysine, and histidine are all positively charged residues; that alanine, glycine, and serine are all a similar size; and that phenylalanine, tryptophan, and tyrosine all have a generally similar shape. Therefore, based upon these considerations, the following subsets are defined herein as biologically functional equivalents: arginine, lysine, and histidine; alanine, glycine, and serine; and phenylalanine, tryptophan, and tyrosine.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, some, and those within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2, ±1, or ±0.5 is contemplated.

While discussion has focused on functionally equivalent polypeptides arising from amino acid changes, it will be appreciated that these changes may be effected by alteration of the encoding DNA, taking into consideration also that the genetic code is degenerate and that two or more codons may encode the same amino acid.

1. In Vitro Protein Production

In addition to the purification methods provided in the examples, general procedures for in vitro protein production are discussed. Following transduction with a viral vector according to some embodiments of the present invention, primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshney, 1992).

One embodiment of the foregoing involves the use of gene transfer to immortalize cells for the production and/or presentation of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Another embodiment of the present invention uses autologous B lymphocyte cell lines, which are transfected with a viral vector that expresses an immunogen product, and more specifically, a protein having immunogenic activity. Other examples of mammalian host cell lines include Vero and HeLa cells, other B- and T-cell lines, such as CEM, 721.221, H9, Jurkat, Raji, etc., as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection: for dhfr, which confers resistance to; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

2. Antibody Production

Some embodiments of the present invention pertain to methods and compositions involving an inhibitor of PBEF, wherein the inhibitor is an antibody that binds PBEF.

As used herein, the term "antibody" refers to any form of antibody or fragment thereof that exhibits the desired biological activity. Thus, it is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. An antibody inhibitor may be considered a neutralizing antibody.

Included within the definition of an antibody that binds PBEF is a PBEF antibody binding fragment. As used herein, the term "PBEF binding fragment" or "binding fragment thereof" encompasses a fragment or a derivative of an antibody that still substantially retain its biological activity of inhibiting PBEF activity. Therefore, the term "antibody fragment" or PBEF binding fragment refers to a portion of a full length antibody, generally the antigen binding or variable region thereof. Examples of antibody fragments include Fab, Fab', F(ab').sub.2, and Fv fragments; diabodies; linear antibodies; single-chain antibody molecules, e.g., sc-Fv; and multispecific antibodies formed from antibody fragments. Typically, a binding fragment or derivative retains at least 50% of its PBEF inhibitory activity. Preferably, a binding fragment or derivative retains about or at least about 60%, 70%, 80%, 90%, 95%, 99% or 100% of its PBEF inhibitory activity. It is also intended that a PBEF binding fragment can include conservative amino acid substitutions that do not substantially alter its biologic activity.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975), or may be made by recombinant DNA methods (see, e.g., U.S. Pat. No. 4,816,567). The "monoclonal antibodies" may also be isolated from phage antibody libraries using the techniques described in Clackson et al. (1991) and Marks et al. (1991), for example.

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Any suitable method for generating monoclonal antibodies may be used. For example, a recipient may be immunized with PBEF or a fragment thereof. Any suitable method of immunization can be used. Such methods can include adjuvants, other immunostimulants, repeated booster immunizations, and the use of one or more immunization routes.

Any suitable source of PBEF can be used as the immunogen for the generation of the non-human antibody of the compositions and methods disclosed herein. Such forms include, but are not limited whole protein, peptide(s), and epitopes, generated through recombinant, synthetic, chemical or enzymatic degradation means known in the art.

Any form of the antigen can be used to generate the antibody that is sufficient to generate a biologically active antibody. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids.

D. Small Molecules

The present invention concerns PBEF inhibitors that are small molecules, which refers to a small compound that is biologically active but is not a polymer. It does refer to a monomer. In certain embodiments, the small molecule is FK-866, which is a nicotinamide adenine dinucleotide biosynthesis inhibitor (Holen et al., 2008, which is hereby incorporated by reference). It has been employed in the context of tumor therapy.

FK-866 has an IC50 of about 1 nM in vitro (Hasmann and Schemainda 2003). In in vivo studies by others FK-866 was administered orally twice daily at doses of 6 and 10 mg/kg or twice daily at doses of 3 and 5 mg/kg on days 14 to 19 after tumor cell inoculation. Significant antitumor efficacy was observed for doses of > or =10 mg/kg FK-866 only. In another study, FK-866 was administered twice daily on days 10 to 15 after intrarenal inoculation of RENCA cells in syngenic Balb/c mice at oral doses of 6, 10, 14 and 18 mg/kg to define the optimal dose related to toxicity. For efficacy studies, FK-866 was administered orally twice daily at doses of 6 and 10 mg/kg or twice daily at doses of 3 and 5 mg/kg on days 14 to 19 after tumor cell inoculation. Animals in the positive control group were given 30 mg/kg TNP 470 subcutaneously on every other day beginning on day 1. On day 17, all animals were examined for blood flow in the left renal artery by color Doppler imaging (CDI). Doses of up to 6 mg/kg FK-866 were less toxic than treatment with TNP-470.

E. Formulations and Modes of Administration

The present invention concerns substances that can be used to prevent or treat conditions or diseases. In particular, the present invention concerns PBEF inhibitors as preventative and therapeutic agents. Methods may be employed with respect to individuals who have been diagnosed with a particular inflammatory condition or disease or who are deemed to be at risk for an inflammatory condition or disease.

It is contemplated that compositions of the invention may be administered to a patient within about 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, and/or 1, 2, 3, 4, 5, 6, 7, 8, 9, 10, 11, 12 months of being diagnosed with a inflammatory condition or disease, identified as having symptoms of an inflammatory condition or disease, or identified as at risk for an inflammatory condition or disease.

In certain embodiments, a course of treatment will last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days or more. It is contemplated that one agent may be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, any combination thereof, and another agent is given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, or any combination thereof. Within a single day (24-hour period), the patient may be given one or multiple administrations of the agent(s). Moreover, after a course of treatment, it is contemplated that there is a period of time at which no other treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

In particular embodiments, compositions may be administered 1, 2, 3, 4, 5, 6, 7, 8, 9, 10, 11, 12, 13, 14, 15, 16, 17, 18, 19, 20 or more times, and/or they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months, or any range or combination derivable therein.

Compounds and compositions may be administered to a patient intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, directly, topically, locally, by inhalation, by injection, by infusion, by continuous infusion, by localized perfusion bathing target cells directly, via a catheter, via nebulizer, via aerosol, or via a lavage. In certain embodiments, inflamed tissue is directly administered a PBEF inhibitor.

In certain embodiments, the composition is administered intravenously or intratracheally. Examples of other routes of administration include intravitreal administration, intralesional administration, intratumoral administration, topical administration to the surface of the eye, topical application to the surface of a tumor, direct application to a neovascular membrane, subconjunctival administration, periocular administration, retrobulbar administration, subtenon administration, intracameral administration, subretinal administration, posterior juxtascleral administration, and suprachoroidal administration.

In some embodiments, pharmaceutical compositions are administered to a subject. Different aspects of the present invention involve administering an effective amount of a composition to a subject. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration (which may include enterically coated formulations); time release capsules; and any other form currently used, including inhalants and the like.

The active compounds of the present invention can be formulated for parenteral administration, e.g., formulated for injection via the intravenous, intramuscular, subcutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. A solution may be 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9% or more of the PBEF inhibitor, or any range derivable therein.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Such compositions would normally be administered as pharmaceutically acceptable compositions that include physiologically acceptable carriers, buffers or other excipients. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion, (see for example, Remington's Pharmaceutical Sciences, 1990). Some variation in dosage will necessarily occur depending on the condition of the subject. The person responsible for administration will, in any event, determine the appropriate dose for the individual subject.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

F. Diagnostic Methods

A patient whose cells that express a higher than normal amount of PBEF and/or a sequence corresponding to BC018473 (referred to as "human BC018473") is indicative of a patient with an inflammatory disease or condition. It is contemplated that one or more standards may be generated in which a normal level of PBEF or the human BC018473 expression is defined or identified. That standard may then be referred to as a way of determining whether expression in a given patient is normal or above-normal. The type of standard generated will depend upon the assay or test employed to evaluate expression. In some embodiments of the invention, a score is assigned to a sample based on certain criteria and numbers within or above a certain number or range are deemed "above normal." In preferred embodiments, PBEF or human BC018473 expression is considered above normal if an assay indicates that a particular measurement, amount or level is at about or at most about 50%, 60%, 70%, 80%, 90%, 100%, 150%, 200%, 250%, 300%, 400%, 500%, 600%, 700%, 800%, 900% or above of the measurement, amount or level observed in cells that have normal levels of PBEF or human BC018473 expression. In other words, for example, a cell with normal expression exhibit a level of transcripts that is x; the sample from the patient being tested may be 2.5x, in which case, in some embodiments that patient may be considered to have a below normal level of transcript and thus an above normal level of expression. Alternatively, in some embodiments, expression is considered above normal if an assay indicates that a particular measurement, amount or level is about or at least about 1, 2, 3, 4, 5, 6, 7, 8, 9, 10 or more standard deviations above the measurement, amount or level observed in cells that have normal levels of expression. In other cases, expression may be considered above normal if a measurement, amount or level indicative of expression is or is at most 2, 3, 4, 5, 6, 7, 8, 9, 10, 15, 20, 25, 30, 35, 40, 45, 50 or more times greater than the measurement, amount, or level indicative of expression in normal cells.

Methods of the invention that involve evaluating the expression of PBEF and/or human BC018473 in cells can be achieved by a number of ways that directly or indirectly provide information regarding their expression. Thus, ways of evaluating expression include, but are not limited to, assessing or measuring the corresponding protein, assessing or measuring the corresponding transcript, sequencing the corresponding transcript or genomic sequence, and assaying PBEF activity.

In some embodiments of the invention, methods involve evaluating expression in cells by assessing protein or transcript levels. The term "assessing" is used according to its ordinary and plain meaning to refer to "determining the extent of." In certain embodiments, the level of protein or transcript is assessed by assaying (measuring) the amount of protein, transcript, or gene copy in the cells. In specific aspects of the invention, expression is evaluated by assessing PBEF protein. An anti-PBEF antibody can be used in some cases to assess PBEF protein. Such methods may involve using immunohistochemistry, Western blotting, ELISA, immunoprecipitation, or an antibody array. In particular embodiments, protein is assessed using immunohistochemistry. The use of immunohistochemistry allows for quantitation and characterization of protein. It also allows an immunoreactive score for the sample to be determined. The term "immunoreactive score" (IRS) refers to a number that is calculated based on a scale reflecting the percentage of positive cells (on a scale of 1-4, where 0=0%, 1=<10%, 2=10%-50%, 3=>50%-80%, and 4=>80%) multiplied by the intensity of staining (on a scale of 1-3, where 1=weak, 2=moderate, and 3=strong). Immunoreactive scores range from 0-12.

In some embodiments of the invention, expression is evaluated by assessing transcription. Transcription can be assessed by a variety of methods including those that involve amplifying transcripts or performing Northern blotting on transcripts. Amplification of transcripts can be utilized in quantitative polymerase chain reactions, which are well known to those of ordinary skill in the art. Alternatively, nuclease protection assays may be implemented to quantify transcripts. Other methods that take advantage of hybridization between a probe and target are also contemplated, such as fluorescence in situ hybridization (FISH) and RNA in situ hybridization (RISH). In an another embodiment of the invention, RNA expression is measured using microarrays which can be manufactured containing either global genomic sequence content or disease-specific biomarkers.

Further embodiments of the invention involve evaluating expression by assaying the level of PBEF activity.

It is contemplated that levels are assayed from a sample from the patient. In embodiments of the invention a sample from a patient refers to a biological sample, which includes, but is not limited to a tissue biopsy or section, blood sample, lavage, swab, scrape, nipple aspirate, or other composition that may be extracted from the body and that contains cells. In particular embodiments, the present invention concerns a sample that contains all or part of a tissue biopsy. In further embodiments, the sample contains all or part of a lung tissue biopsy, which may be from a bilateral biopsy or a unilateral biopsy.

The present invention concerns polynucleotides and oligonucleotides, isolatable from cells, that are free from total genomic DNA and that are capable of expressing all or part of a protein or polypeptide. The polynucleotides or oligonucleotides may be identical or complementary to all or part of a nucleic acid sequence encoding PBEF or human BC018473. These nucleic acids may be used directly or indirectly to assess, evaluate, quantify, or determine expression.

As used in this application, the term "PBEF polynucleotide" refers to a PBEF-encoding nucleic acid molecule that has been isolated essentially or substantially free of total genomic nucleic acid to permit hybridization and amplification, but is not limited to such. Therefore, a "polynucleotide encoding PBEF" refers to a DNA segment that contains wild-type (SEQ ID NO:1) PBEF-coding sequences isolated away from, or purified free from, total mammalian or human genomic DNA. A PBEF oligonucleotide refers to a nucleic acid molecule that is complementary or identical to at least 5 contiguous nucleotides of a PBEF-encoding sequence, such as SEQ ID NO:1, which is the cDNA sequence encoding human PBEF. Similarly, a BC018473 polynucleotide refers to the sequence of SEQ ID NO:3, which may be used in embodiments of the invention to detect expression of human BC018473 in cells.

A nucleic acid encoding all or part of a PBEF or BC018473 sequence is contemplated for use with the present invention. In certain embodiments there is a nucleic acid that is identical or complementary to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more contiguous nucleotides, nucleosides, or base pairs (or any range derivable therein), including such sequences from SEQ ID NO:1 or SEQ ID NOs:3-9 (which means SEQ ID NO:3, SEQ ID NO:4, SEQ ID NO:5, SEQ ID NO:6, SEQ ID NO:7, SEQ ID NO:8, or SEQ ID NO:9).

The various probes and primers designed around the nucleotide sequences of the present invention may be of any length, such as described above. By assigning numeric values to a sequence, for example, the first residue is 1, the second residue is 2, etc., an algorithm defining all primers can be proposed: n to n+y, where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Such probes or primers can be of lengths described above from SEQ ID NO:1 or SEQ ID NOs:3-9. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Probes may be complementary (also referred to as "complementarity") or identical to at least or at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous bases, or any range derivable therein, of sequences (or their complements) disclosed herein. In some embodiments, the sequence is any of SEQ ID NO:1 or SEQ ID NOs:3-9.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

Nucleic acids used as a template for amplification may be isolated from cells, tissues or other samples according to standard methodologies (Sambrook et al., 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to a nucleic acid corresponding to SEQ ID NO:1 or SEQ ID NOs:3-9 are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 2001). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety. Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention. PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

Following any amplification or step such as primer extension, it may be desirable to separate the amplification or primer extension product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

Reverse transcription (RT) of RNA to cDNA followed by relative quantitative PCR™ (RT-PCR) can be used to determine the relative concentrations of specific mRNA species isolated from a cell, such as a PBEF or BC018473-encoding transcript. By determining that the concentration of a specific mRNA species varies, it is shown that the gene encoding the specific mRNA species is differentially expressed.

Specifically contemplated are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al., 1991). It is contemplated that this technology may be used in conjunction with evaluating the expression level of PBEF and/or human BC018473 with respect to diagnostic methods of the invention.

G. Screening Methods

The present invention further comprises methods for identifying PBEF inhibitors. These assays may comprise random screening of large libraries of candidate substances; alternatively, the assays may be used to focus on particular classes of compounds selected with an eye towards structural attributes that are believed to make them more likely to modulate the function of PBEF.

By function, it is meant that one may assay for a measurable effect on PBEF activity. To identify a PBEF inhibitor, one generally will determine the activity or level of inhibition of Fortilin in the presence and absence of the candidate substance, wherein a modulator is defined as any substance that alters these characteristics. For example, a method generally comprises:

providing a candidate modulator;
admixing the candidate modulator with an isolated compound or cell expressing the compound;
measuring one or more characteristics of the compound or cell in step (b); and
comparing the characteristic measured in step (c) with the characteristic of the compound or cell in the absence of said candidate modulator,
wherein a difference between the measured characteristics indicates that said candidate modulator is, indeed, a modulator of the compound or cell.

Assays may be conducted in cell free systems, in isolated cells, or in organisms including transgenic animals.

It will, of course, be understood that all the screening methods of the present invention are useful in themselves notwithstanding the fact that effective candidates may not be found. The invention provides methods for screening for such candidates, not solely methods of finding them.

As used herein the term "candidate substance" refers to any molecule that may be a "inhibitor" of PBEF, i.e., potentially affect PBEF activity directly.

The candidate substance may be a protein or fragment thereof, a small molecule, or even a nucleic acid molecule. An example of pharmacological compounds will be compounds that are structurally related to PBEF, or a molecule that binds PBEF such as an antibody. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are well known to those of skill in the art. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Materials and Methods for Examples 3-10

Transmigration and Chemotaxis Assay.

Chemotaxis of rat peritoneal neutrophils (calcein-AM) across 3 μm polycarbonate filters was assessed in response to recombinant human PBEF/visfatin (rhPBEF, PeproTech, Rocky Hill, N.J.), or casein (positive control). (See Supplemental Methods for additional details).

Experimental Protocols and Generation of $PBEF^{+/-}$ Transgenic Mice.

C57BL/6J (B6) mice were housed under standard conditions with all procedures approved by the Animal Care and Use Committee (University of Chicago). To generate $PBEF^{+/-}$ mice, the 129/Sv/Ola derived ES cell line (Nichols et al., 1990) RR084 harboring the exon-trap vector pGT0lxf (Ma et al., 2005) in the $7^{th}$ intron of the murine PBEF gene was obtained (BayGenomics Consortium, San Francisco, Calif.). Transgenic mice were produced by microinjection of the ES cells into blastocysts derived from B6 mice, and screened by insertion junction-specific PCR of tail DNA. Founder mice were out-crossed to B6 mice for 4 generations to reach 85% congenic status. All outcrosses to B6 mice were viable; however, in-crosses failed to produce homozygous knockout progeny (see Supplemental Methods).

Models of Ventilator-Induced Murine Lung Injury.

The first VILI model was designed to produce limited lung injury (VILIa, tidal volume 30 ml/kg), thus allowing assessment of potential synergy with rhPBEF challenge. Male C57BL/6J B6 mice were anesthetized with ketamine/acepromazine, intubated and administered rhPBEF (20 μg/mouse) via an intratracheal (IT) route ~30 min before ventilator placement (room air, tidal volume 30 ml/kg, 65 breaths/minute, 0 cm $H_2O$ PEEP) for 4 hr as previously described (Nonas et al., 2007; Moitra et al., 2007). Groups included a spontaneous breathing group (SB), a spontaneous breathing group challenged with rhPBEF (SB-rhPBEF), a high tidal ventilation group (VILIa), and a high tidal ventilation group with rhPBEF challenge (VILIa-rhPBEF) (n=4-6 all groups).

Our second ventilation approach was designed to produce more severe lung injury (VILIb, tidal volume 40 ml/kg) in order to assess potential protective effects of the single PBEF allele deletion in $PBEF^{+/-}$ mice. Transgenic $PBEF^{+/-}$ and wild type ($PBEF^{+/+}$) mice were anesthetized and ventilated (room air, tidal volume 40 ml/kg, 65 breaths/minute, 0 cm $H_2O$ PEEP) for 4 hours and randomly allocated into four groups either spontaneous breathing (SB-WT and SB-$PBEF^{+/-}$ groups), or exposed to high tidal ventilation (VILIb-WT and VILIb-$PBEF^{+/-}$ groups). (See Supplemental Methods).

Bronchoalveolar Lavage (BAL): Tissue Albumin and Cytokine Content.

BAL fluid recovered as we previously described was used for multiple assays including total BAL protein, and BAL cell differentials (Peng et al., 2004). Tissue albumin content was assessed as previously described (Nonas et al., 2007). Cytokine levels in BAL fluid (IL-1β, IL-6, KC, MIP2, TNF-α) were analyzed by multiplex assays (Bio-Rad, Hercules, Calif., USA). BAL PBEF levels were assayed by a C-terminal ELISA (Phoenix Pharmaceuticals Inc. Belmont, Calif.) and analyzed using the SoftmaxPRO software (Molecular Devices Corp). (See Supplemental Methods).

Statistical Analysis for Biomarker Data.

Statistical analysis (mean±SEM) was carried out using SPSS 12.0 with one-way ANOVA tests and post hoc multiple comparisons using Tukey's method. $p<0.05$ was considered significant.

RNA Isolation and Microarray Analysis.

Total lung RNA was isolated as described previously (Nonas et al., 2007). Affymetrix Mouse430_2 arrays (Affymetrix Inc., Santa Clara, Calif.) were utilized. Chip quality (Li and Wong, 2001) and 'present' or 'absent' expression calls were determined by GeneChip® Operating Software (GCOS) (GSE9368-rhPBEF, GSE9314-$PBEF^{+/-}$). Intensities and normalization of probe sets were calculated by Bioconductor software (GCRMA package) (Team RDC, 2005). To identify differentially-expressed genes, pairwise comparisons were conducted using Significance Analysis of Microarrays (SAM) as previously described (Nonas et al., 2007). Gene filtering parameters and results are summarized in Supplementary Table E2. Differentially-expressed genes displaying>2 fold changes are referred to as "dysregulated genes".

Gene Ontology (GO) and Ingenuity Pathways Analysis of Dysregulated Genes.

Dysregulated gene functional profiles were analyzed using Onto-Express with the number of genes in each GO biological process category (Wu et al., 2004) compared with all genes on the Mouse432_2 chip to determine the significance of the GO category (Consortium, 2006). Ingenuity Pathway Analysis (IPA) software (containing individually modeled relationships between gene objects e.g. genes, mRNAs, proteins) was utilized to dynamically generate significant regulatory and signaling networks or pathways. The significance of a canonical pathway is controlled by the p-value calculated using the right-tailed Fisher Exact Test for 2×2 contingency tables. (See Supplemental Methods).

Experiments with PBEF Neutralizing Antibody (PBEF-Ab)

Polyclonal anti-PBEF antibodies were custom produced by Lampire Biological Laboratories, Inc. (Piperville, Pa.) by immunization of a goat with full-length human recombinant PBEF protein. PBEF antibodies were purified over a protein G column to a final concentration of 1.1 mg/ml and used for the in vivo neutralization studies to determine the optimal dose for subsequent experiments in our severe lung injury (VILIb) model. In specific experiments, PBEF-antibody or saline were injected intratracheally (70 µl) and after a 30 min period, mice were ventilated with room air (SB) or VILIb (40 ml/kg, 4 hr).

Example 2

Supplemental Materials and Methods for Examples 3-10

Recombinant Human PBEF.

Recombinant human soluble PBEF/visfatin (rhPBEF), a 52 kDa protein containing 465 amino acid residues was purchased from PeproTech (Rocky Hill, N.J., USA). Purity was more than 98% by SDS-PAGE gel and HPLC analyses, and contained <0.01 ng LPS/µg PBEF as determined by the *Limulus* amebocyte lysate method.

Transmigration and Chemotaxis Assay.

Neutrophils were collected from retired breeder male Harlan-Sprague Dawley rats by intraperitoneal injection of 2.5% casein (5 ml). The resulting peritoneal fluid was recovered by PBS peritoneal lavage after 18 hr, centrifuged and examined for total cell counts and cell differentiation. For chemotaxis assays, leukocytes were exposed to calcein-AM in the presence of plurionic acid for 1 hr at room temperature. The temperature was then elevated to 37° C. for 30 min to cleave the calcein AM thereby reducing the rate of calcein diffusion out of the cells. The resuspended leukocyte suspension was placed above a Millipore Multiscreen-MIC Transwell plate (Billerica, Mass.) with 3 µm polycarbonate filters precoated with 4% bovine albumin. rhPBEF (10 ng/ul) was placed below the filters in the receiving wells of the plate (in PBS) or casein (positive chemoattractant control). The receiving wells were assessed serially in a fluorescent plate reader with absorption at 494 nm and emission measured at 517 nm. Fluorescence was recorded at 5, 10, 15, 30 min and each subsequent 30 min period for up to 4 hr. Aliquots of known numbers of neutrophils were counted in separate wells at each time point to account for any quenching of the fluorescence over time.

Experimental Animal Protocols.

Animal procedures were conducted and approved following the recommendations of the Animal Care and Use Committee at the University of Chicago. C57BL/6J mice were obtained from Jackson Laboratories (Wilmington, Mass.) and housed under standard conditions (12 h light-dark cycle, 25-27° C., ~40% humidity) with free access to food and water throughout the duration of the experiments.

Generation of Transgenic Mice.

The 129/Sv/Ola derived ES cell line (Nichols et al., 1990) RR084 harboring the exon-trap vector pGT0lxf (Ma et al., 2005) in the 7th intron of the murine PBEF gene was obtained from the NHLBI-funded Program In Genomic Applications BayGenomics Consortium (San Francisco, Calif.). Transgenic mice were produced by microinjection of the ES cells into blastocysts derived from B6/J mice, and screened by insertion junction-specific PCR on tail DNA. The gene-specific primers were In7 (forward; 5'-CGGATGCCTTAGCCT-GAAGT-3' SEQ ID NO:7) and VecIn7JR (reverse; 5'-GG-GAGTGACACAGCAAATCA-3' SEQ ID NO:8) giving a 458-bp product. The transgene-specific primer VecIn7JF (forward; 5'-CAGCAGCAGACCATTTTCAA-3' SEQ IN NO:9), in conjunction with the primer VecIn7JR, produced a 284-bp knockout allele-specific product. All reactions were "hot-started" for 3 min at 93° C. using the AmpliTaq™ Gold system (Applied Biosystems, Foster City, Calif.) including 1.5 mM $MgCl_2$, 500 µM dNTPs, and 200 nM of each primer, followed by 30 cycles of 15 sec at 94° C., 30 sec at 55° C., and 60 sec at 72° C. Founder mice were out-crossed to B6 mice for 4 generations to reach 85% congenic status. Five transgenic founders were obtained from 10 live births, of which 3 transmitted the transgene to the next generation. All outcrosses to B6 mice were viable, but none of the in-crosses were able to produce progeny homozygous for both knockout alleles. Mice derived from one founder (C10), hemizygous for the exon-trapped allele at $N_4$ backcross generation, are characterized in this report.

Ventilator-Induced Murine Lung Injury Models.

We utilized two experimental models of ventilator-induce lung injury in these experiments. Our first approach (VILIa) utilized a VILI protocol with a tidal volume of 30 ml/kg designed to produce limited lung injury in order to allow assessment of potential synergism between delivered PBEF and mechanical ventilation-induced lung injury. Male C57BL/6J mice (8-12 wk old, 24.7±2.0 g) were weighed, anesthetized with ketamine/acepromazine, intubated using a 20 gauge catheter (Medex, Inc, Carlsbad, Calif.) and administered recombinant PBEF (20 µg/mouse in 1.5 µl water per gram body weight or vehicle equal volumes of water) via an intratracheal (IT) route ~30 min before being placed on mechanical ventilation as we have previously described (Peng et al., 2004). Mice were then connected to Harvard Apparatus ventilator (Boston, Mass.) at room air, tidal volume of 30 ml/kg, 65 breaths/minute, and positive expiratory pressure (PEEP) 0 cm $H_2O$ for 4 hr. Groups of mice were randomly allocated to either the spontaneous breathing group (SB) (n=4), the spontaneous breathing challenged with IT rhPBEF group (SB-rhPBEF) (n=6), the high tidal ventilation group (VILIa) (n=6), or high tidal ventilation with rhPBEF group (VILIa-rhPBEF) (n=6). Normal saline (0.2 cc) was given via intraperitoneal injection at the beginning and 2 hours later to all ventilated mice and peak inspiratory pressure was monitored continuously. Temperature was maintained with heat blanket to all mice during experiment.

In a separate set of experiments, our second approach utilized a VILI protocol employing a greater tidal volume (40 ml/kg) designed to produce more severe lung injury (VILIb) in order to assess potential protective effects of the single PBEF allele deletion in PBEF$^{+/-}$ mice on a B6/J murine background. PBEF transgenic mice (PBEF$^{+/-}$) and wild type controls (PBEF$^{+/+}$) at 18-22 week old (20-29 g) were anesthetized and ventilated at room air, tidal volume of 40 ml/kg at 65 breaths/minute with PEEP 0 cm H$_2$O for 4 hours. Wild type or PBEF$^{+/-}$ mice were randomly allocated into four groups and exposed to either spontaneous breathing, (SB-PBEF$^{+/+}$ and SB-PBEF$^{+/-}$), or to high tidal ventilation (VILIb-WT and VILIb-PBEF$^{+/-}$).

Bronchoalveolar Lavage.

Mice underwent bronchioalveolar lavage (BAL) of both lungs with Hank's balanced salt solution (1 mL/mouse), and the recovered BAL fluid was used for assays as we have previously described (Peng et al., 2004). Total protein was measured using the Bio-Rad DC Protein Assay (Bio-Rad Laboratories, Hercules, Calif.) (Peng et al., 2004). Protein results were expressed as mg/ml to allow for comparison to other studies. Lavage samples were centrifuged at 500×g on a refrigerated micro centrifuge for 20 min. The supernatant was decanted and aliquot for protein assays. The BAL cells were resuspended in Hank's balanced salt solution and counted using a hemacytometer using standard techniques.

Cytospin and Differential Counting.

Re-suspended BAL cells from lung lavage were centrifuged using a Shandon Cytospin-2 at 600 RPM for 15 min, fixed by air-drying, and stained with Diff-Quik dye for differential counts (Peng et al., 2004). Stained cell slides were evaluated and differentially counted for each individual animal (lymphocyte, neutrophil or a macrophage).

Cytokine Assays:

BAL fluid for cytokine measurements was stored at −80° C. until analysis. A multiplex cytokine kit for IL-1-β, IL-6, KC, macrophage inflammatory protein-2 (MIP2) and tumor necrosis factor alpha (TNF-α) was obtained and the assay performed in accordance with manufacturer's instructions (Bio-Rad, Hercules, Calif., USA). Multiplex working solution (50 µl) was placed into each well and the appropriate cytokine standards and samples (50 µl) were added to wells of a filtered plate, and incubated at room temperature for 30 min on a plate shaker (set to 300 rpm) in the dark. Freshly diluted secondary/detection antibody (25 µl/well) was next added to the wells at room temperature for 30 min followed by streptavidin-PE (16 µg/ml in assay buffer). Bound beads were washed three times with 100 µl of wash buffer After the last wash, 125 µl of assay buffer was added to each well, the plate placed for 1 min on a plate shaker set at 500 rpm and then for 3 min at the reduced speed of 300 rpm. Fifty µl of sample was analyzed on the Bio-Plex system (Bio-Rad) in accordance with the manufacturer's instructions. Data analyses for all assays were performed using the Bio-Plex Manager software. Evaluation of BAL PBEF levels was performed by using a C-terminal (human) enzyme-linked immunosorbent assay (ELISA) kit (Phoenix Pharmaceuticals Inc. Belmont, Calif.) with a sensitivity of 1.89 ng/ml. ELISA plates were read using a Spectra MAX (Molecular Devices Corp, Sunnyvale, Calif.) instrument, and data analyzed using the SoftmaxPRO software (Molecular Devices Corp).

RNA Isolation and Microarray Analysis.

Lung total RNA was isolated from whole rodent lung tissue for microarray experiment as we have described previously (9) using the Affymetrix GeneChip platform and Expression Analysis Manual protocols (Affymetrix Inc., Santa Clara, Calif.). The signal intensity fluorescent images produced during Affymetrix GeneChip Mouse430_2 Array hybridizations were scanned using the Hewlett-Packard GeneArray Scanner G2500A. The 'Present' or 'Absent' calls of the probe sets in the expression chips were determined by GCOS (GeneChip® Operating Software) software. The microarray data have been submitted to the National Center for Biotechnology Information (NCBI)'s Gene Expression Omnibus repository (GSE9368 for rhPBEF study and GSE9314 for PBEF$^{+/-}$ study). Chip quality (RNA degradation, cDNA synthesis, hybridization, chip washing, scanning) was evaluated with GCOS, dChip (Li and Wong, 2001) and Bioconductor 'affy' packages. All RNA samples and chips adopted in current study passed the quality criteria (data not shown). The intensities of probe sets were calculated by the GC Robust Multichip Average (GCRMA) package of Bioconductor software for normalization (Team RDC, 2005). To identify differentially-expressed genes, pairwise comparisons were conducted using Significance Analysis of Microarrays (SAM) (see the SAM online manual for detailed explanations of the blocking approach, www-stat.stanford.edu/~tibs/SAM) as we have previously described (Nonas et al., 2007). Only probe sets present (determined by Affy 'P'-call) in three replicates of at least one group with mean intensity above 100 were used for further data mining. The gene filtering parameters and results were summarized in Supplementary Table E2. All differentially-expressed genes displayed at least 2 fold changes and are referred to as "dysregulated genes" when normal control animals are used as reference. For probe sets representing the same Entrez Gene or UniGene ID, only the probe set with lowest FDR or highest fold changes was included in the gene list.

Identification of Gene Ontology (GO) Categories Enriched with Dysregulated Genes.

The functional profiles of dysregulated genes were represented by the biological processes in the GO database with the number of genes in each GO category compared to that of all genes in the Mouse432_2 chip to determine the significance of the GO category. The analysis was performed using Onto-Express (Intelligent Systems and Bioinformatics Laboratory, Wayne State University) (www.geneontology.org/GO.downloads.ontology.shtml), with the default selection of statistical method (hypergeometric distribution followed by false discovery rate correction). The lists of dysregulated genes were uploaded into Onto-Express to identify significant GO categories (q≤S 0.05 with 6 or more genes).

Ingenuity Pathway Analysis (IPA).

Dysregulated genes were uploaded into the IPA software (http://www.ingenuity.com), a web-delivered application which utilizes the Ingenuity Pathways Knowledge Base (IPKB) containing a robust number of individually modeled relationships between gene objects (e.g. genes, mRNAs, proteins), in order to dynamically generate significant regulatory and signaling networks or pathways. The genes submitted for mapping to corresponding gene objects in the IPKB are called "focus genes." The significance of a canonical pathway is controlled by p-value, which is calculated using the right-tailed (referring to the overrepresented pathway) Fisher Exact Test for 2×2 contingency tables. This is done by comparing the number of 'Focus' genes that participate in a given pathway, relative to the total number of occurrences of those genes in all pathways stored in the IPKB. The significance threshold of a canonical pathway is set to 1.3, which is derived by $-\log_{10}$ [p-value], with p value≤0.05.

Generation and Administration of PBEF Neutralizing Antibody (PBEF-Ab)

Polyclonal anti-PBEF antibodies, used in the in vivo neutralization studies, were custom produced by Lampire Biological Laboratories, Inc. (Pipersville, Pa.) by immunization of a goat with full-length human recombinant PBEF protein. Antibodies were purified over a protein G column. 70 μl of PBEFAb or saline were injected intratracheally. After delivery (30 min), mice were ventilated with room air (SB) or VILIb (40 ml/kg, for 4 hours). Boluses of sterile saline (200 μl) were given at the onset and after 2 h of ventilation, to maintain a mean arterial pressure greater than 60 mm Hg. This ventilation strategy maintains the blood gas parameters within a physiologic range (arterial pH of 7.3-7.5, HCO3 11-16 mmol/L) at the end of the experiment.

Example 3

Effect of rhPBEF on Neutrophil Transmigration and Chemotaxis in Vitro

Prior reports have suggested an effect of PBEF gene and protein expression on neutrophil function (Jia et al., 2004). Given the implied pathologic role for PBEF in sepsis, ALI and in preclinical models of mechanical ventilation-induced ALI (Ye et al., 2005), our initial studies were designed to investigate the possibility that PBEF directly serves as a neutrophil chemoattractant (FIG. 1A). Migration of rat peritoneal neutrophils (~90% purity) across Transwell filters in response to lower chamber rhPBEF or casein was assessed for up to 4 hours. PBEF induced significant PMN migration beginning after 2 hrs whereas casein-mediated PMN migration was significant at all time points beginning at 30 minutes (FIG. 1A), results consistent with a physiological role for PBEF as a direct PMN chemoattractant.

Example 4

In Vivo Effects of rhPBEF in Spontaneously Breathing Mice

Figure 1B:
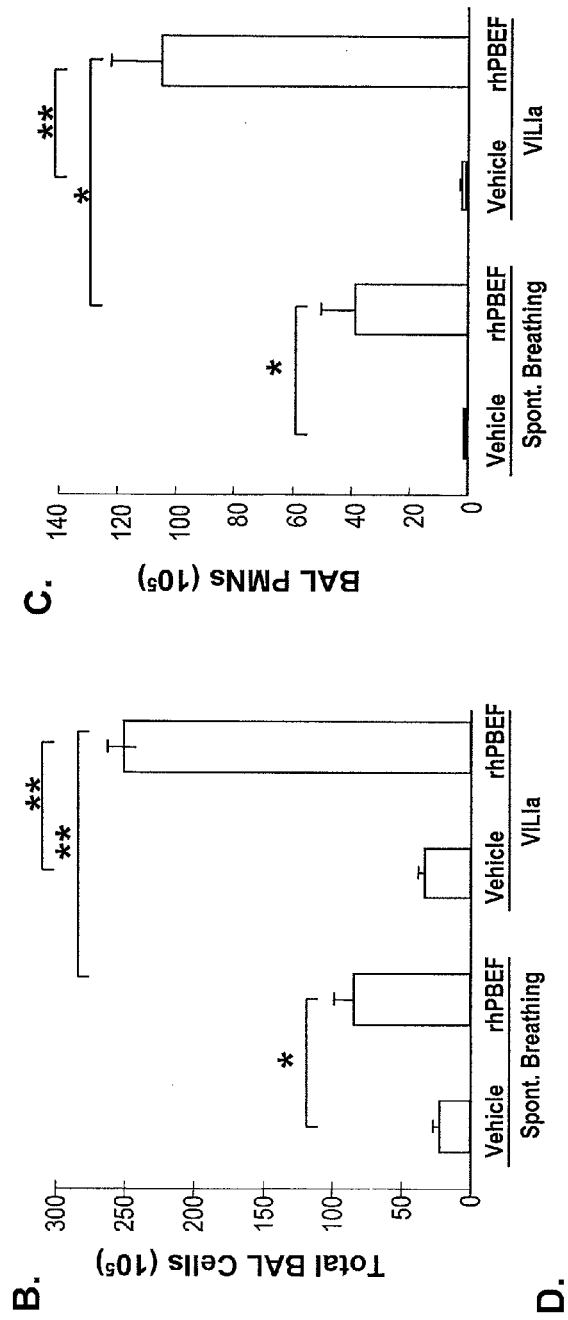
Figure 1C:
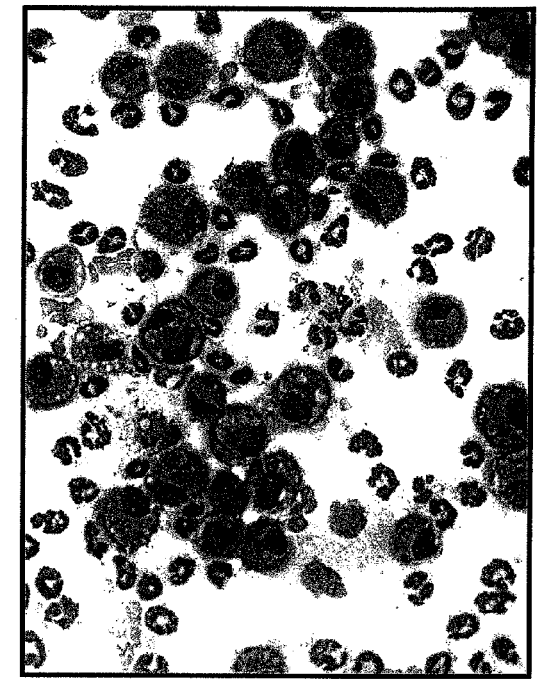
Figure 1D:
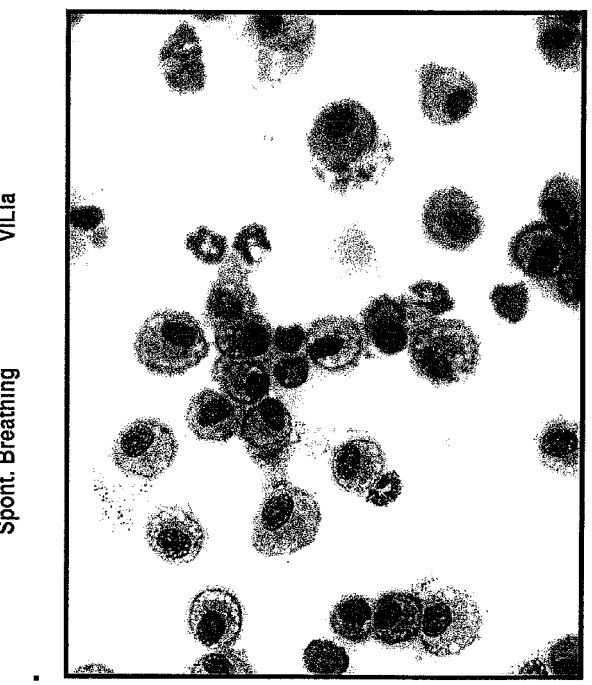
Figure 2A:
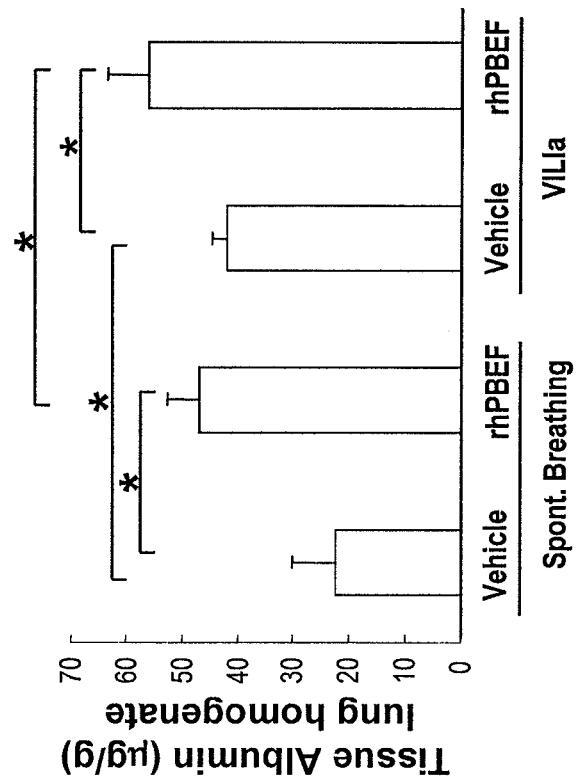
FIG. 2. Effect of rhPBEF on BAL protein levels and lung tissue albumin content in C57BL/6 mice. Instillation of rhPBEF did not produce increased permeability as reflected by BAL protein levels (vehicle 0.17 mg/ml±0.01 vs. rhPBEF 0.17±0.01, p=0.77, Panel A). However, rhPBEF significantly increased lung albumin content (vehicle 22.5 μg/g tissue±7.5 vs. rhPBEF 47.0±5.6, *p=0.03, Panel B), potentially reflecting the temporal course and/or anatomic location of edema formation. In contrast, VILIa (30 ml/kg, 4 hrs) induced significant increases in BAL protein compared to spontaneous breathing (SB) (* * $p<0.001$). In addition, the combined VILIa-rhPBEF challenge induced increases in BAL protein compared to VIIIa and SB-rhPBEF mice (VILIa 0.27 mg/ml±0.02 vs. VILIa-rhPBEF 0.34±0.02, * $p<0.05$, Panel A) (n=4~6 animals each group, all experiments).
Figure 2B:
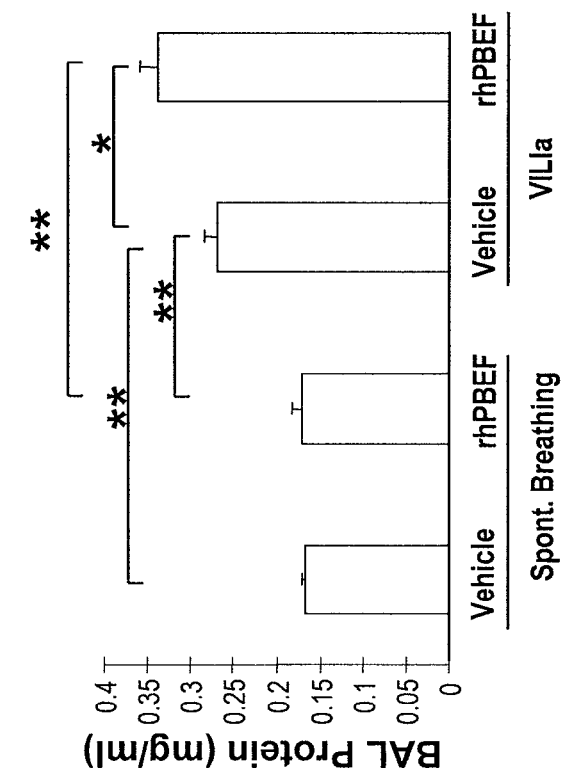
Figures 3A, 3B, 3C:
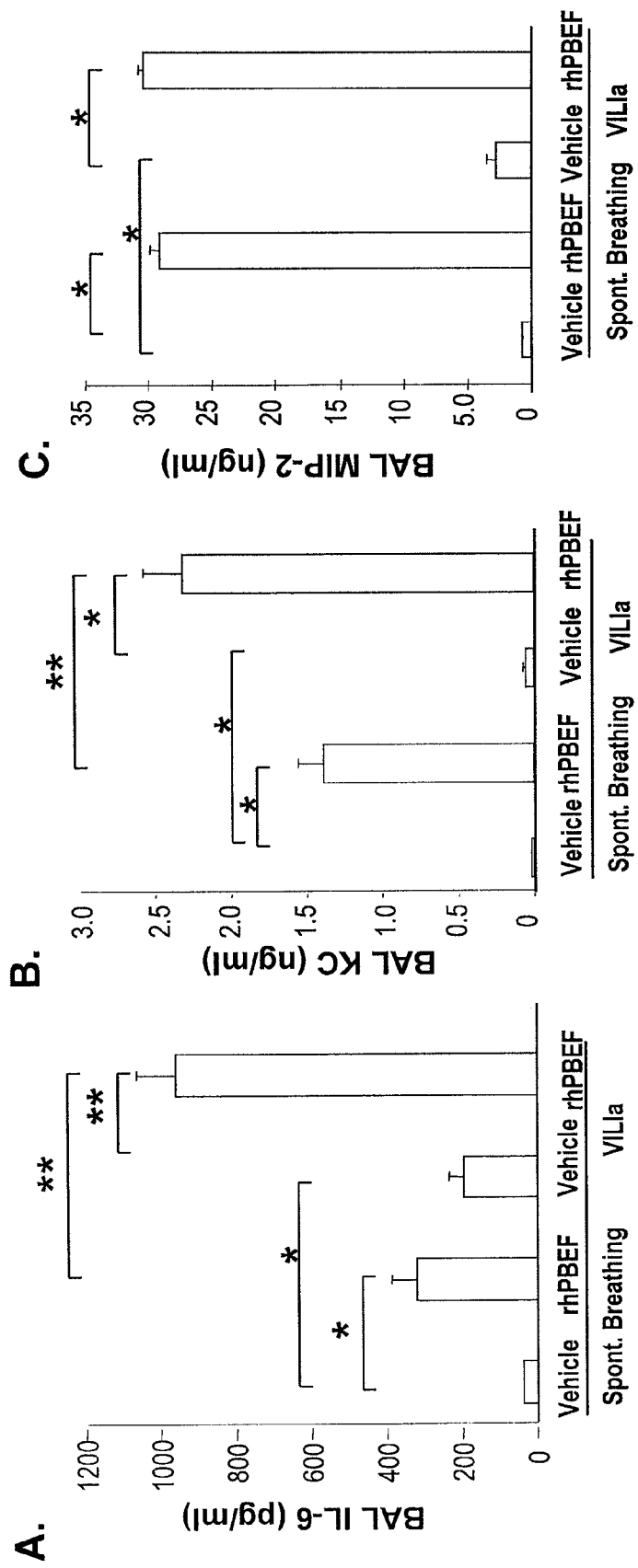
FIG. 3. Effect of rhPBEF on BAL cytokine levels in C57BL/6 mice. The levels of BAL IL-6 (Panel A) were significantly elevated in the rhPBEF group when compared to vehicle group (vehicle 36±4 pg/ml vs. rhPBEF 319±67; * $p<0.01$). In addition, when mice were exposed to rhPBEF followed by mechanical ventilation, the VILIa-rhPBEF group had significantly elevated concentrations of IL-6 (VILIa, 194 pg/ml±38 vs. VILIa-rhPBEF, 957±103, ** $p<0.001$). Similarly, rhPBEF challenge significantly elevated the concentrations of the PMN chemokines KC (vehicle 12 pg/ml±3 vs. rhPBEF 1388±169, * $p<0.001$, Panel B) and MIP-2 (vehicle 676 pg/ml±87 vs. rhPBEF 29026±762, * $p<0.001$, Panel C) compared to the vehicle control group. The levels of KC was substantially elevated in VILIa-rhPBEF (VILIa 58 pg/ml±15 vs. VILIa-rhPBEF 2310±263, **p<0.001). MIP-2 levels were elevated in VILIa-rhPBEF group compared to VILIa (VILIa 2751 pg/ml±821 vs. VILIa-rhPBEF 30480±219, * $p<0.001$). Finally, significantly elevated concentrations of TNF-α (Panel D) in the rhPBEF group were found (SB 17 pg/ml±8 vs. SB-rhPBEF 262±94, * $p<0.05$), as well as the VILIa-rhPBEF group of TNF-α (VILIa 6 pg/ml±2 vs. VILIa-rhPBEF 985±293, * $p<0.05$). Significantly elevated concentrations of IL-1β (Panel E) were also noted in the SB-rhPBEF (SB 18 pg/ml±3 vs. SB-rhPBEF 55±22) and VILIa-rhPBEF groups (VILIa 9 pg/ml±2 vs. VILIa-rhPBEF 53±4, * p=0.01). N=4~6 animals each group.
Figures 3D, 3E:
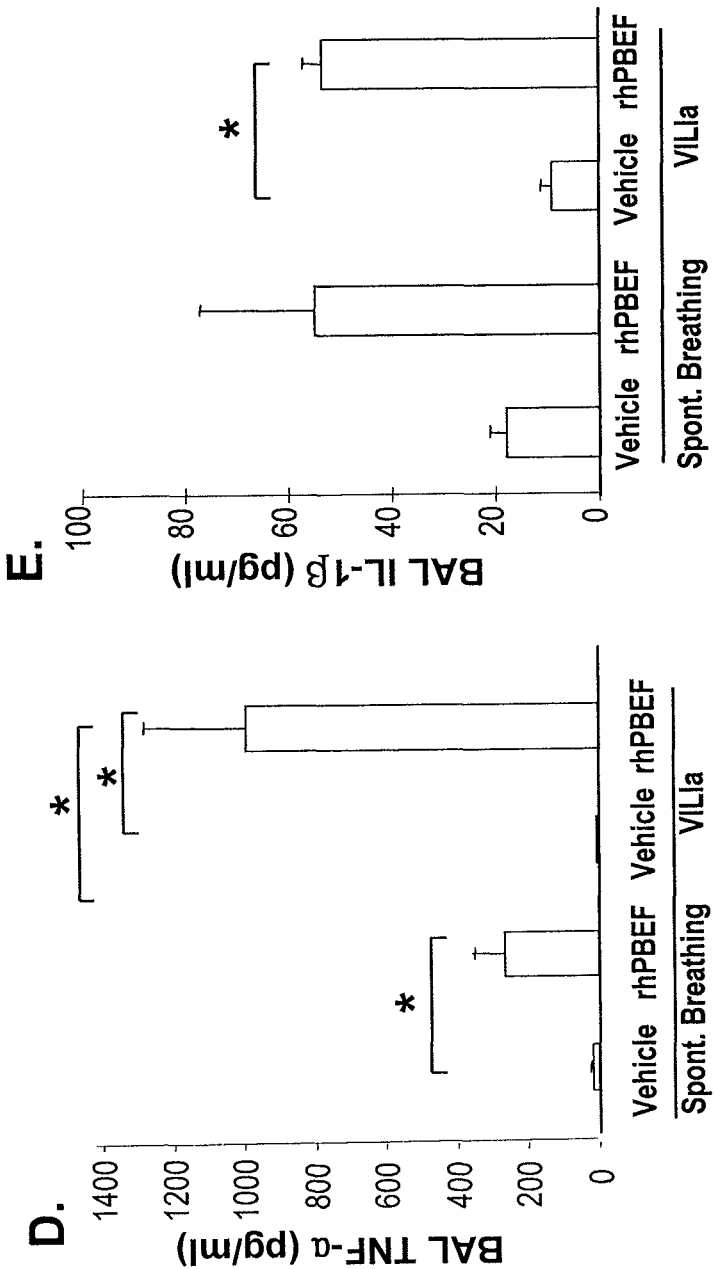

We next extended these in vitro findings to assess PBEF-induced PMN lung recruitment in spontaneously breathing B6 mice receiving intratracheal instillation of rhPBEF. We observed that PBEF produced significant increases in total BAL cells ($p<0.01$, FIG. 1B) and BAL neutrophils ($p<0.05$, FIG. 1C), findings confirmed by cytologic observations (FIG. 1D). rhPBEF does not increase the level of BAL protein content in spontaneously breathing animals (FIG. 2A) but does modestly increase levels of lung tissue albumin ($p<0.05$, FIG. 2B). Supporting the pro-inflammatory effects of PBEF, we noted PBEF-mediated increases in the BAL level of inflammatory cytokines such as IL-6 ($p<0.01$), TNF-α ($p<0.05$), and IL-1β ($p=0.01$), as well as PMN chemokines KC ($p<0.001$), and MIP-2, ($p<0.001$) compared to controls (FIG. 3A-E).

Example 5

Figure 4:
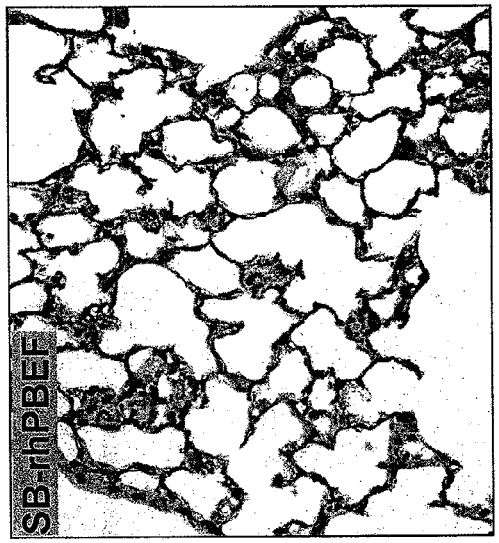
FIG. 4. Histologic assessment of rhPBEF effects on ventilator-induced lung inflammation and injury. Lungs from each experimental group (n=3) were inflated to 25 cm H₂O with 0.2% of low melting agarose and fixed in 4% paraformaldehyde at 4° C. for histologic evaluation by hematoxylin and eosin staining. Histologic analysis of lung tissue (40×) obtained from control mice (SB-vehicle, 30 µl vehicle intratracheal) demonstrated preserved lung parenchymal architecture. In contrast, mice exposed to either VILIa for 4.5 hours (VILIa-vehicle) or to a lesser degree, rhPBEF (20 µg/mouse dissolved in 30 µl of saline) (SB-rhPBEF) produced macrophage & neutrophil infiltration and edematous alveolar areas. Each of these features was dramatically augmented in mice receiving intratracheal rhPBEF 30 min prior to placement on mechanical ventilation for 4 hr (VILIa-rhPBEF).
Figure 4:
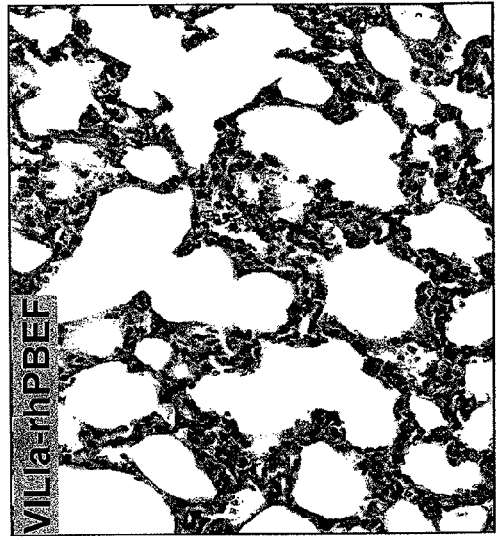
Figure 4:
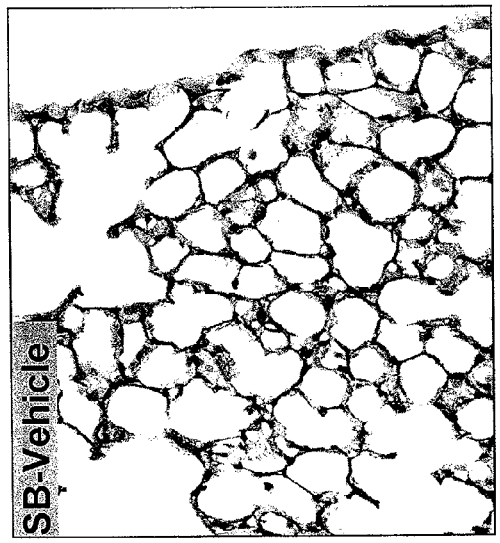
Figure 4:
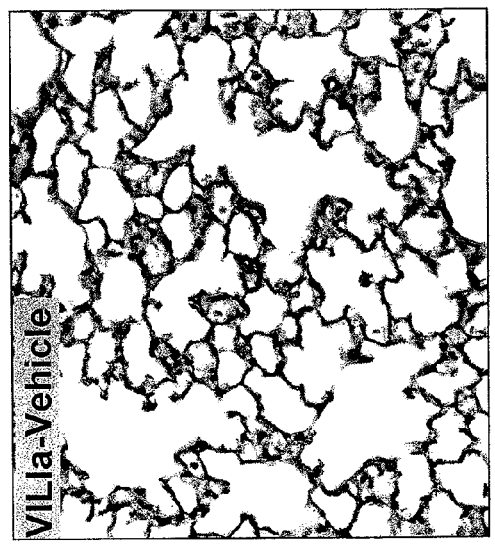

Inflammatory Effects of rhPBEF in a Model of Ventilator-Induced Murine Lung Injury The inventors next examined potential synergism between rhPBEF challenge and the mechanical stress produced in B6 mice by exposure to a limited lung injury model elicited by high tidal volume ventilation (VILIa, 4 hours, 30 ml/kg tidal volume). There were no statistically significant differences in pH, $PaO_2$, $PaCO_2$, $HCO_3$, and peak inspiratory pressures at the end of the mechanical ventilation period between the VILIa alone and VILIa-rhPBEF groups (Supplementary Table E1). Compared to spontaneously breathing (SB) mice, mice exposed to VILIa alone (without IT rhPBEF) exhibited increased BAL protein levels ($p<0.001$), increased lung tissue albumin ($p=0.03$) and increased levels of MIP-2 ($p<0.001$), IL-6, KC, and IL-1β (FIGS. 1-3). However, the VILIa-rhPBEF group (IT rhPBEF followed by mechanical ventilation) demonstrated dramatic increases in BAL total cells ($p<0.001$), BAL PMNs ($p<0.001$), BAL protein ($p<0.05$) and levels of several cytokines inducing IL-6, TNF-α, MIP-2, IL1-β and KC ($p<0.05$ all) compared to VILIa-challenged mice (FIGS. 1-3). Histologic assessment demonstrated that both SB-rhPBEF- and VILIa-exposed mice exhibit mild inflammation compared to the SB group. However, VILIa-rhPBEF challenged mice produced greater alveolar wall thickening, and neutrophil infiltration into the lung interstitium and alveolar space (FIG. 4) but with relative preservation of alveolar architecture and only modest alveolar and tissue edema.

Example 6

Figures 5A, 5B, 5C, 5D:
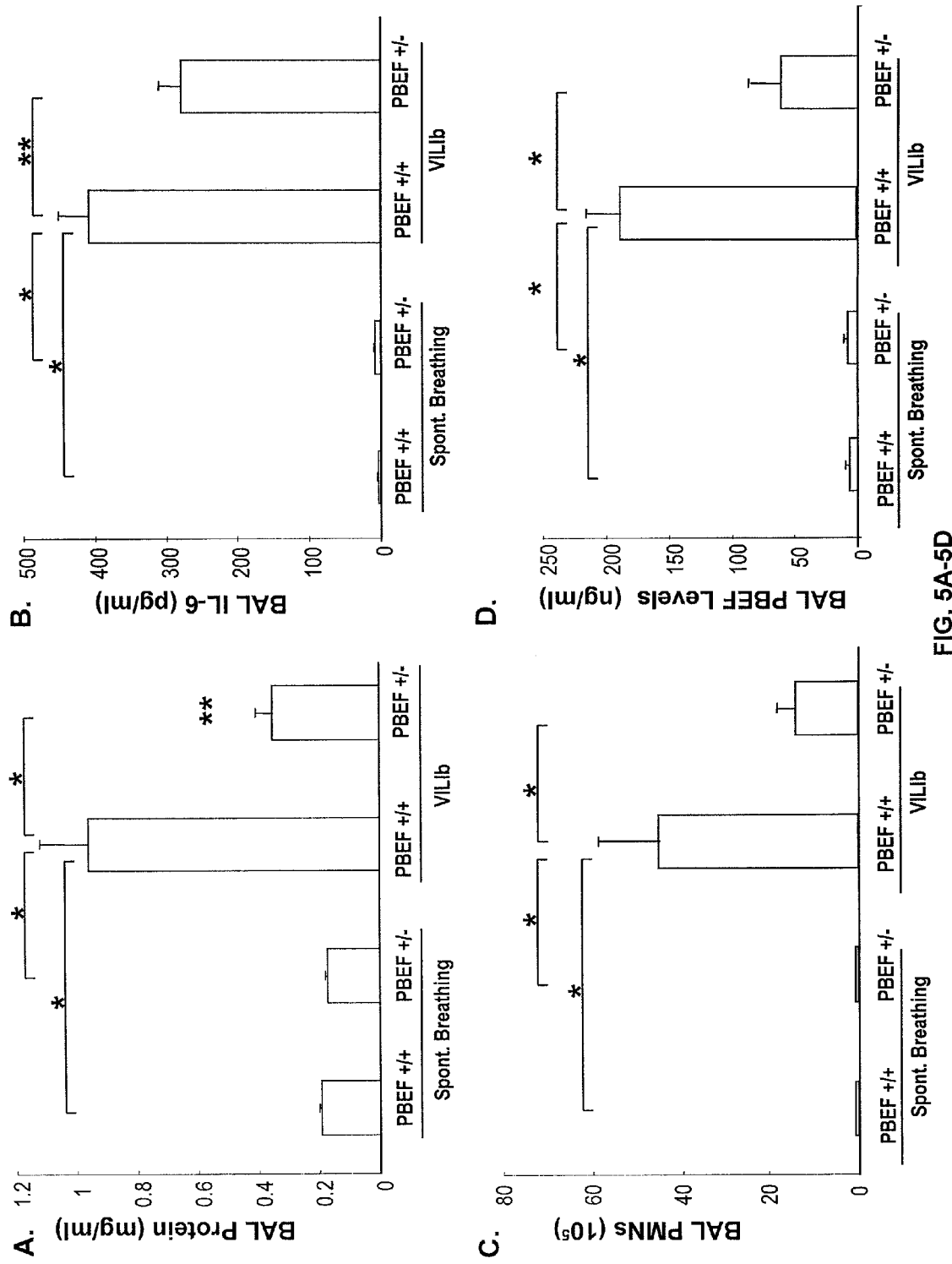
FIG. 5. PBEF$^{+/-}$ mice are protected in a model of severe ventilation-induced lung injury. Panel A. In contrast to the increase in BAL protein induced by VILIb (40 ml/kg—4 hr) in wild type PBEF$^{+/+}$ mice (* p<0.05), this effect was largely abrogated in the PBEF$^{+/-}$ mice (VILIb-PBEF$^{+/+}$ 0.96 mg/ml±0.16 vs. VILIb-PBEF$^{+/-}$ 0.35±0.06, ** p<0.05). Panel B. Evaluation of BAL cytokines in VILIb-challenged wild type mice and VILIb-exposed PBEF$^{+/-}$ mice showed that PBEF$^{+/-}$ mice had negligible levels of IL-6 at baseline (SB-PBEF$^{+/-}$, 8±1) and significantly less elevated IL-6 concentrations when compared to wild type mice exposed to VILIb mechanical ventilation (VILIb-WT, 407±43 pg/ml vs. VILIb-PBEF$^{+/-}$, 278±30; * p<0.05). Data represents mean values±SEM, pg/ml and N=6 animals in all experiments. Panel C. Shown are comparisons of BAL neutrophil counts in VILIb-WT (44.8×10⁵±26.9) vs. VILIb-PBEF$^{+/-}$ mice (13.9±4.4, * p<0.05). PMN counts were dramatically reduced in PBEF$^{+/-}$ mice when compared to wild type mice (* p<0.0001). Panel D. Shown are the levels of PBEF in BAL fluid as determined by ELISA (see supplemental methods for details). As expected, levels of PBEF in mice exposed to a model of severe VILI (VILIb) were significantly higher in VILIb-challenged wild type mice compared to VILIb-exposed PBEF$^{+/-}$ mice (187 ng/ml±28 vs. 60±30; * p<0.05).

Responses of $PBEF^{+/-}$ Heterozygous Mice to Severe Ventilator-Induced Murine Lung Injury To further explore the in vivo contribution of PBEF generation to ventilator-induced lung injury, the inventors next generated a heterozygous $PBEF^{+/-}$ mouse line with targeted deletion of a single PBEF allele, and subsequently exposed these mice to a model of severe VILI (VILIb, 4 hours, 40 ml/kg tidal volume). Wild type (WT) and heterozygous $PBEF^{+/-}$ mice were statistically similar in acid-base parameters (pH, $PaO_2$, $PaCO_2$, $HCO_3$) before and after exposure to 4 hours of mechanical ventilation and in the peak inspiratory pressures at the initiation of mechanical ventilation (Supplementary Table E1). However, VILIb-exposed $PBEF^{+/-}$ mice were significantly protected from VILI with significantly decreased inflammatory lung injury and lower peak inspiratory pressures (PIP) at the end of the mechanical ventilation period compared to wild type mice (22.0 mmHg±1.6 vs. 26.7±2.9, $p<0.05$) (Supplementary Table E1). For example, the increase in BAL protein induced by VILIb was largely abrogated in $PBEF^{+/-}$ mice (FIG. 5A, $p<0.05$) compared to WT mice and the increases in BAL IL-6 levels were also significantly reduced in VILIb-challenged $PBEF^{+/-}$ mice (FIG. 5B, $p<0.05$). Additional indices of lung injury such as total BAL PMNs were significantly lower in $PBEF^{+/-}$ mice ($1.37 \times 10^5 \pm 0.7$ vs. $44.8 \times 10^5 \pm 26.9$, $p<0.05$) compared to controls (FIG. 5C). The levels of inflammatory cytokines (KC, MIP-2, IL-1β, TNFα, data not shown) were all reduced in VILIb-challenged $PBEF^{+/-}$ mice but failed to reach statistical significance. As expected, compared to wild type mice, $PBEF^{+/-}$ mice exposed to a model of severe ventilation-mediated lung injury (VILIb) demonstrated significant reductions in lung PBEF levels (187 ng/ml±28 vs. 60±30; $p<0.05$) (FIG. 5D). Basal PBEF levels in spontaneously breathing WT and $PBEF^{+/-}$ mice were negligible.

Example 7

Genomic Analysis of Wild Type and $PBEF^{+/-}$ Mice Exposed to RHPBEF and Mechanical Ventilation We next attempted to determine molecular signatures which describe the direct effects of PBEF as well as the synergistic effects of rhPBEF in VILI-mediated inflammatory injury. We performed microarray analyses of spontaneously breathing, rhPBEF-challenged wild type and heterozygous PBEF$^{+/-}$ mice as well as mice exposed to mechanical ventilation-induced lung injury. Dysregulated genes identified by pairwise comparison of 2 groups using SAM software are summarized in Supplementary Table E2. The functional profiles of the dysregulated genes were also explored by IPA for canonical pathways and analyzed by OntoExpress for gene ontology assessment in order to identify the over-represented biological processes (Supplementary Table E3 and E4).

Figure 6A:
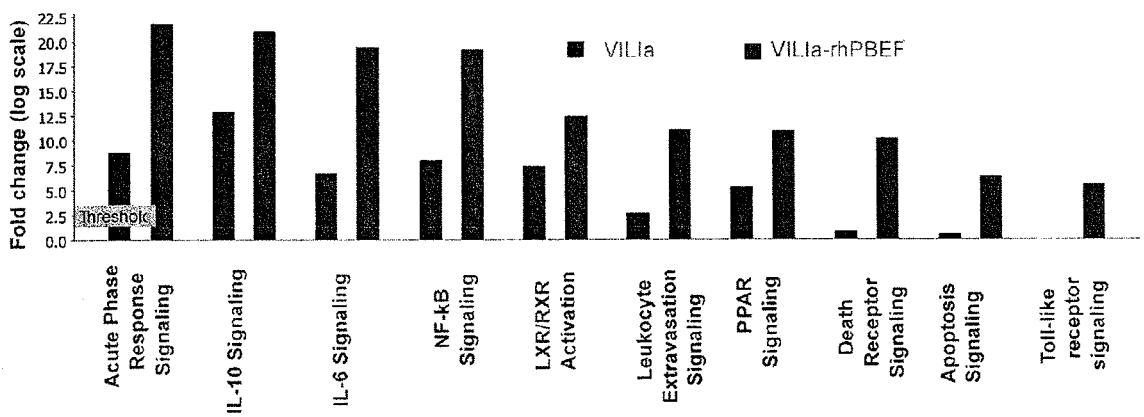
FIG. 6. Ingenuity Pathway Analysis of rhPBEF-mediated dysregulated genes. The addition of rhPBEF to VILIa produces a strong signature of dysregulated genes (see Supplementary Table E2 for description of gene selections with SAM software, gene list 2 and 3 for VILIa and VILIa-rhPBEF treatment, respectively). Panel A. Significant canonical pathways enriched with dysregulated genes induced by VILIa or VILIa-rhPBEF treatment. The threshold line represents the Fisher-exact p value of 0.05 (see supplement Methods section). Panels B and C. Fold changes of the dysregulated genes induced by VILIa or VILIa-rhPBEF treatment in the NFκB (Panel B) and leukocyte extravasation pathway (Panel C).
Figure 6B:
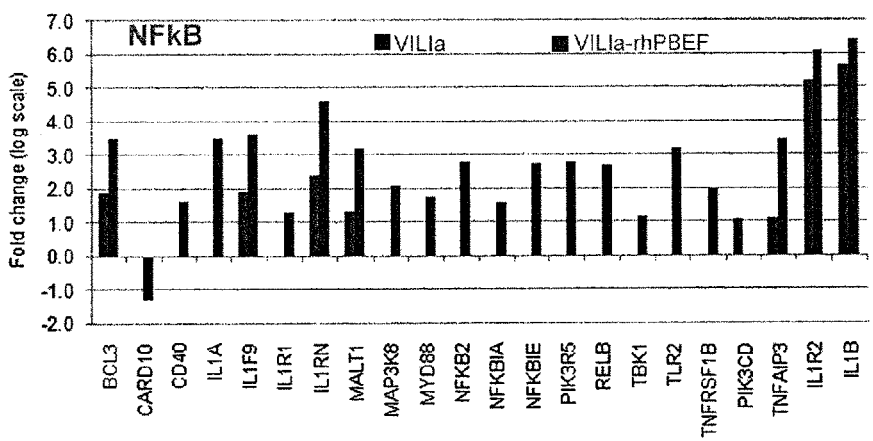
Figure 6C:
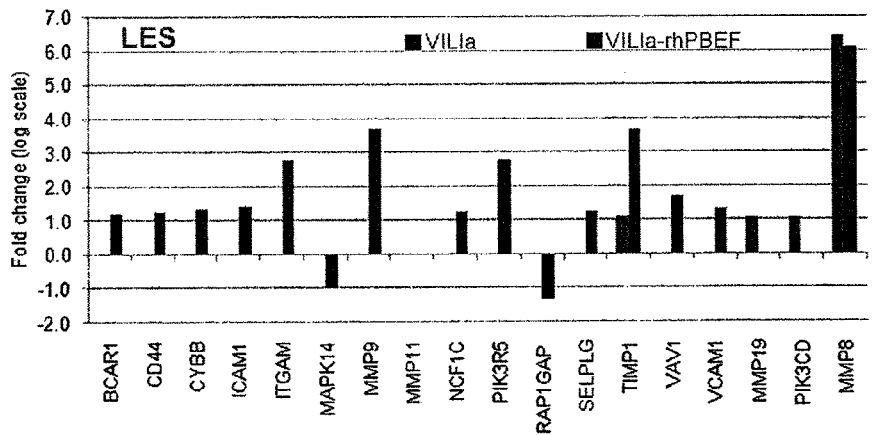

Interestingly, the majority of the signaling pathways deregulated by rhPBEF challenge (acute phase response signaling, IL-10, nuclear factor kappa B (NFκB), IL-6, leukocyte extravasation) (Supplementary FIG. E1) were identical to those pathways affected by VILIa treatment (FIG. 6A), thus highlighting the potential involvement of PBEF in VILI pathogenesis. The potential for additive effects of rhPBEF on VILI-induced inflammation was confirmed by the greater number of dysregulated genes induced by the combined VILIa-rhPBEF exposure (690 genes) compared to VILIa alone (220 genes) (Supplementary Table E2). The common canonical VILIa-induced signaling pathways which were augmented by combined rhPBEF challenge include the acute phase response signaling, IL-10, IL-6, NFκB, Peroxisome Proliferator-Activated Receptors (PPAR) and the liver X receptor/retinoid X receptor ligands (LXR/RXR) signaling pathways (FIG. 6A). Deregulated pathways such as toll-like signaling and apoptosis signaling pathways were only induced by the combined challenge of VILIa and rhPBEF and not altered by VILIa alone (FIG. 6A). The potent effects of rhPBEF on these processes are highlighted for the NFκB signaling pathway in FIGS. 6A and 6B, for the leukocyte extravasation signaling pathway in FIGS. 6A and 6C, and for the apoptosis pathway in FIG. 6A and Supplementary FIG. E2. These findings are consistent with the capacity of rhPBEF to induce lung inflammation, with the majority of genes in these pathways driven by rhPBEF administration and not by exposure to VILIa. For example, a total of 21 dysregulated genes in the NFκB pathway were altered by the VILIa-rhPBEF combined exposure, whereas only eight dysregulated genes were found in the VILIa group alone (each exhibiting much lower fold changes than VILIa-rhPBEF) (FIG. 6B). Additional details of deregulation of the murine NFκB and leukocyte extravasation pathways following exposure to VILIa-rhPBEF are depicted in Supplementary FIGS. E3 and E4, respectively. Similar to the findings in canonical pathway analysis, the GO analysis revealed that combined VILIa-rhPBEF challenge induced the deregulation of several novel biological processes, such as chemotaxis, small GTPase-mediated signal transduction, and cytokine and chemokine-mediated signaling pathways (Supplementary Table E3).

Figure 7A:
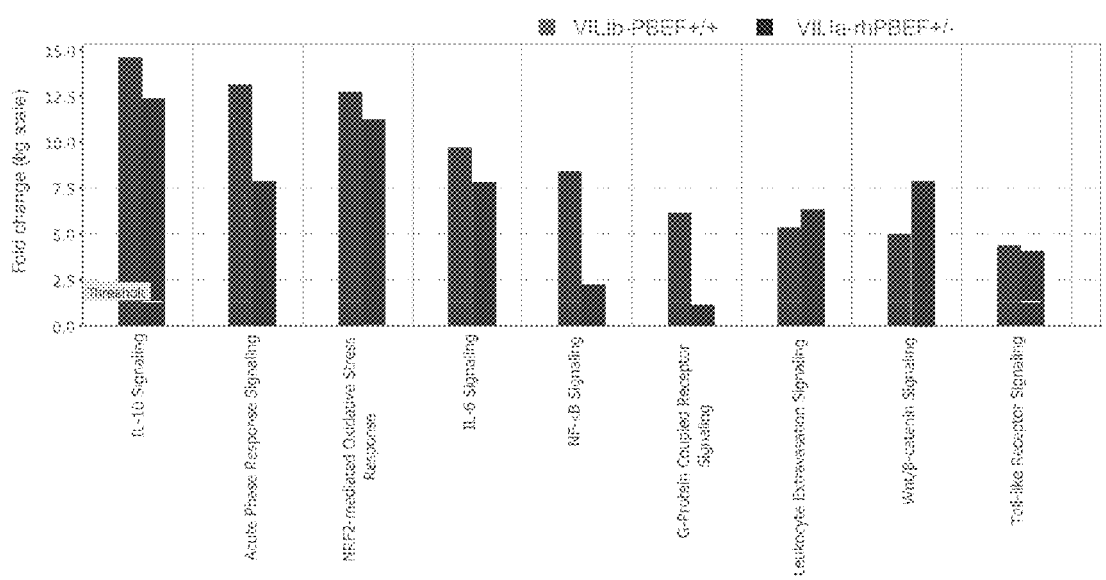
FIG. 7. Ingenuity Pathway Analysis of dysregulated genes in PBEF$^{+/-}$ mice. Panel A. Listed are significant canonical pathways enriched with dysregulated genes induced by VILIb-PBEF$^{+/+}$ and VILIb-PBEF$^{+/-}$. Panel B. Depicted are fold changes of the dysregulated genes induced by VILIb-WT or VILIb-PBEF$^{+/-}$ in the IL-6 signaling pathway. See Supplementary Table E2 for the description of gene selections with SAM software (gene list 6 and 7 for VILIb-WT and VILIb-PBEF$^{+/-}$ challenge, respectively).
Figure 7B:
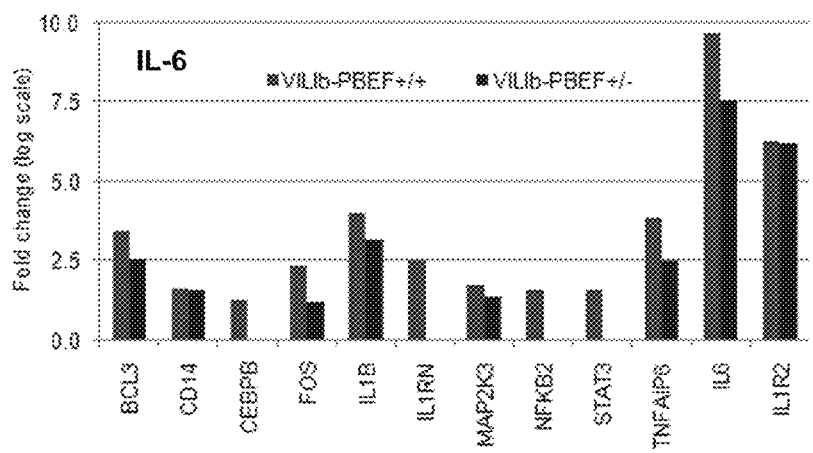

As noted above, we utilized two models of VILI: a model of limited VILI with tidal volume of 30 ml/kg (i.e., VILIa) in order to interrogate the synergy between rhPBEF and VILI, and a second model of severe VILI with a tidal volume of 40 ml/kg (i.e., VILIb) to evaluate the potential protection afforded by deletion of a PBEF allele in PBEF$^{+/-}$ mice. Despite use of stringent gene filtering criterion (see Supplementary Table E2), wild type mice exposed to the more severe VILIb protocol induced a greater number of dysregulated genes (748 genes) than the less injurious VILIa protocol (220 genes), indicating a clear dose-dependent effect of mechanical stress on gene dysregulation induced by VILI exposure. Murine expression profiling displayed minimal impact of the PBEF$^{+/-}$ genotype on basal global gene expression (Supplementary Table E2) with only 8 dysregulated genes (including PBEF, CYP1A1 and an uncharacterized cDNA BC018473). However, consistent with the critical role of PBEF in VILI, specific deregulated pathways induced by VILIb in wild type mice were absent in PBEF$^{+/-}$ mice including the previously noted NFκB and G-protein-coupled receptor signaling pathways (FIG. 7A), indicating a clear protective effect of PBEF$^{+/-}$ genotype on VILIb-induced genomic alterations. For example, compared to VILIb-challenged wild type mice, the expression of all VILIb-induced deregulated genes in the IL-6 pathway (e.g. IL1RN, NFKB2, STAT3, IL-6) were either reduced or failed to be dysregulated in PBEF$^{+/-}$ mice exposed to VILIb (FIG. 7B). Results for selected genes (Cxcl1, Cxcl2, BCL3, Map3k8, MMP9, Il-6, Il-1β, TNFα and BC018473) were further validated by ELISA and RT-PCR approaches (Supplementary Table E5). VILIb-induced dysregulated genes in wild type or PBEF$^{+/-}$ mice submitted to OntoExpress (to identify the overrepresented biological processes) demonstrated several deregulated biological processes induced by VILIb in wild type mice which were absent in the PBEF$^{+/-}$ group, including cytoskeleton organization and biogenesis, angiogenesis and defense responses (Supplementary Table E5).

Figure 8:
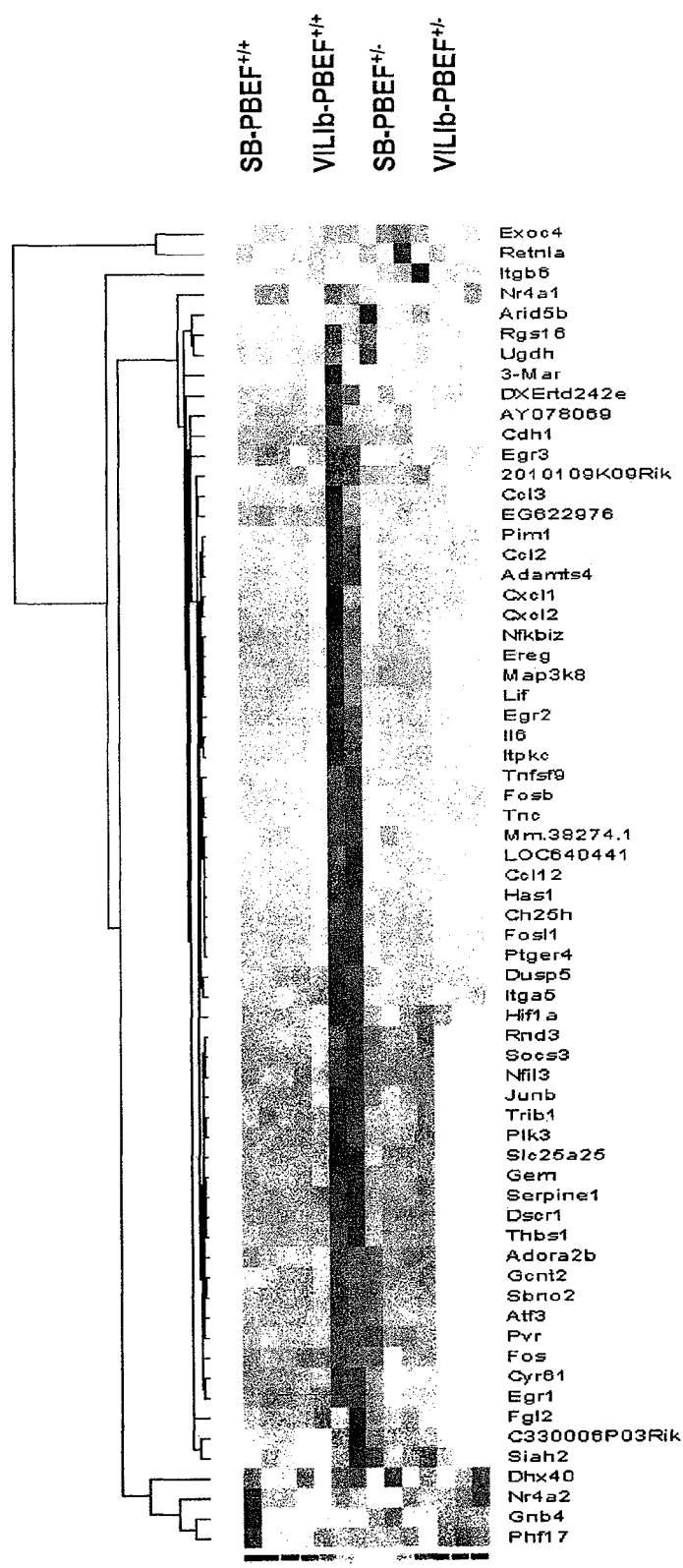
FIG. 8. Gene expression pattern of differentially expressed genes in VILIb-challenged WT mice and VILIb-challenged PBEF$^{+/-}$ mice. Differentially expressed genes between VILIb-WT and VILIb-PBEF$^{+/-}$ challenged mice were generated by SAM (Supplementary Table E2). The expression levels of the differentially expressed genes between VILIb-WT and VILIb-challenged PBEF$^{+/-}$ mice are displayed by dChip hierarchical clustering. Blue, white, and red colors represent expression level below, at, and above mean level, respectively.

We next explored the impact of rhPBEF or PBEF$^{+/-}$ on the global gene expression pattern in VILI-treated animals. Sixty-five differentially expressed genes were identified by pairwise comparison between VILIa-rhPBEF and VIIIa groups with 43 genes demonstrating ranked expression levels; i.e., an order of: control<VILIa<<VILIa-rhPBEF. Similarly 66 genes were identified between VILIb-challenged PBEF$^{+/-}$ mice and VILIb-exposed wild type mice (Supplementary Table E2). Hierarchical clustering of the gene expression levels across all experimental groups are displayed in FIG. 8, with 64 out of the 66 genes following the order of: control<VILIb-PBEF$^{+/-}$<<VILIb-PBEF$^{+/+}$. Together, these findings support the notion that rhPBEF exaggerates VILI-induced gene dysregulation, while the PBEF$^{+/-}$ genotype attenuates this dysregulation.

Example 8

Figure 9A:
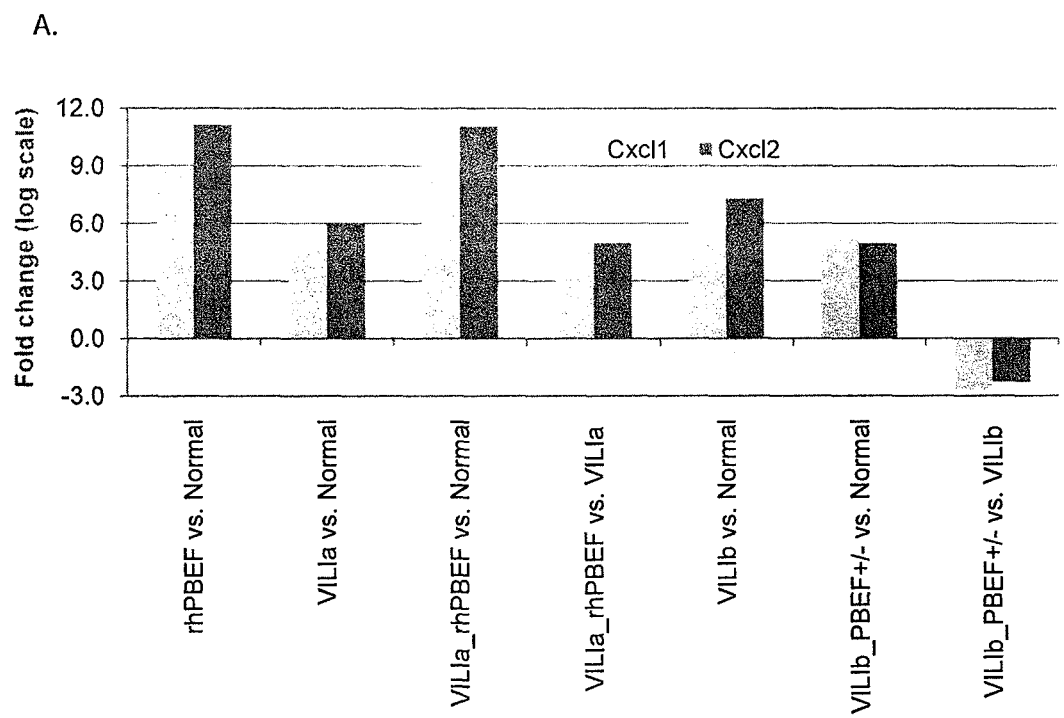
FIG. 9. Validation of potential VILI biomarkers in lung tissue and in BAL fluid. Panel A. Two markers, Cxcl1 and Cxcl2, were selected by their presence across all gene lists (Supplementary Table E2); (except list 5 for dysregulated genes in PBEF$^{+/-}$ mice). The levels of each gene mirrored the severity of VILI and/or the injury produced by VILI and rhPBEF challenges suggesting that Cxcl1 and Cxcl2 represent potential biomarkers in VILI. Panel B. VILIa- and rhPBEF-mediated challenge of wild type B6 mice each induced significantly increased fold changes in CxCl1, CxCl2, IL-1β, IL-6, and TNFα compared to spontaneously breathing controls (* p<0.05) in BAL. Moreover, the combined challenge of VILIa-rhPBEF indicated an additive effect on the induction of these cytokines (* p<0.05). Panel C. Exposure of wild type B6 mice to VILIb induced significantly elevated fold changes in CxCl1, CxCl2, IL-1β, IL-6, and TNFα relative to VILIb-PBEF$^{+/-}$ mice. Reductions in BAL-cytokine production in VILIb-PBEF$^{+/-}$ mice is significant with IL-6 (* p<0.05).

Evaluation of Molecular Markers in VILI- and rhPBEF-Challenged Wild Type and PBEF$^{+/-}$ Mice We assessed the intersection of the combined VILI and PBEF challenge by comparing the overlapping genes across all gene lists (Supplementary Table E2). This subsequently identified 2 genes, Cxcl1 (aka KC) and Cxcl2 (aka MIP-2), which displayed significant alterations across each list (except gene list 5) (FIG. 9A). Both Cxcl1 and Cxcl2 displayed tidal volume- and rhPBEF-dependent responses with fold changes in gene expression much greater in severe VILIb-challenged mice (Supplementary Table E5; 251 fold increase-Cxcl1, 157 fold increase-Cxcl2) rather than limited VILIa (24 fold-Cxcl1, 67 fold-Cxcl2) and was much higher when mice were exposed to VILIa-rhPBEF (589 fold-Cxcl1, 2128 fold-Cxcl2) compared to VILIa alone.

Figure 9B:
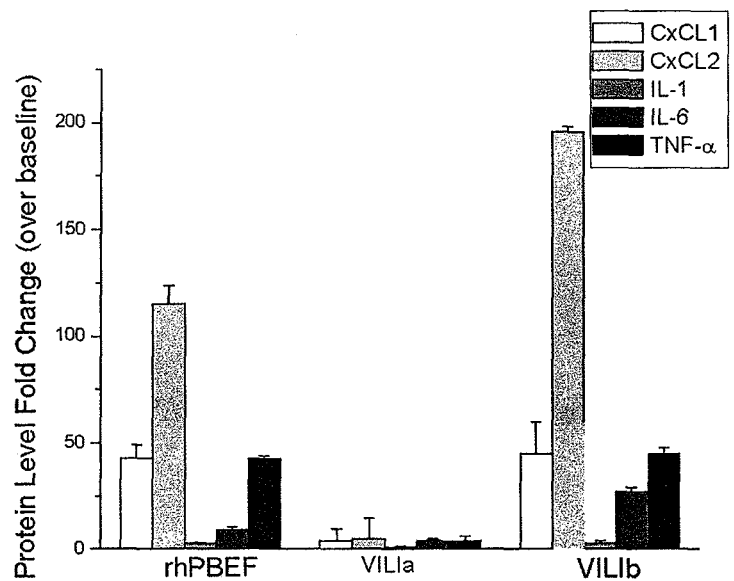
Figure 9C:
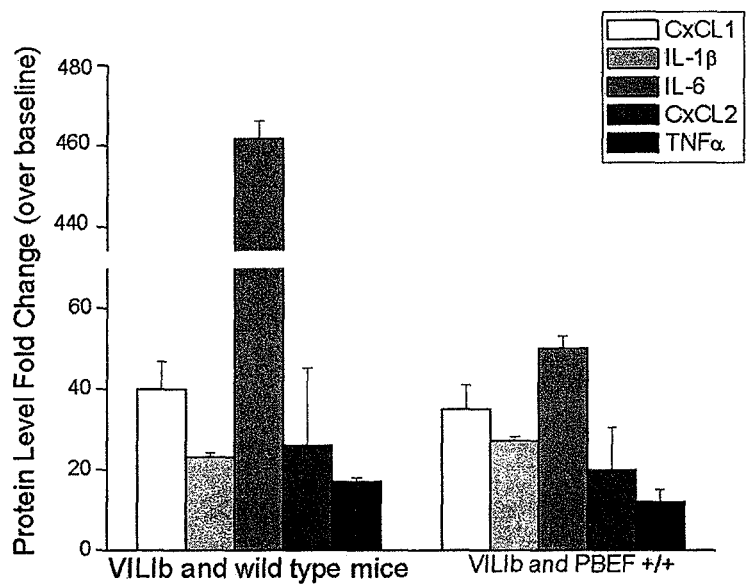

Complementing these changes in gene expression, BAL fluid was also assessed for levels of CxCl1, CxCl2, IL-1β, IL-6, and TNF-α (FIG. 9B-C). Isolated challenge with rhPBEF or VILIa produced significantly increases in each cytokine compared to spontaneously breathing controls, while the combined challenge revealed an additive effect. In the VILIb model, the protective effect of PBEF$^{+/-}$ heterozygosity was again evident with reductions in all cytokines in VILIb-PBEF$^{+/-}$ mice compared to VILIb-wild type group. Only IL-6 levels in the VILIb-PBEF$^{+/-}$ group remained significantly reduced compared to controls. Collectively, the effects of rhPBEF and PBEF$^{+/-}$ heterozygosity on the production of these inflammatory cytokines further underscores the important role of PBEF in VILI.

Example 9

Figure 10:
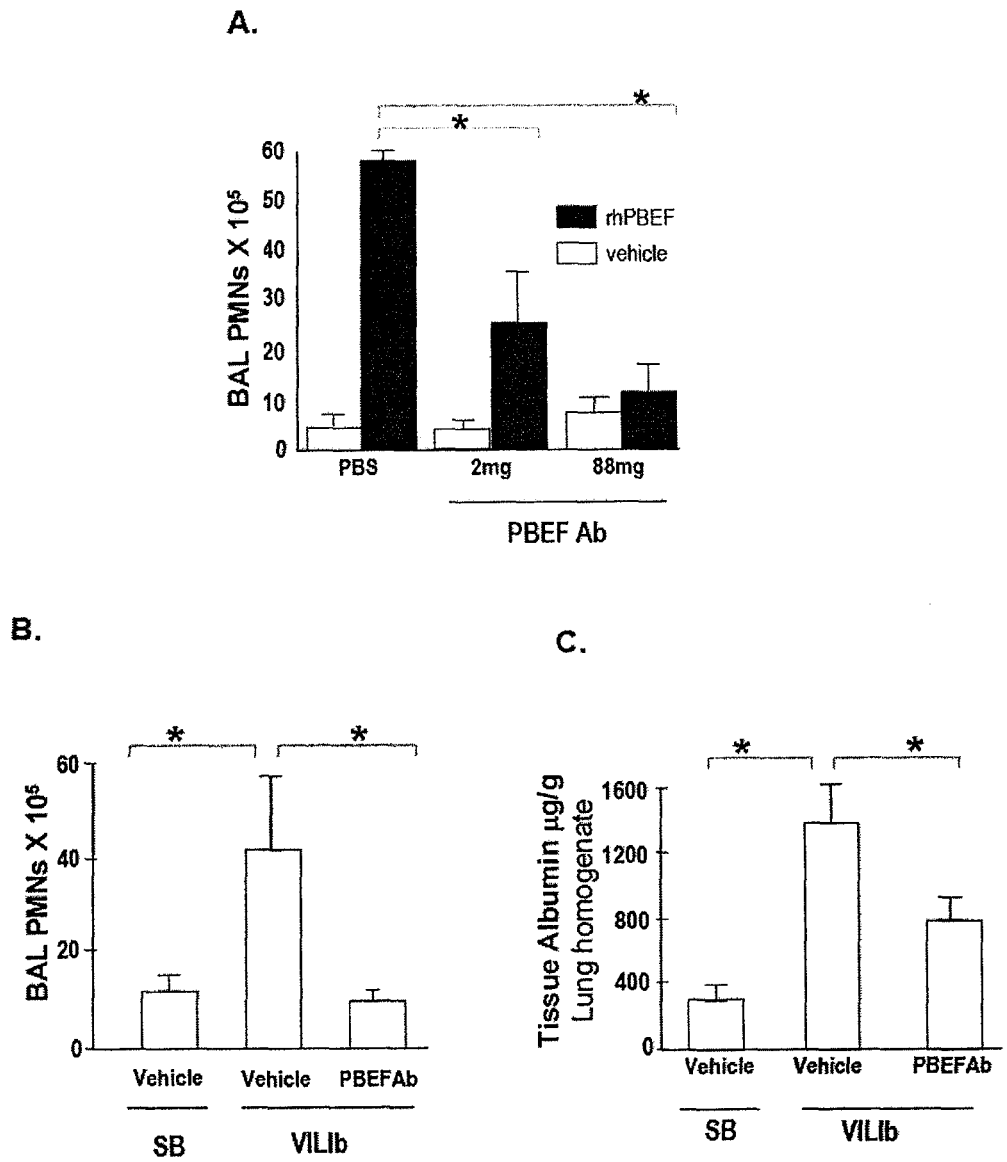
FIG. 10. Reductions in PBEF availability is protective in ventilation-induced lung injury. Panel A. We initially assessed the effect of PBEF neutralizing antibody (PBEF Ab) on rhPBEF-mediated PMN influx into lung tissues and alveolar space (4.5 hr, 20 µg/mouse). Simultaneous administration of rhPBEF and PBEF antibody (2 µg and 88 µg/mouse, ratio PBEF Ab/rhPBEF ratio of 0.1 and 4.4) resulted in marked reductions in PBEF-mediated accumulation of BAL PMNs (* p<0.05). Panels B and C. We next utilized PBEF neutralizing antibody (88 µg) via intratracheal delivery in VILIb-challenged B6 mice and determined that PBEF Ab reduces both VILI-induced PMN accumulation (Panel B) and tissue albumin leakage (Panel C) (40 ml/kg). (n=3-4); * p<0.05.
Figure 11:
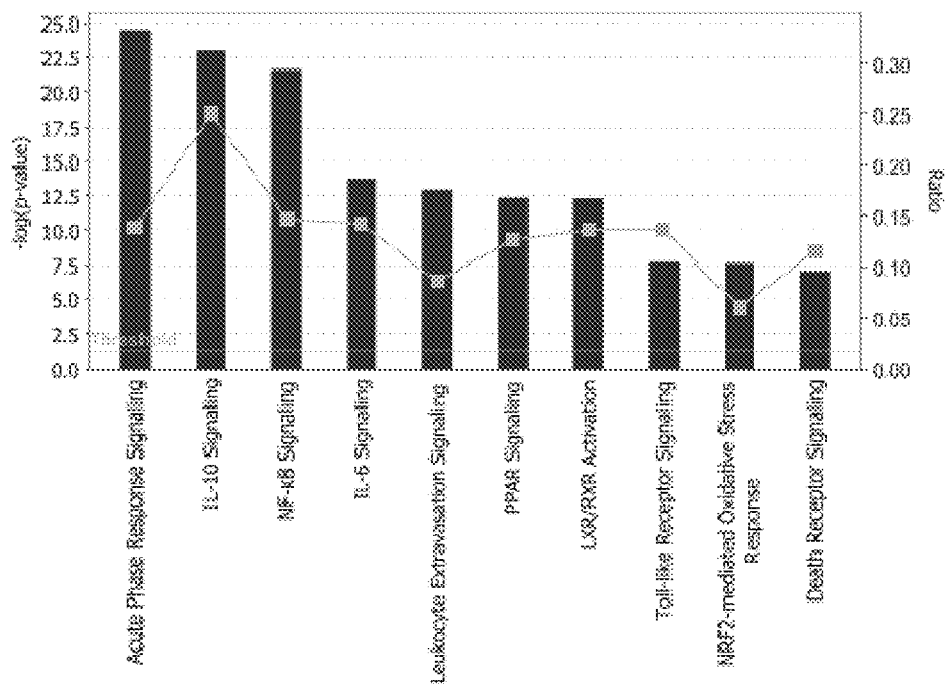
FIG. 11: Ingenuity Pathway Analysis (IPA) of dysregulated genes in rhPBEF-challenged mice. The 493 dysregulated genes (see Supplementary Table E2, gene list 2) were generated by pairwise comparison between rhPBEF challenged and control animals. The gene list was submitted into Ingenuity software to identify canonical pathways enriched with the dysregulated genes. The threshold line represents the Fisher-exact p-value of 0.05. The ratio line represents the percentage of the dysregulated genes in the total number of genes in the corresponding pathway.
Figure 12:
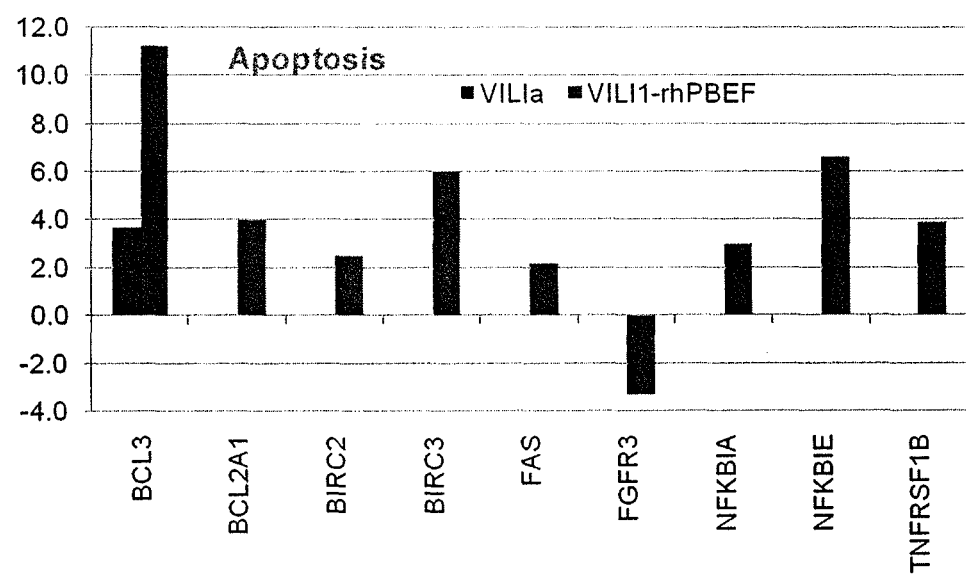
FIG. 12: Fold changes of the dysregulated genes induced by VILIa or VILIa-rhPBEF treatment in apoptosis pathway. The lists of dysregulated genes were generated using SAM software (Supplementary Table E2) and then submitted to Ingenuity Pathway Analysis software to identify canonical pathways enriched with dysregulated genes (FIG. 6A).
Figure 13:
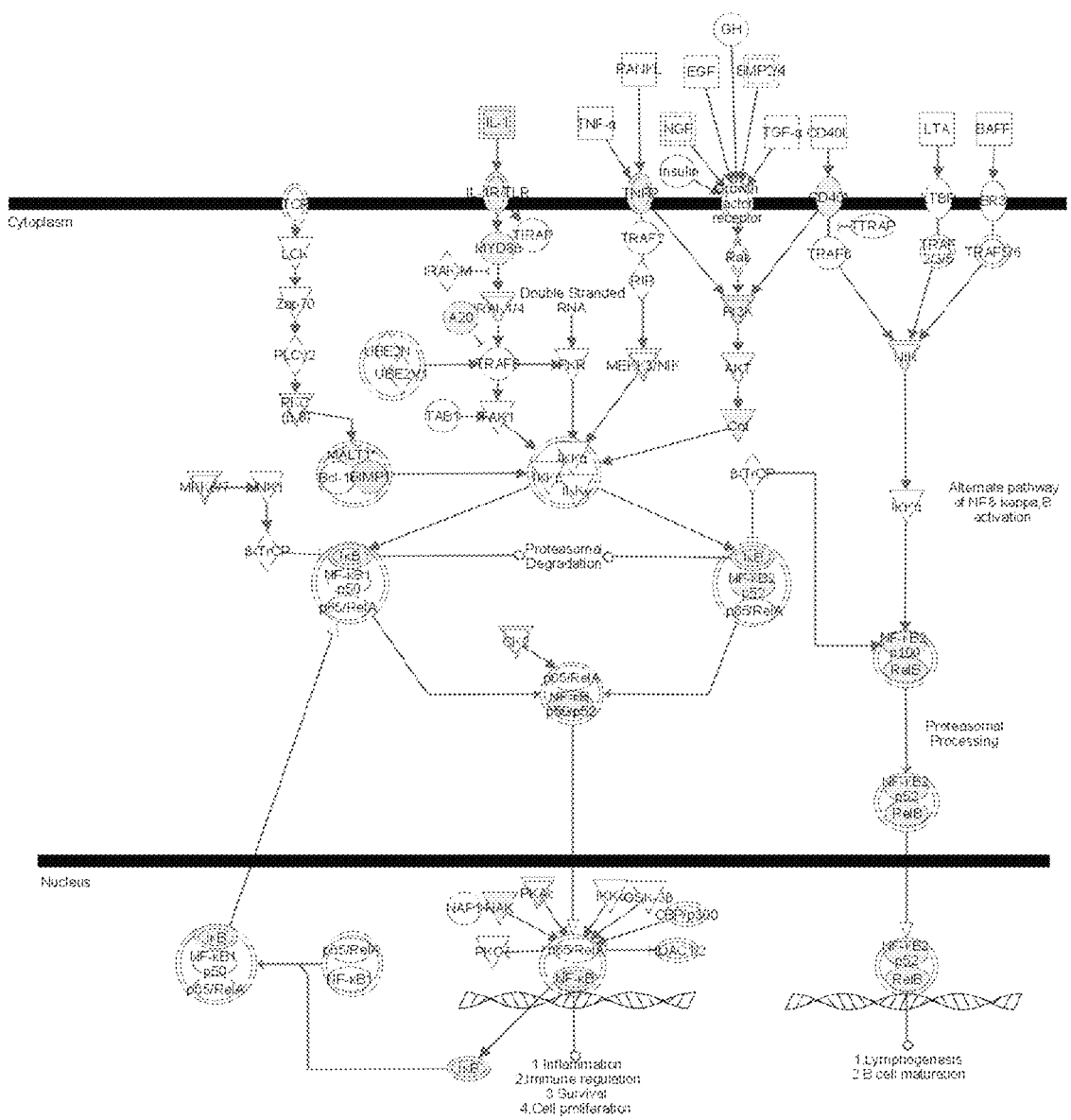
FIG. 13. Mapping of VILIa-rhPBEF-induced dysregulated genes in the NFκB pathway. The NFκB pathway was identified by IPA analysis (see FIG. 6B). Shown are the expanded set of up- and down-regulated genes highlighted in red and green, respectively as induced by exposure to combined VILIa and rhPBEF challenge.
Figure 14:
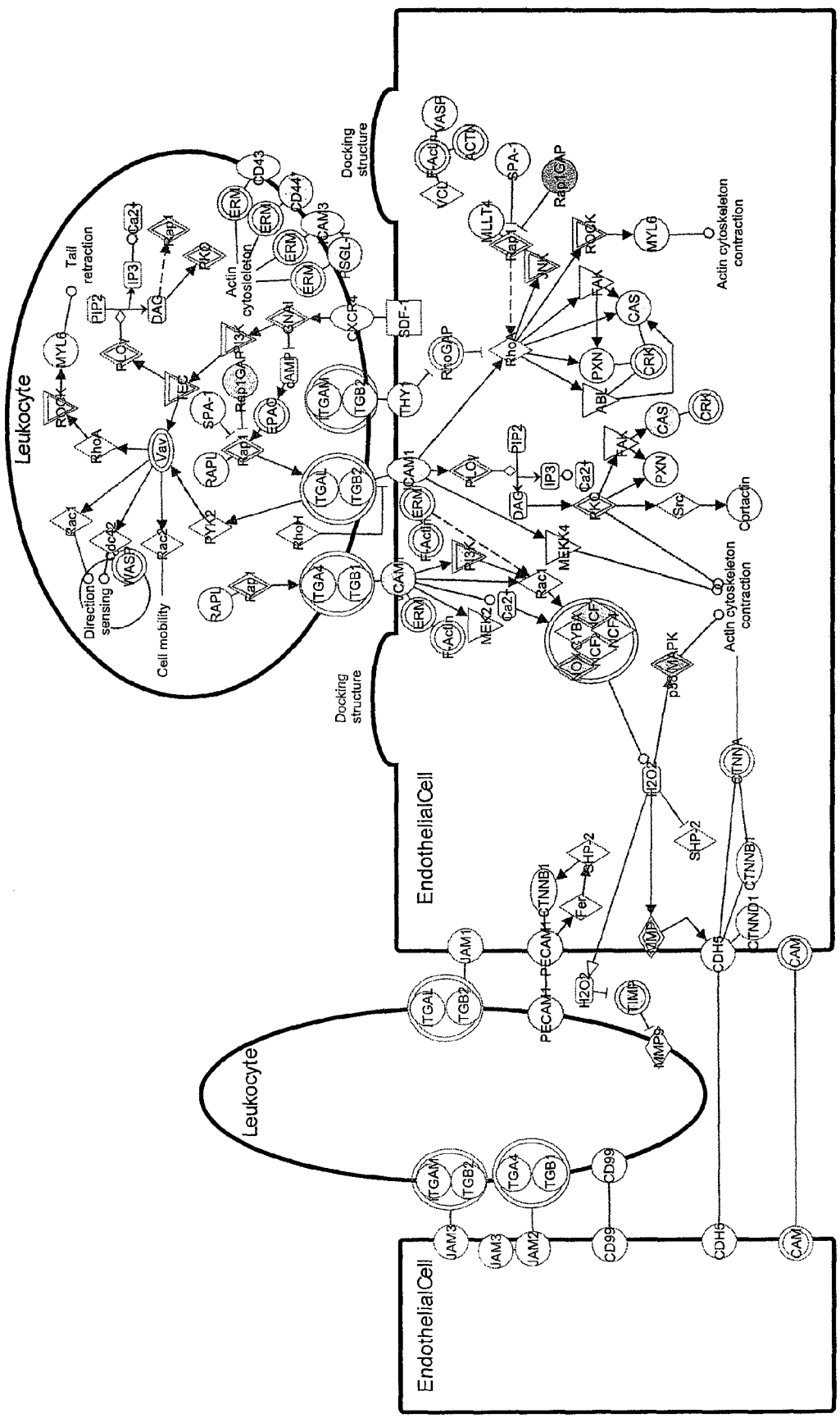
FIG. 14. Mapping of VILIa-rhPBEF-induced dysregulated genes in the leukocyte extravasation pathway. The leukocyte extravasation pathway was identified by IPA analysis (see FIG. 6C). Shown are the expanded set of up- and down-regulated genes highlighted in red and green, respectively as induced by exposure to combined VILIa and rhPBEF challenge.

Effect of Reduced PBEF Availability on VILI-Induced PMN Recruitment and Vascular Leakage To address the potential for PBEF to serve as a therapeutic target in ameliorating VILI, we generated PBEF antisera and assessed the effect of PBEF neutralizing antibody on rhPBEF-stimulated PMN recruitment into the alveolar space (FIG. 10A). Simultaneous instillation of rhPBEF (20 µg/mouse) and PBEF neutralizing antibody produced dramatic reductions in rhPBEF-induced PMN recruitment. We next assessed the ability of PBEF neutralizing antibody to reduce VILIb-mediated PMN recruitment and lung injury (40 ml/kg, 4 hrs). The intratracheal delivery of PBEF neutralizing antibody (30 min prior to mechanical ventilation) abolished VILIb-induced increases in total BAL cell counts and significantly decreased PMN influx into the alveolar space (FIG. 10B) as well as VILI-mediated increases in lung tissue albumin (FIG. 10C).

Example 10

Inhibition of PBEF

Materials and Methods.
PBEF1 Organism: Human; Gene ID: 10135; Accession Numbers: NM_005746

In vitro human PBEF stealth siRNAs were designed based on the human PBEF cDNA reference sequence (NM_005746.1) using the BLOCK-iTi RNAi Designer (Invitrogen, Carlsbad, Calif.). The siRNA sequence 1 (as reported in Ye et al. 2005 MVR w/@75% silencing) was custom synthesized from Invitrogen (cat#10620312_40993403, NM_005746); (5'-CCACCCAA-CACAAGCAAAGUUUAUU-3' SEQ ID NO:4) and scrambled controls (cat#10620312_40993404).

Alternatively, small interfering RNA (siRNA) targeting human PBEF1 (NM_005746) was purchased as 4 ON-TARGETplus SMARTpool siRNA duplexes (catalog#L-004581-00) from Dharmacon (Lafayette, Colo.).

PBEF1 Organism: Mouse; Gene ID: 59027; Accession Numbers: NM_021524

Small interfering RNA (siRNA) targeting mouse PBEF1 (NM_021524) was designed using siDESIGN Center website tool (Dharmacon, Lafayette, Colo.). PBEF1 duplex oligos (5'-GGAAAGACCAUGAGAAAGAUU-3' SEQ ID NO:5) were synthesized with in vivo processing option and siSTABLE® for stability enhanced siRNA. Control duplex oligos (5'-UAAGGCUAUGAAGAGAUACUU-3' SEQ ID NO:6) targeting a non-human/mouse protein, luciferase, was also synthesized with in vivo processing option and siSTABLE® and referred to as siCONTROL2.

Figure 15:
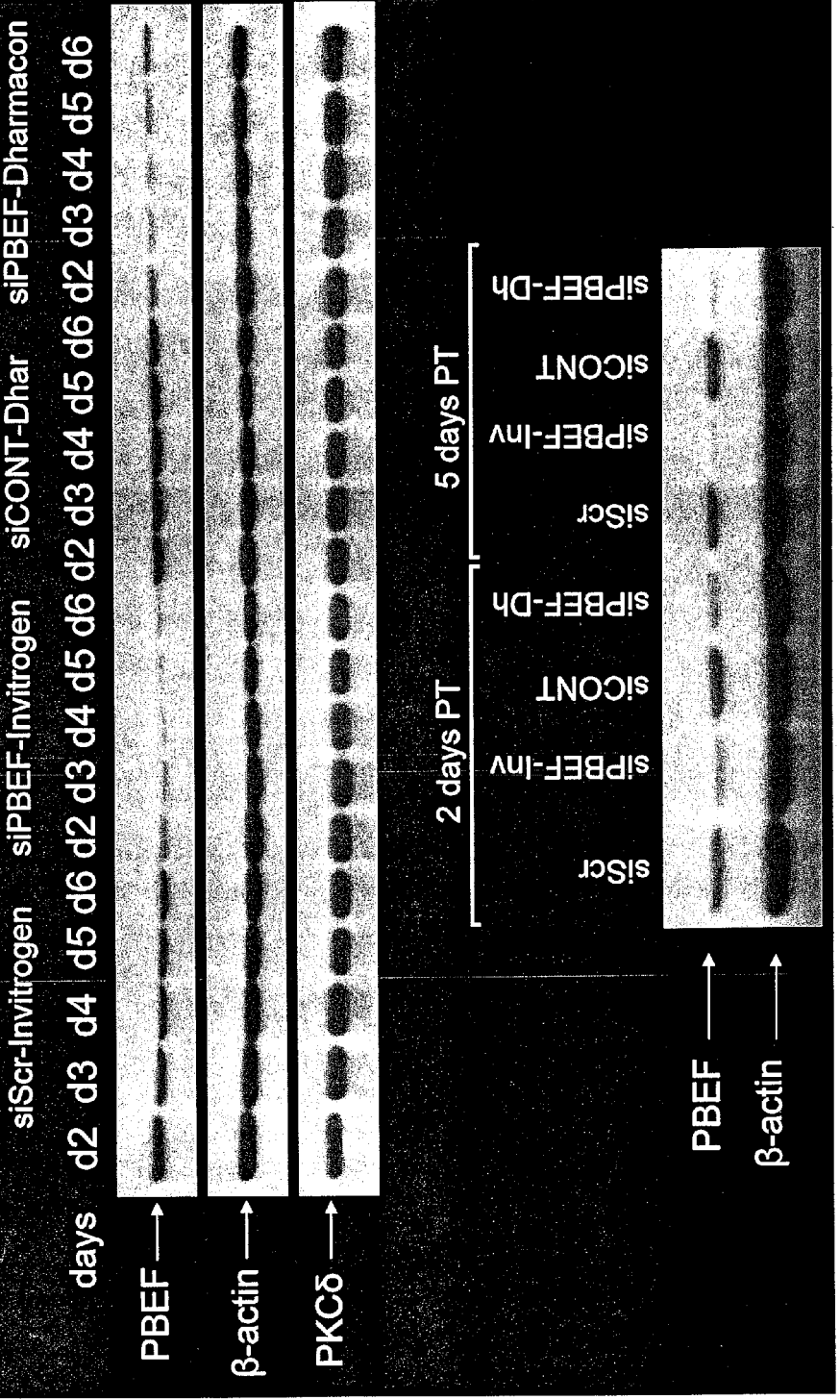
FIG. 15. In vitro PBEF Silencing with siRNAs. Optimal in vitro PBEF silencing required 4-5 days post-transfection. The extended silencing duration allowed us to manipulate experiments to accommodate both siRNA and 48 hr of 18% CS. Both Invitrogen (single sequence) and Dharmacon (pool of 4 sequences) siRNAs were effective in downregulating PBEF protein expression.
Figure 16:
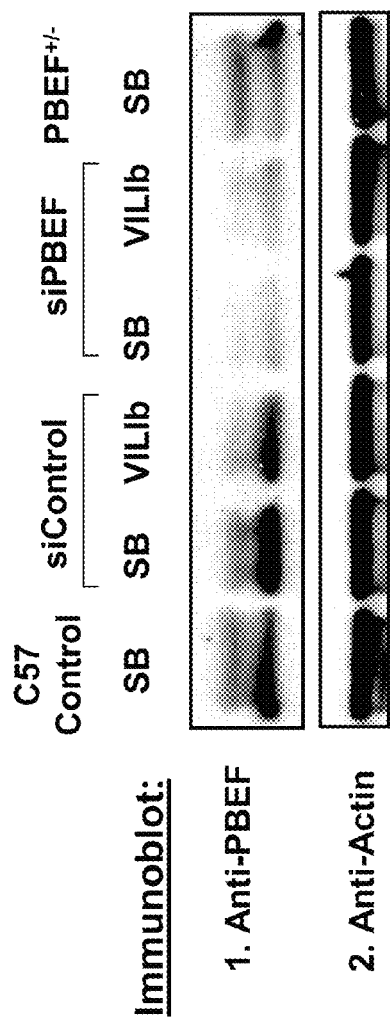
FIG. 16. Intratracheal siPBEF administration inhibits PBEF expression in mouse. The siRNA sequence targeting mouse PBEF was generated using siDESIGN Center website tool (Dharmacon). Silencing RNA specific for PBEF was injected intratracheally in dose 10 mg/kg on 3-d day mice were challenged with VILI. Western blots of PBEF from mouse lung homogenates indicated PBEF expression was decreased by 80% at 72 h post-silencing compared to wild type or siControl and the expression of PBEF in silenced mice was low compared with the PBEF heterozygote knockout mouse (PBEF+/−). β-actin staining served as a control for general protein expression.

Both Invitrogen and Dharmacon siRNAs were effective in downregulating PBEF protein expression in vitro (FIG. 15). This was confirmed with experiments conducted in vivo. Silencing RNA specific for PBEF was injected intratracheally in dose 10 mg/kg on 3-d day mice were challenged with VILI. Western blots of PBEF from mouse lung homogenates indicate PBEF expression is decreased by 80% at 72 h post-silencing compared to wild type or siControl and the expression of PBEF in silenced mice was low compared with the PBEF heterozygote knockout mouse (PBEF+/−) (FIG. 16).

Supplementary Tables

TABLE E1

Supplementary Table E1
Gas exchange and airway parameters after VILI in wild type and PBEF$^{+/-}$ mice.

| | VILIa | | VILIb | |
|---|---|---|---|---|
| | Vehicle | rhPBEF | PBEF$^{+/+}$ | PBEF$^{+/-}$ |
| pH | 7.37 ± 0.06 | 7.38 ± 0.07 | 7.38 ± 0.06 | 7.34 ± 0.03 |
| PCO2, mmHg | 30.1 ± 6.4 | 28.6 ± 3.5 | 23.4 ± 3.4 | 27.7 ± 4.5 |
| PO2, mmHg | 103.0 ± 19.6 | 97.8 ± 7.5 | 76.8 ± 15.8 | 86.3 ± 16.3 |
| HCO3 | 18.0 ± 1.8 | 17.7 ± 2.0 | 14.4 ± 1.7 | 15.7 ± 1.5 |
| PIP, mmHg: 0 hrs | 22.2 ± 1.9 | 22.0 ± 1.8 | 21.8 ± 1.4 | 20.8 ± 1.1 |
| PIP, mmHg: 4 hrs | 23.3 ± 1.8 | 23.4 ± 1.6 | 26.7 ± 2.9 | 22.0 ± 1.6* |

There were no statistical differences in pH, Pa02, PaCO2, HCO3 and peak inspiratory pressure (PIP) values after 4 hours of mechanical ventilation. VILIa-vehicle and VILIa-rhPBEF challenged mice and between VILIb-PBEF$^{+/+}$ and VILIb-PBEF$^{+/-}$ mice. Importantly, the exception was that VILIb-PBEF$^{+/-}$ mice exhibited significantly decreased PIP at the end of the mechanical ventilation period, compared to VILIb-PBEF wild type mice (*p = 0.01).

TABLE E2

Supplementary Table E2
Gene filtering criteria and result by Significance Analysis of Microarrays*.

| Gene list | Pairwise comparison | Delta | False positives | FDR % | Fold change | Significant probe sets | Unique gene | Unique Up | Unique Down |
|---|---|---|---|---|---|---|---|---|---|
| 1 | rhPBEF vs. Control | 0.6 | 27.0 | 4.4 | 2 | 613 | 493 | 375 | 118 |
| 2 | VILIa vs. Control | 0.7 | 12.5 | 4.9 | 2 | 256 | 220 | 144 | 76 |
| 3 | VILIa-rhPBEF vs. Control | 1.2 | 8.4 | 1 | 2 | 836 | 690 | 432 | 258 |
| 4 | VILIa-rhPBEF vs. VILIa | 0.89 | 4.8 | 5.4 | 2 | 82 | 65 | 65 | 0 |
| 5 | PBEF$^{+/-}$ vs. Control | 0.8 | 0.9 | 10.75 | 2 | 8 | 8 | 5 | 3 |
| 6 | VILIb vs. Control | 2.3 | 0.4 | 0.04 | 2 | 901 | 748 | 434 | 314 |
| 7 | VILIb-PBEF$^{+/-}$ vs. Control | 2.1 | 0.5 | 0.11 | 2 | 497 | 421 | 236 | 185 |
| 8 | VILIb-PBEF$^{+/-}$ vs. VILIb | 0.53 | 4.2 | 5.7 | 2 | 74 | 66 | 2 | 64 |

*Gene list 1, 2, 3, 4 are the result of rhPBEF microarray study (GEO accession number GSE9368) and Gene list 5, 6, 7, 8 are the result of rhPBEF$^{+/-}$ study (GEO accession number GSE9314).

TABLE E3

Supplementary Table E3
Biological processes enriched with VILIa and VILIa-rhPBEF dysregulated genes*.

| GO ID | Function Name | VILIa Gene | VILIa q-value | VILIa-rhPBEF Gene | VILIa-rhPBEF q-value |
|---|---|---|---|---|---|
| GO:0006955 | immune response | 14 | 6.40E−09 | 39 | 7.66E−10 |
| GO:0007600 | sensory perception | | | 13 | 2.22E−05 |
| GO:0006468 | protein amino acid phosphorylation | | | 22 | 0.045918849 |
| GO:0006915 | Apoptosis | 6 | 0.027445642 | 17 | 0.003402206 |
| GO:0007242 | intracellular signaling cascade | | | 26 | 4.41E−05 |
| GO:0008283 | cell proliferation | | | 6 | 0.04322093 |
| GO:0016337 | cell-cell adhesion | | | 6 | 8.66E−04 |
| GO:0001525 | Angiogenesis | | | 7 | 0.006702846 |
| GO:0000074 | regulation of progression through cell cycle | | | 18 | 5.81E−06 |
| GO:0006350 | Transcription | | | 53 | 0.002346187 |
| GO:0006986 | response to unfolded protein | | | 8 | 3.52E−04 |
| GO:0006935 | Chemotaxis | | | 12 | 1.69E−06 |
| GO:0007166 | cell surface receptor linked signal transduction | 8 | 1.21E−06 | 14 | 4.83E−08 |
| GO:0006954 | inflammatory response | 7 | 2.10E−05 | 24 | 7.66E−10 |
| GO:0006952 | defense response | | | 7 | 0.013665206 |
| GO:0008285 | negative regulation of cell proliferation | | | 6 | 0.015296511 |
| GO:0006118 | electron transport | 6 | 0.031548868 | 17 | 0.004689141 |
| GO:0006355 | regulation of transcription, DNA-dependent | 22 | 0.025592341 | 69 | 3.03E−04 |
| GO:0007186 | G-protein coupled receptor protein signaling pathway | 13 | 1.64E−04 | 20 | 0.007298116 |
| GO:0045449 | regulation of transcription | | | 21 | 0.004720441 |
| GO:0007264 | small GTPase mediated signal transduction | | | 10 | 0.042044261 |
| GO:0019221 | cytokine and chemokine mediated signaling pathway | | | 7 | 8.06E−06 |
| GO:0007155 | cell adhesion | 7 | 0.048896591 | 23 | 0.001865886 |
| GO:0006508 | Proteolysis | 10 | 0.002595669 | 24 | 3.29E−04 |
| GO:0042981 | regulation of apoptosis | | | 9 | 0.003760921 |
| GO:0009408 | response to heat | | | 6 | 5.28E−05 |
| GO:0007165 | signal transduction | 17 | 3.49E−04 | 44 | 1.24E−07 |
| GO:0006457 | protein folding | | | 11 | 0.020523746 |
| GO:0030154 | cell differentiation | | | 16 | 0.025761644 |
| GO:0050875 | cellular physiological process | | | 10 | 0.001717763 |

*GO categories were identified by Onto-Express software; only biological process with more than 5 genes and q-value < 0.05 were displayed (details in methods section).

TABLE E4

Supplementary Table E4
Biological processes enriched with VILIb and VILIb-PBEF$^{+/-}$ dysregulated genes*.

| GO ID | Function Name | VILIb Gene | VILIb q-value | VILIb-PBEF$^{+/-}$ Gene | VILIb-PBEF$^{+/-}$ q-value |
|---|---|---|---|---|---|
| GO:0006955 | immune response | 28 | 4.00E−10 | 11 | 0.001281 |
| GO:0007600 | sensory perception | 12 | 2.66E−04 | 7 | 0.003736 |
| GO:0008152 | metabolism | 17 | 0.014189 | 10 | 0.035382 |
| GO:0007010 | cytoskeleton organization and biogenesis | 7 | 0.015556 | | |
| GO:0001525 | angiogenesis | 8 | 0.003791 | | |
| GO:0000074 | regulation of progression through cell cycle | 18 | 1.90E−05 | 13 | 3.15E−05 |
| GO:0006350 | transcription | 55 | 0.004129 | | |
| GO:0007275 | development | 31 | 0.006195 | 18 | 0.020402 |
| GO:0006935 | chemotaxis | 10 | 1.73E−04 | 6 | 0.002356 |
| GO:0008284 | positive regulation of cell proliferation | 6 | 0.030441 | | |
| GO:0007166 | cell surface receptor linked signal transduction | 11 | 4.84E−05 | 7 | 7.97E−04 |
| GO:0006954 | inflammatory response | 22 | 5.61E−10 | 15 | 3.08E−10 |
| GO:0006952 | defense response | 7 | 0.019627 | | |
| GO:0007267 | cell-cell signaling | 8 | 3.35E−04 | | |
| GO:0006355 | regulation of transcription, DNA-dependent | 72 | 6.98E−04 | 38 | 0.023903 |
| GO:0007186 | G-protein coupled receptor protein signaling pathway | 24 | 0.001638 | 14 | 0.008684 |
| GO:0045449 | regulation of transcription | 21 | 0.010252 | | |
| GO:0007155 | cell adhesion | 24 | 0.002839 | | |
| GO:0006508 | proteolysis | 23 | 0.002532 | 13 | 0.014688 |
| GO:0007165 | signal transduction | 45 | 4.61E−07 | 24 | 0.001281 |
| GO:0030154 | cell differentiation | 17 | 0.028975 | | |
| GO:0007218 | neuropeptide signaling pathway | 8 | 0.001987 | | |
| GO:0050875 | cellular physiological process | 11 | 0.001035 | 7 | 0.003736 |
| GO:0000122 | negative regulation of transcription from RNA polymerase II promoter | 8 | 0.019598 | | |

*GO categories were identified by OntoExpress software; only biological process with more than 5 genes and q-value < 0.05 were displayed (see methods).

TABLE E5

Supplementary Table E5
Validation of selected DNA microarray genes by RT-PCR and protein expression on bronchoalveolar lavage.

| | VILIa | | | | | | | | | VILIb | | | | | |
|---|---|---|---|---|---|---|---|---|---|---|---|---|---|---|---|
| | rhPBEF | | | VILIa | | | rhPBEF VILIa | | | $PBEF^{+/+}$ VILIb | | | $PBEF^{+/-}$ VILIb | | |
| | DNA | RNA | Protein | DNA | RNA | Protein | DNA | RNA | Protein | DNA | RNA | Protein | DNA | RNA | Protein |
| CxCL1 * | 510 | 146 | 43 | 24 | 10 | 4 | 589 | 148 | 45 | 251 | 67 | 40 | 38 | 14 | 35 |
| CxCL2 * | 2290 | 613 | 115 | 67 | 20 | 5 | 2128 | 1479 | 196 | 157 | 17 | 26 | 32 | 2 | 20 |
| BCL3 | 7 | 4 | ** | 4 | 3 | ** | 11 | 10 | ** | 11 | ** | ** | 6 | ** | ** |
| Map3k8 | 3 | 1 | ** | ** | ** | ** | 4 | 2 | ** | 4 | ** | ** | ** | ** | ** |
| MMP9 | 16 | 16 | ** | ** | ** | ** | 13 | 1 | ** | 7 | ** | ** | 7 | ** | ** |
| IL-6 | 240 | ** | 9 | 179 | ** | 4 | 900 | ** | 27 | 825 | ** | 462 | 188 | ** | 50 |
| IL-1-β | 70 | ** | 3 | 52 | ** | 1 | 87 | ** | 3 | 16 | ** | 23 | 9 | ** | 27 |
| TNF-α | 23 | ** | 43 | 2 | ** | 4 | 23 | ** | 45 | 12 | ** | 17 | 6 | ** | 12 |
| BC018473 | ** | ** | ** | ** | ** | ** | ** | ** | ** | ** | ** | ** | 204 | 5202 | ** |

Depicted are results expressed as the average fold change increase over control groups. * CxCl1 is also known as KC and * CxCL2 is also known as MIP2α. ** reflects that these values were not determined. Protein values reflects BAL levels by ELISA.

REFERENCES

The following references, to the extent that they provide exemplary procedural or other details supplementary to those set forth herein, are specifically incorporated herein by reference.

U.S. Pat. No. 4,415,723
U.S. Pat. No. 4,458,066
U.S. Pat. No. 4,554,101
U.S. Pat. No. 4,683,195
U.S. Pat. No. 4,683,202
U.S. Pat. No. 4,797,368
U.S. Pat. No. 4,800,159
U.S. Pat. No. 4,816,567
U.S. Pat. No. 4,883,750
U.S. Pat. No. 5,139,941
U.S. Pat. No. 5,187,260
U.S. Pat. No. 5,279,721
U.S. Pat. No. 5,795,715
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,882,864
U.S. Pat. No. 5,889,136
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Patent Publn. 20030147966
U.S. Patent Publn. 20030223938
U.S. Patent Publn. 20050143336
Aksentijevich et al., *Hum. Gene Ther.,* 7(9):1111-1122, 1996.
Ausubel et al., In: *Current Protocols in Molecular Biology,* John, Wiley & Sons, Inc, NY, 1994; 1996.
Bellus, *J. Macromol. Sci. Pure Appl. Chem.,* A31(1): 1355-1376, 1994.
Bosher and Labouesse, *Nat. Cell. Biol.,* 2(2):E31-E36, 2000.
Caplen et al., *Gene,* 252(1-2):95-105, 2000.
Chada et al., *Mol. Ther.,* 7:S446, 2003.
Clackson et al., *Nature,* 352:624-628, 1991.
Coffin, In: *Virology,* Fields et al. (Eds.), Raven Press, NY, 1437-1500, 1990.
Consortium, *Nucleic Acids Res.,* 34:D322-326, 2006.
Dreyfuss et al., *Am. Rev. Respir. Dis.,* 137:1159-1164, 1988.
Dudek et al., *Free Radic. Biol. Med.,* 31:651-658, 2001.
Elbashir et al., *Nature,* 411(6836):494-498, 2001.
European Appln. 320 308,
European Appln. 329 822
Feigner et al., *Proc. Natl. Acad. Sci. USA,* 84(21):7413-7417, 1987.

Fire et al., *Nature*, 391(6669):806-811, 1998.
Fodor et al., *Science*, 251:767-777, 1991.
Fraley et al., *Proc. Natl. Acad. Sci. USA*, 76:3348-3352, 1979.
Freshney, In: *Animal Cell Culture*, A Practical Approach, 2$^{nd}$ Ed., Oxford Press, UK, 1992.
Frohman, In: *PCR Protocols: A Guide To Methods And Applications*, Academic Press, N.Y., 1990.
Gabizon et al., *Cancer Res.*, 50(19):6371-6378, 1990.
Garcia et al., *Oncogene*, 20:2499-2513, 2001.
GB Appln. 2 202 328
GB Appln. 2 202 328
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Grishok et al., *Science*, 287:2494-2497, 2000.
Hacia et al., *Nature Genet.*, 14:441-449, 1996.
Holen et al., *Invest. New Drugs*, 26:45-51, 2008.
Innis et al., *Proc. Natl. Acad. Sci. USA*, 85(24):9436-9440, 1988.
Inouye and Inouye, *Nucleic Acids Res.*, 13:3101-3109, 1985.
Jia et al., *J. Clin. Invest.*, 113:1318-1327, 2004.
Kaneda et al., *Science*, 243:375-378, 1989.
Karlsson et al., *EMBO J.*, 5:2377-2385, 1986.
Kato et al, *J. Biol. Chem.*, 266:3361-3364, 1991.
Ketting et al., *Cell*, 99(2):133-141, 1999.
Kohler and Milstein, *Nature*, 256:495-497, 1975.
Kwoh et al., *Proc. Natl. Acad. Sci. USA*, 86:1173, 1989.
Li and Wong, *Proc. Natl. Acad. Sci. USA*, 98:31-36, 2001.
Lin and Avery, *Nature*, 402:128-129, 1999.
Liu et al., *Cancer Res.*, 55(14):3117-3122, 1995.
Luscher et al., *Neth. J. Med.*, 50(5):204-210, 1997.
Ma et al., *Am. J. Physiol. Lung Cell Mol. Physiol.*, 289:L468-477, 2005.
Macejak and Sarnow, *Nature*, 353:90-94, 1991.
Mann et al., *Cell*, 33:153-159, 1983.
Marks et al., *J. Mol. Biol.*, 222:581-597, 1991.
Moitra et al., *Transl. Res.*, 150:253-265, 2007.
Montgomery et al., *Proc. Natl. Acad. Sci. USA*, 95:15502-15507, 1998.
Nichols et al., *Development*, 110:1341-1348, 1990.
Nicolas and Rubinstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Nonas et al., *Am. J. Physiol. Lung Cell Mol. Physiol.*, 293:L292-302, 2007.
Ohara et al., *Proc. Natl. Acad. Sci. USA*, 86:5673-5677, 1989.
Parsons et al., *Crit. Care Med.*, 33:1-6; discussion 230-232, 2005.
Paskind et al., *Virology*, 67:242-248, 1975.
PCT Appln. PCT/US89/01025
PCT Appln. WO 00/44914
PCT Appln. WO 01/68836
PCT Appln. WO 84/03564.
PCT Appln. WO 88/10315
PCT Appln. WO 89/06700
PCT Appln. WO 90/07641
PCT Appln. WO 98/07408
PCT Appln. WO 99/32619
PCT/US87/00880
Pearson, *Radiology*, 179(1):9-14, 1991.
Pease et al., *Proc. Natl. Acad. Sci. USA*, 91:5022-5026, 1994.
Pelletier and Sonenberg, *Nature*, 334(6180):320-325, 1988.
Peng et al., *Am. J. Respir. Crit. Care Med.*, 169:1245-1251, 2004.
Ranieri et al., *JAMA*, 282:54-61, 1999.
Remington's Pharmaceutical Sciences" 15$^{th}$ Ed., 1035-1038 and 1570-1580, 1990.
Revollo et al., *Cell Metab.*, 6(5):363-375, 2007.
Revollo et al., *J Biol Chem.*, 279(49):50754-50763, 2004.
Rubenfeld et al., *N. Engl. J. Med.*, 353:1685-1693, 2005.
Samal et al., *Mol. Cell Biol.*, 14(2):1431-1417, 1994.
Sambrook and Russell, Molecular Cloning: A Laboratory Manual 3$^{rd}$ Ed., Cold Spring Harbor Laboratory Press, 2001.
Sharp and Zamore, *Science*, 287:2431-2433, 2000.
Sharp, *Genes Dev.*, 13:139-141, 1999.
Shoemaker et al., *Nature Genetics*, 14:450-456, 1996.
Slutsky and Tremblay, *Am. J. Respir. Crit. Care Med.*, 157:1721-1725, 1998.
Smyth-Templeton et al., *DNA Cell Biol.*, 21(12):857-867, 1997.
Solodin et al., *Biochemistry*, 34(41):13537-13544, 1995.
Tabara et al., *Cell*, 99(2):123-132, 1999.
Team RDC, A language and environmental for statistical computing. 2005; ISBN 3-900051-07-0.
Temin, In: *Gene Transfer*, Kucherlapati (Ed.), NY, Plenum Press, 149-188, 1986.
Templeton et al., *Nat. Biotechnol.*, 15(7):647-652, 1997.
The acute respiratory distress syndrome network, *N. Engl. J. Med.*, 342:1301-1308, 2000.
Thierry et al., *Proc. Natl. Acad. Sci. USA*, 92(21):9742-9746, 1995.
Toole, *Nat. Rev. Cancer*, 4(7):528-539, 2004.
Tremblay et al., *Crit. Care Med.*, 30:1693-1700, 2002.
Tremblay et al., *J. Clin. Invest.*, 99:944-952, 1997.
Tsukamoto et al., *Nat. Genet.*, 9(3):243-248, 1995.
Turley et al., *J. Biol. Chem.*, 277(7):4589-4592, 2002.
Walker et al., *Nucleic Acids Res.* 20(7):1691-1696, 1992.
Ware and Matthay, *N. Engl. J. Med.*, 342:1334-1349, 2000.
Wincott et al., *Nucleic Acids Res.*, 23(14):2677-2684, 1995.
Wong et al., *Gene*, 10:87-94, 1980.
Wu et al., *J. Am. Stat. Assoc.*, 99:909-917, 2004.
Yang and Huang, *Gene Therapy*, 4 (9):950-960, 1997.
Ye et al., *Am. J. Respir. Crit. Care Med.*, 171:361-370, 2005.
Zhu et al., *Science*, 261(5118):209-211, 1993.

What is claimed is:

1. A method for treatment of an inflammatory condition of the lungs or disease of the lungs in a human patient comprising administering to a human patient an effective amount of a Pre-B Cell Colony-Enhancing Factor (PBEF) inhibitor, wherein the human patient has symptoms of the inflammatory condition or disease, wherein the PBEF inhibitor is a neutralizing PBEF antibody.

2. The method of claim 1, wherein the inflammatory disease or condition of the lungs is acute lung injury (ALI), ventilator-induced lung injury (VILI), or acute respiratory distress syndrome (ARDS).

3. The method of claim 1, wherein the inhibitor is administered to the patient intravenously, intraarterially, intraperitoneally, intrapleurally, intratracheally, topically, subcutaneously, mucosally, intrapericardially, orally, or by inhalation.

4. The method of claim 1, wherein the effective amount of the Pre-B Cell Colony-Enhancing Factor (PBEF) inhibitor is administered before the human patient has been placed on a ventilator.

5. The method of claim 1, wherein the effective amount of the Pre-B Cell Colony-Enhancing Factor (PBEF) inhibitor is administered after the human patient has been placed on a ventilator.

6. A method for treating a patient with acute lung injury (ALI), ventilator-induced lung injury (VILI), or acute respiratory distress syndrome (ARDS) comprising administering to the patient an effective amount of a Pre-B Cell Colony-Enhancing Factor (PBEF) inhibitor, wherein the PBEF inhibitor is a neutralizing PBEF antibody.

7. The method of claim 6, wherein the inhibitor is administered to the patient intravenously, intraarterially, intraperitoneally, intrapleurally, intratracheally, topically, subcutaneously, mucosally, intrapericardially, orally, or by inhalation.

8. The method of claim 6, wherein the effective amount of the Pre-B Cell Colony-Enhancing Factor (PBEF) inhibitor is administered before the patient has been placed on a ventilator.

9. The method of claim 6, wherein the patient has sepsis or symptoms of sepsis.

10. The method of claim 6, wherein the effective amount of the Pre-B Cell Colony-Enhancing Factor (PBEF) inhibitor is administered after the patient has been placed on a ventilator.

11. A method for preventing ventilator-induced lung injury (VILI) in a human patient comprising administering to a human patient an effective amount of a Pre-B Cell Colony-Enhancing Factor (PBEF) inhibitor, wherein the PBEF inhibitor is a neutralizing PBEF antibody, and wherein the administration occurs before the patient is placed on a ventilator.

* * * * *

SEQUENCE LISTING

<160> NUMBER OF SEQ ID NOS: 9

<210> SEQ ID NO 1
<211> LENGTH: 4593
<212> TYPE: DNA
<213> ORGANISM: Homo sapiens
<220> FEATURE:
<221> NAME/KEY: CDS
<222> LOCATION: (309)..(1784)

<400> SEQUENCE: 1

```
gctgccgcgc cccgccctttt ctcggccccc ggagggtgac ggggtgaagg cgggggaacc      60
gaggtgggga gtccgccaga gctcccagac tgcgagcacg cgagccgccg cagccgtcac     120
ccgcgccgcg tcacggctcc cgggcccgcc ctcctctgac ccctcccctc tctccgtttc     180
cccctctccc cctcctccgc cgaccgagca gtgacttaag caacggagcg cggtgaagct     240 cattttctc cttcctcgca gccgcgccag ggagctcgcg gcgcgcggcc cctgtcctcc     300
```

```
ggcccgag atg aat cct gcg gca gaa gcc gag ttc aac atc ctc ctg gcc      350
         Met Asn Pro Ala Ala Glu Ala Glu Phe Asn Ile Leu Leu Ala
           1               5                  10 acc gac tcc tac aag gtt act cac tat aaa caa tat cca ccc aac aca      398
Thr Asp Ser Tyr Lys Val Thr His Tyr Lys Gln Tyr Pro Pro Asn Thr
 15              20                  25                  30 agc aaa gtt tat tcc tac ttt gaa tgc cgt gaa aag aag aca gaa aac      446
Ser Lys Val Tyr Ser Tyr Phe Glu Cys Arg Glu Lys Lys Thr Glu Asn
                 35                  40                  45 tcc aaa tta agg aag gtg aaa tat gag gaa aca gta ttt tat ggg ttg      494
Ser Lys Leu Arg Lys Val Lys Tyr Glu Glu Thr Val Phe Tyr Gly Leu
         50                  55                  60 cag tac att ctt aat aag tac tta aaa ggt aaa gta gta acc aaa gag      542
Gln Tyr Ile Leu Asn Lys Tyr Leu Lys Gly Lys Val Val Thr Lys Glu
             65                  70                  75 aaa atc cag gaa gcc aaa gat gtc tac aaa gaa cat ttc caa gat gat      590
Lys Ile Gln Glu Ala Lys Asp Val Tyr Lys Glu His Phe Gln Asp Asp
 80                  85                  90 gtc ttt aat gaa aag gga tgg aac tac att ctt gag aag tat gat ggg      638
Val Phe Asn Glu Lys Gly Trp Asn Tyr Ile Leu Glu Lys Tyr Asp Gly
 95                 100                 105                 110 cat ctt cca ata gaa ata aaa gct gtt cct gag ggc ttt gtc att ccc      686
His Leu Pro Ile Glu Ile Lys Ala Val Pro Glu Gly Phe Val Ile Pro
                115                 120                 125 aga gga aat gtt ctc ttc acg gtg gaa aac aca gat cca gag tgt tac      734
Arg Gly Asn Val Leu Phe Thr Val Glu Asn Thr Asp Pro Glu Cys Tyr
         130                 135                 140 tgg ctt aca aat tgg att gag act att ctt gtt cag tcc tgg tat cca      782
Trp Leu Thr Asn Trp Ile Glu Thr Ile Leu Val Gln Ser Trp Tyr Pro
             145                 150                 155 atc aca gtg gcc aca aat tct aga gag cag aag aaa ata ttg gcc aaa      830
Ile Thr Val Ala Thr Asn Ser Arg Glu Gln Lys Lys Ile Leu Ala Lys
 160                 165                 170 tat ttg tta gaa act tct ggt aac tta gat ggt ctg gaa tac aag tta      878
Tyr Leu Leu Glu Thr Ser Gly Asn Leu Asp Gly Leu Glu Tyr Lys Leu
175                 180                 185                 190 cat gat ttt ggc tac aga gga gtc tct tcc caa gag act gct ggc ata      926
His Asp Phe Gly Tyr Arg Gly Val Ser Ser Gln Glu Thr Ala Gly Ile
                195                 200                 205 gga gca tct gct cac ttg gtt aac ttc aaa gga aca gat aca gta gca      974
Gly Ala Ser Ala His Leu Val Asn Phe Lys Gly Thr Asp Thr Val Ala
         210                 215                 220 gga ctt gct cta att aaa aaa tat tat gga acg aaa gat cct gtt cca     1022
Gly Leu Ala Leu Ile Lys Lys Tyr Tyr Gly Thr Lys Asp Pro Val Pro
             225                 230                 235 ggc tat tct gtt cca gca gca gaa cac agt acc ata aca gct tgg ggg     1070
Gly Tyr Ser Val Pro Ala Ala Glu His Ser Thr Ile Thr Ala Trp Gly
 240                 245                 250 aaa gac cat gaa aaa gat gct ttt gaa cat att gta aca cag ttt tca     1118
Lys Asp His Glu Lys Asp Ala Phe Glu His Ile Val Thr Gln Phe Ser
255                 260                 265                 270
```

| | | |
|---|---|---|
| tca gtg cct gta tct gtg gtc agc gat agc tat gac att tat aat gcg<br>Ser Val Pro Val Ser Val Val Ser Asp Ser Tyr Asp Ile Tyr Asn Ala<br>     275        280      285 | | 1166 |
| tgt gag aaa ata tgg ggt gaa gat cta aga cat tta ata gta tca aga<br>Cys Glu Lys Ile Trp Gly Glu Asp Leu Arg His Leu Ile Val Ser Arg<br>290        295        300 | | 1214 |
| agt aca cag gca cca cta ata atc aga cct gat tct gga aac cct ctt<br>Ser Thr Gln Ala Pro Leu Ile Ile Arg Pro Asp Ser Gly Asn Pro Leu<br>   305        310        315 | | 1262 |
| gac act gtg tta aag gtt ttg gag att tta ggt aag aag ttt cct gtt<br>Asp Thr Val Leu Lys Val Leu Glu Ile Leu Gly Lys Lys Phe Pro Val<br>320        325        330 | | 1310 |
| act gag aac tca aag ggt tac aag ttg ctg cca cct tat ctt aga gtt<br>Thr Glu Asn Ser Lys Gly Tyr Lys Leu Leu Pro Pro Tyr Leu Arg Val<br>335        340        345        350 | | 1358 |
| att caa ggg gat gga gta gat att aat acc tta caa gag att gta gaa<br>Ile Gln Gly Asp Gly Val Asp Ile Asn Thr Leu Gln Glu Ile Val Glu<br>        355        360        365 | | 1406 |
| ggc atg aaa caa aaa atg tgg agt att gaa aat att gcc ttc ggt tct<br>Gly Met Lys Gln Lys Met Trp Ser Ile Glu Asn Ile Ala Phe Gly Ser<br>370        375        380 | | 1454 |
| ggt gga ggt ttg cta cag aag ttg aca aga gat ctc ttg aat tgt tcc<br>Gly Gly Gly Leu Leu Gln Lys Leu Thr Arg Asp Leu Leu Asn Cys Ser<br>   385        390        395 | | 1502 |
| ttc aag tgt agc tat gtt gta act aat ggc ctt ggg att aac gtc ttc<br>Phe Lys Cys Ser Tyr Val Val Thr Asn Gly Leu Gly Ile Asn Val Phe<br>400        405        410 | | 1550 |
| aag gac cca gtt gct gat ccc aac aaa agg tcc aaa aag ggc cga tta<br>Lys Asp Pro Val Ala Asp Pro Asn Lys Arg Ser Lys Lys Gly Arg Leu<br>415        420        425        430 | | 1598 |
| tct tta cat agg acg cca gca ggg aat ttt gtt aca ctg gag gaa gga<br>Ser Leu His Arg Thr Pro Ala Gly Asn Phe Val Thr Leu Glu Glu Gly<br>        435        440        445 | | 1646 |
| aaa gga gac ctt gag gaa tat ggt cag gat ctt ctc cat act gtc ttc<br>Lys Gly Asp Leu Glu Glu Tyr Gly Gln Asp Leu Leu His Thr Val Phe<br>450        455        460 | | 1694 |
| aag aat ggc aag gtg aca aaa agc tat tca ttt gat gaa ata aga aaa<br>Lys Asn Gly Lys Val Thr Lys Ser Tyr Ser Phe Asp Glu Ile Arg Lys<br>   465        470        475 | | 1742 |
| aat gca cag ctg aat att gaa ctg gaa gca gca cat cat tag<br>Asn Ala Gln Leu Asn Ile Glu Leu Glu Ala Ala His His<br>480        485        490 | | 1784 |
| gctttatgac tgggtgtgtg ttgtgtgtat gtaatacata atgtttattg tacagatgtg | | 1844 |
| tggggtttgt gttttatgat acattacagc caaattattt gttggtttat ggacatactg | | 1904 |
| ccctttcatt ttttttcttt tccagtgttt aggtgatctc aaattaggaa atgcatttaa | | 1964 |
| ccatgtaaaa gatgagtgct aaagtaagct ttttagggcc ctttgccaat aggtagtcat | | 2024 |
| tcaatctggt attgatcttt tcacaaataa cagaactgag aaacttttat atataactga | | 2084 |
| tgatcacata aaacagattt gcataaaatt accatgattg ctttatgttt atatttaact | | 2144 |
| tgtattttg tacaaacaag attgtgtaag atatatttga agtttcagtg atttaacagt | | 2204 |
| ctttccaact tttcatgatt tttatgagca cagactttca agaaaatact tgaaaataaa | | 2264 |
| ttacattgcc ttttgtccat taatcagcaa ataaaacatg gccttaacaa agttgtttgt | | 2324 |
| gttattgtac aatttgaaaa ttatgtcggg acatacccta tagaattact aaccttactg | | 2384 |
| ccccttgtag aatatgtatt aatcattcta cattaaagaa aataatggtt cttactggaa | | 2444 |

```
tgtctaggca ctgtacagtt attatatatc ttggttgttg tattgtacca gtgaaatgcc    2504
aaatttgaaa ggcctgtact gcaattttat atgtcagaga ttgcctgtgg ctctaatatg    2564
cacctcaaga ttttaaggag ataatgtttt tagagagaat ttctgcttcc actatagaat    2624
atatacataa atgtaaaata cttacaaaag tggaagtagt gtattttaaa gtaattacac    2684
ttctgaattt attttttcata ttctatagtt ggtatgactt aaatgaatta ctggagtggg    2744
tagtgagtgt acttaaatgt ttcaattctg ttatattttt tattaagttt ttaaaaaatt    2804
aaattggata ttaaattgta tggacatcat ttattaattt taaactgaat gccctcaata    2864
agtaatactg aagcacattc ttaaatgaag ataaattatc tccaatgaaa agcatgacat    2924
gtgtttcaat agaagaatct taagttggct aaattcaaag tgcttgacat caaaatgttc    2984
tagagtgatt agctactaga ttctgaatca tacatcacat ctgactagag accagtttct    3044
ttcgaatgat tcttttatgt atgtagatct gttcttctga ggcagcggtt ggccaactat    3104
agcccaaagg ccaaatttgg acttcttttt ataaatgcag attgtctatg gctgctttcc    3164
cactactcca gcctaaggta aacagctgca atagaagcca aatgagaatc gcaaagccca    3224
aaatgtttat taacctgccc tttacacaaa attacacaaa aagtttcctg atctctgttc    3284
taagaaaagg agtgtgcctt gcatttaaaa ggaaatgttg gtttctaggg aagggaggag    3344
gctaaataat tgatacggaa ttttcctctt ttgtcttctt ttttctcact taagaatccg    3404
atactggaag actgatttag aaaagttttt aacatgacat taaatgtgaa attttaaaaa    3464
ttgaaaagcc ataaatcatc tgtttttaaat agttacatga gaaaatgatc actagaataa    3524
cctaattaga agtgttatct tcattaaatg ttttttgtaa gtggtattag aaagaatatg    3584
tttttcagat ggttctttaa acatgtagtg agaacaataa gcattattca cttttagtaa    3644
gtcttctgta atccatgata taaaataatt ttaaaatgat ttttaatgt atttgagtaa    3704 agatgagtag tattaagaaa aacacacatt tcttcacaaa atgtgctaag gggcgtgtaa    3764
agaatcaaaa gaaactatta ccaataatag ttttgataat cacccataat tttgtgttta    3824
aacattgaaa ttatagtaca gacagtattc tctgtgttct gtgaatttca gcagcttcag    3884
aatagagttt aatttagaaa tttgcagtga aaaaagctat ctctttgttc acaaccataa    3944
atcaggagat ggagattaat tctattggct cttagtcact tggaactgat taattctgac    4004
tttctgtcac taagcacttg gtatttggcc atctccattc tgagcaccaa acggttaaca    4064
cgaatgtcca ctagaactct gctgtgtgtc acccttaaat cagtctaaat cttccagaca    4124
aaagcaaatg gcatttatgg atttaagtca ttagattttc aactgacatt aattaatccc    4184
tcttgattga ttatatcatc aagtatttat atcttaaata ggaggtagga tttctgtgtt    4244
aagactctta tttgtaccct ataattaaag taaaatgttt tttatgagta tcccttgttt    4304
tcccttctta aattgttatc aaacaatttt tataatgaaa tctatcttgg aaaattagaa    4364
agaaaaatgg caaggtattt attgttctgt ttgccataat ttagaactca cacttaagta    4424
ttttgtagtt ttacattcct ttttaaccca ttcagtggag aatgtcagct tttctcccaa    4484
gttgtatgtt aagtctattc taatatgtac tcaacatcaa gttataaaca tgtaataaac    4544
atggaaataa agtttagctc tattagtgaa gtgttaaaaa aaaaaaaaa                4593
```

<210> SEQ ID NO 2
<211> LENGTH: 491
<212> TYPE: PRT
<213> ORGANISM: Homo sapiens

<400> SEQUENCE: 2

Met Asn Pro Ala Ala Glu Ala Glu Phe Asn Ile Leu Leu Ala Thr Asp
1               5                   10                  15

Ser Tyr Lys Val Thr His Tyr Lys Gln Tyr Pro Asn Thr Ser Lys
            20                  25                  30

Val Tyr Ser Tyr Phe Glu Cys Arg Glu Lys Lys Thr Glu Asn Ser Lys
        35                  40                  45

Leu Arg Lys Val Lys Tyr Glu Glu Thr Val Phe Tyr Gly Leu Gln Tyr
    50                  55                  60

Ile Leu Asn Lys Tyr Leu Lys Gly Lys Val Val Thr Lys Glu Lys Ile
65                  70                  75                  80

Gln Glu Ala Lys Asp Val Tyr Lys Glu His Phe Gln Asp Asp Val Phe
                85                  90                  95

Asn Glu Lys Gly Trp Asn Tyr Ile Leu Glu Lys Tyr Asp Gly His Leu
            100                 105                 110

Pro Ile Glu Ile Lys Ala Val Pro Glu Gly Phe Val Ile Pro Arg Gly
        115                 120                 125

Asn Val Leu Phe Thr Val Glu Asn Thr Asp Pro Glu Cys Tyr Trp Leu
    130                 135                 140

Thr Asn Trp Ile Glu Thr Ile Leu Val Gln Ser Trp Tyr Pro Ile Thr
145                 150                 155                 160

Val Ala Thr Asn Ser Arg Glu Gln Lys Lys Ile Leu Ala Lys Tyr Leu
                165                 170                 175

Leu Glu Thr Ser Gly Asn Leu Asp Gly Leu Glu Tyr Lys Leu His Asp
            180                 185                 190

Phe Gly Tyr Arg Gly Val Ser Ser Gln Glu Thr Ala Gly Ile Gly Ala
        195                 200                 205

Ser Ala His Leu Val Asn Phe Lys Gly Thr Asp Thr Val Ala Gly Leu
    210                 215                 220

Ala Leu Ile Lys Lys Tyr Tyr Gly Thr Lys Asp Pro Val Pro Gly Tyr
225                 230                 235                 240

Ser Val Pro Ala Ala Glu His Ser Thr Ile Thr Ala Trp Gly Lys Asp
                245                 250                 255

His Glu Lys Asp Ala Phe Glu His Ile Val Thr Gln Phe Ser Ser Val
            260                 265                 270

Pro Val Ser Val Val Ser Asp Ser Tyr Asp Ile Tyr Asn Ala Cys Glu
        275                 280                 285

Lys Ile Trp Gly Glu Asp Leu Arg His Leu Ile Val Ser Arg Ser Thr
    290                 295                 300

Gln Ala Pro Leu Ile Ile Arg Pro Asp Ser Gly Asn Pro Leu Asp Thr
305                 310                 315                 320

Val Leu Lys Val Leu Glu Ile Leu Gly Lys Lys Phe Pro Val Thr Glu
                325                 330                 335

Asn Ser Lys Gly Tyr Lys Leu Leu Pro Pro Tyr Leu Arg Val Ile Gln
            340                 345                 350

Gly Asp Gly Val Asp Ile Asn Thr Leu Gln Glu Ile Val Glu Gly Met
        355                 360                 365

Lys Gln Lys Met Trp Ser Ile Glu Asn Ile Ala Phe Gly Ser Gly Gly
    370                 375                 380

Gly Leu Leu Gln Lys Leu Thr Arg Asp Leu Leu Asn Cys Ser Phe Lys
385                 390                 395                 400

Cys Ser Tyr Val Val Thr Asn Gly Leu Gly Ile Asn Val Phe Lys Asp
                405                 410                 415

```
Pro Val Ala Asp Pro Asn Lys Arg Ser Lys Lys Gly Arg Leu Ser Leu
            420                 425                 430

His Arg Thr Pro Ala Gly Asn Phe Val Thr Leu Glu Glu Gly Lys Gly
        435                 440                 445

Asp Leu Glu Glu Tyr Gly Gln Asp Leu Leu His Thr Val Phe Lys Asn
        450                 455                 460

Gly Lys Val Thr Lys Ser Tyr Ser Phe Asp Glu Ile Arg Lys Asn Ala
465                 470                 475                 480

Gln Leu Asn Ile Glu Leu Glu Ala Ala His His
                485                 490

<210> SEQ ID NO 3
<211> LENGTH: 1413
<212> TYPE: DNA
<213> ORGANISM: Mus musculus

<400> SEQUENCE: 3
ggacatcctg gccaaggctc ctacttcaag gcttggtgat gtcttgtgga agagctactt      60
gaatggctca actctctctt gctggagtcg agcagcgcct cttaagtcct ccccctcaga     120
cccaagtctc agagggatga gagggagatt cctggtctcc cctccatgga caaggacaca     180
cctcctcact aacattgtcc cctccattgc caacctttc acacgactca tggatctctt      240 cctactctg ctatccctgt cgtggagctc cacctctaac tccttcttcc caagtcccca      300
ttacaccagg accggttcca gatattgaag agatcttagt gaggaagacc acttctggca     360
gagtccccac cttaactcta tgtaaggtgt ggacactccc catggccccg agatgaggac     420
cctcccatgg gccccgaaat gaggacccctt tcatggttta aacagcctc ttgacctcta     480 tcctcaaaga atctgaatcc ttcttttca gagaaactcc agggtttaac ttttctcttg     540
gagactatac ccatcagcca acttgggatg actgtcaaca actcctgaga tgttcttttc     600
ctcacaggcc tgggaatgca tcttctggga agccaggaaa ttgcttccta gtgacaacag     660 tcaccttca tatgcccaga ttggaaccct aatgaggcag cagcccatgg taaccttgaa      720
agtggaggaa aaaccaatgg actttctggt aggcatggaa gccaactgaa ggaaccaaag     780
tgactcctag ccacgagatg cagcctggtg ctaaacaata cccccagtac aaggaaatgc     840
catgtcaacc tcgaaaaaga tgatgttact ccaatatgca gatgacctca tcagggcagc     900
cagccaacat ggacacgtgc acaatggcca ctcaagagct cctaggacct ctccaatgcc     960
tgagatactt gatggatgtg caccaagaag gcccaactct gcaaccggaa tgccacatac    1020
ttgggattcc atgaagggag gaagtcctag tttatgtcat gtgaacagga atcttgggt    1080 tggcgagatg gctcaacggc taagaacact tattgctctt ctgaaggccc tgagttcaaa    1140
tcccagcaat cacatggtgg ctcacaacca cctataatga gatctgatgc cctcttctgg    1200
tgtgtctgaa ctcagctaca gggtacttat gtttaataat aaataaatct ttgagccaga    1260
gtgagcaagt ttgaccagag cgagcggggc cgagtggagc tagtaaaggt cctaaaattt    1320
caattccgaa caaccacatg aaggcccaca accatctgta cagctacagt gtactcacat    1380
aaaataaaga aatctttaaa aaaaaaaaaa aaa                                 1413

<210> SEQ ID NO 4
<211> LENGTH: 25
<212> TYPE: RNA
<213> ORGANISM: Artificial
<220> FEATURE:
<223> OTHER INFORMATION: Synthetic primer
```

```
-continued

<400> SEQUENCE: 4
ccacccaaca caagcaaagu uuauu                                          25

<210> SEQ ID NO 5
<211> LENGTH: 21
<212> TYPE: RNA
<213> ORGANISM: Artificial
<220> FEATURE:
<223> OTHER INFORMATION: Synthetic primer

<400> SEQUENCE: 5
ggaaagacca ugagaaagau u                                              21

<210> SEQ ID NO 6
<211> LENGTH: 21
<212> TYPE: RNA
<213> ORGANISM: Artificial
<220> FEATURE:
<223> OTHER INFORMATION: Synthetic primer

<400> SEQUENCE: 6
uaaggcuaug aagagauacu u                                              21

<210> SEQ ID NO 7
<211> LENGTH: 20
<212> TYPE: DNA
<213> ORGANISM: Artificial
<220> FEATURE:
<223> OTHER INFORMATION: Synthetic primer

<400> SEQUENCE: 7
cggatgcctt agcctgaagt                                                20

<210> SEQ ID NO 8
<211> LENGTH: 20
<212> TYPE: DNA
<213> ORGANISM: Artificial
<220> FEATURE:
<223> OTHER INFORMATION: Synthetic primer

<400> SEQUENCE: 8
gggagtgaca cagcaaatca                                                20

<210> SEQ ID NO 9
<211> LENGTH: 20
<212> TYPE: DNA
<213> ORGANISM: Artificial
<220> FEATURE:
<223> OTHER INFORMATION: Synthetic primer

<400> SEQUENCE: 9
cagcagcaga ccattttcaa                                                20
```